(12) United States Patent
Deisseroth et al.

(10) Patent No.: US 9,284,353 B2
(45) Date of Patent: Mar. 15, 2016

(54) MAMMALIAN CODON OPTIMIZED NUCLEOTIDE SEQUENCE THAT ENCODES A VARIANT OPSIN POLYPEPTIDE DERIVED FROM NATROMONAS PHARAONIS (NPHR)

(71) Applicant: The Board of Trustees of the Leland Stanford Junior University, Palo Alto, CA (US)

(72) Inventors: Karl Deisseroth, Stanford, CA (US); Feng Zhang, Cambridge, MA (US); Viviana Gradinaru, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 13/855,413

(22) Filed: Apr. 2, 2013

(65) Prior Publication Data

US 2014/0113367 A1    Apr. 24, 2014

Related U.S. Application Data

(63) Continuation of application No. 13/208,419, filed on Aug. 12, 2011, which is a continuation of application No. 12/041,628, filed on Mar. 3, 2008, now abandoned.

(60) Provisional application No. 60/904,303, filed on Mar. 1, 2007.

(51) Int. Cl.
| | |
|---|---|
| C07K 14/00 | (2006.01) |
| A01K 67/033 | (2006.01) |
| A61K 48/00 | (2006.01) |
| A61N 5/06 | (2006.01) |
| C07K 14/195 | (2006.01) |
| C07K 14/215 | (2006.01) |
| C12N 15/86 | (2006.01) |
| A61K 38/00 | (2006.01) |

(52) U.S. Cl.
CPC ............ *C07K 14/00* (2013.01); *A01K 67/0333* (2013.01); *A61K 48/005* (2013.01); *A61K 48/0058* (2013.01); *A61K 48/0083* (2013.01); *A61N 5/0613* (2013.01); *A61N 5/0622* (2013.01); *C07K 14/195* (2013.01); *C07K 14/215* (2013.01); *C12N 15/86* (2013.01); *A01K 2217/052* (2013.01); *A01K 2227/703* (2013.01); *A01K 2267/0356* (2013.01); *A61K 38/00* (2013.01); *C12N 2710/10343* (2013.01); *C12N 2710/16643* (2013.01); *C12N 2740/16043* (2013.01); *C12N 2740/16071* (2013.01); *C12N 2750/14143* (2013.01); *C12N 2830/002* (2013.01)

(58) Field of Classification Search
CPC ............... C07K 14/215; C07K 14/195; C12N 2750/14143
See application file for complete search history.

(56) References Cited

U.S. PATENT DOCUMENTS

| | | | |
|---|---|---|---|
| 2,968,302 | A | 1/1961 | Fry et al. |
| 3,131,690 | A | 5/1964 | Innis et al. |
| 3,499,437 | A | 3/1970 | Balamuth et al. |
| 3,567,847 | A | 3/1971 | Price |
| 4,343,301 | A | 8/1982 | Indech |
| 4,559,951 | A | 12/1985 | Dahl et al. |
| 4,616,231 | A | 10/1986 | Autrey et al. |
| 4,865,042 | A | 9/1989 | Umemura et al. |
| 4,879,284 | A | 11/1989 | Lang et al. |
| 5,032,123 | A | 7/1991 | Katz et al. |
| 5,041,224 | A | 8/1991 | Ohyama et al. |
| 5,082,670 | A | 1/1992 | Gage et al. |
| 5,249,575 | A | 10/1993 | Di Mino et al. |
| 5,267,152 | A | 11/1993 | Yang et al. |
| 5,290,280 | A | 3/1994 | Daikuzono et al. |

(Continued)

FOREIGN PATENT DOCUMENTS

| | | |
|---|---|---|
| CN | 1079464 A | 12/1993 |
| EP | 1 334 748 | 8/2003 |

(Continued)

OTHER PUBLICATIONS

Han et al. "Two-color, bi-directional optical voltage control of genetically-targeted neurons." CoSyne Abstract Presentation . Presented Feb. 24, 2007.*

(Continued)

*Primary Examiner* — Thaian N Ton
*Assistant Examiner* — Titilayo Moloye
(74) *Attorney, Agent, or Firm* — Bozicevic, Field & Francis LLP; Paula A. Borden

(57) ABSTRACT

Stimulation of target cells using light, e.g., in vivo or in vitro, is implemented using a variety of methods and devices. One example involves a vector for delivering a light-activated NpHR-based molecule comprising a nucleic acid sequence that codes for light-activated NpHR-based molecule and a promoter. Either a high expression of the molecule manifests a toxicity level that is less than about 75%, or the light-activated NpHR-based proteins are expressed using at least two NpHR-based molecular variants. Each of the variants characterized in being useful for expressing a light-activated NpHR-based molecule that responds to light by producing an inhibitory current to dissuade depolarization of the neuron. Other aspects and embodiments are directed to systems, methods, kits, compositions of matter and molecules for ion pumps or for controlling inhibitory currents in a cell (e.g., in in vivo and in vitro environments).

12 Claims, 20 Drawing Sheets

(56) References Cited

U.S. PATENT DOCUMENTS

| | | |
|---|---|---|
| 5,330,515 A | 7/1994 | Rutecki et al. |
| 5,382,516 A | 1/1995 | Bush |
| 5,445,608 A | 8/1995 | Chen et al. |
| 5,460,950 A | 10/1995 | Barr et al. |
| 5,460,954 A | 10/1995 | Lee et al. |
| 5,470,307 A | 11/1995 | Lindall |
| 5,495,541 A | 2/1996 | Murray et al. |
| 5,520,188 A | 5/1996 | Hennige et al. |
| 5,527,695 A | 6/1996 | Hodges et al. |
| 5,550,316 A | 8/1996 | Mintz |
| 5,641,650 A | 6/1997 | Turner et al. |
| 5,703,985 A | 12/1997 | Owyang et al. |
| 5,722,426 A | 3/1998 | Kolff |
| 5,738,625 A | 4/1998 | Gluck |
| 5,739,273 A | 4/1998 | Engelman et al. |
| 5,741,316 A | 4/1998 | Chen et al. |
| 5,755,750 A | 5/1998 | Petruska et al. |
| 5,756,351 A | 5/1998 | Isacoff et al. |
| 5,782,896 A | 7/1998 | Chen et al. |
| 5,795,581 A | 8/1998 | Segalman et al. |
| 5,807,285 A | 9/1998 | Vaitekunas et al. |
| 5,816,256 A | 10/1998 | Kissinger et al. |
| 5,898,058 A | 4/1999 | Nichols |
| 5,939,320 A | 8/1999 | Littman et al. |
| 6,057,114 A | 5/2000 | Akong et al. |
| 6,134,474 A | 10/2000 | Fischell et al. |
| 6,161,045 A | 12/2000 | Fischell et al. |
| 6,253,109 B1 | 6/2001 | Gielen |
| 6,303,362 B1 | 10/2001 | Kay et al. |
| 6,334,846 B1 | 1/2002 | Ishibashi et al. |
| 6,336,904 B1 | 1/2002 | Nikolchev |
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller et al. |
| 6,597,954 B1 | 7/2003 | Pless et al. |
| 6,609,020 B2 | 8/2003 | Gill |
| 6,615,080 B1 | 9/2003 | Unsworth et al. |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,721,603 B2 | 4/2004 | Zabara et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,808,873 B2 | 10/2004 | Murphy et al. |
| 6,810,285 B2 | 10/2004 | Pless et al. |
| 6,889,085 B2 | 5/2005 | Dawson |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et al. |
| 7,220,240 B2 | 5/2007 | Struys et al. |
| 7,298,143 B2 | 11/2007 | Jaermann et al. |
| 7,313,442 B2 | 12/2007 | Velasco et al. |
| 7,603,174 B2 | 10/2009 | De Ridder |
| 7,610,100 B2 | 10/2009 | Jaax et al. |
| 7,613,520 B2 | 11/2009 | De Ridder |
| 7,686,839 B2 | 3/2010 | Parker |
| 7,824,869 B2 | 11/2010 | Hegemann et al. |
| 7,988,688 B2 | 8/2011 | Webb et al. |
| 8,386,312 B2 | 2/2013 | Pradeep et al. |
| 8,398,692 B2 | 3/2013 | Deisseroth et al. |
| 8,401,609 B2 | 3/2013 | Deisseroth et al. |
| 8,696,722 B2 | 4/2014 | Deisseroth et al. |
| 8,815,582 B2 | 8/2014 | Deisseroth et al. |
| 8,906,360 B2 | 12/2014 | Deisseroth et al. |
| 2002/0094516 A1 | 7/2002 | Calos et al. |
| 2002/0155173 A1 | 10/2002 | Chopp et al. |
| 2002/0164577 A1 | 11/2002 | Tsien et al. |
| 2003/0009103 A1 | 1/2003 | Yuste et al. |
| 2003/0026784 A1 | 2/2003 | Koch et al. |
| 2003/0040080 A1 | 2/2003 | Miesenbock et al. |
| 2003/0050258 A1 | 3/2003 | Calos |
| 2003/0088060 A1 | 5/2003 | Benjamin et al. |
| 2003/0097122 A1 | 5/2003 | Ganz et al. |
| 2003/0104512 A1 | 6/2003 | Freeman et al. |
| 2003/0125719 A1 | 7/2003 | Furnish |
| 2003/0204135 A1 | 10/2003 | Bystritsky |
| 2003/0232339 A1 | 12/2003 | Shu et al. |
| 2004/0023203 A1* | 2/2004 | Miesenbock et al. ............. 435/4 |
| 2004/0034882 A1 | 2/2004 | Vale et al. |
| 2004/0039312 A1 | 2/2004 | Hillstead et al. |
| 2004/0068202 A1 | 4/2004 | Hansson et al. |
| 2004/0073278 A1 | 4/2004 | Pachys |
| 2004/0076613 A1 | 4/2004 | Mazarakis et al. |
| 2004/0122475 A1 | 6/2004 | Myrick et al. |
| 2004/0203152 A1 | 10/2004 | Calos |
| 2005/0058987 A1 | 3/2005 | Shi et al. |
| 2005/0088177 A1 | 4/2005 | Schreck et al. |
| 2005/0107753 A1 | 5/2005 | Rezai et al. |
| 2005/0119315 A1 | 6/2005 | Fedida et al. |
| 2005/0124897 A1 | 6/2005 | Chopra |
| 2005/0143295 A1 | 6/2005 | Walker et al. |
| 2005/0143790 A1 | 6/2005 | Kipke et al. |
| 2005/0153885 A1 | 7/2005 | Yun et al. |
| 2005/0197679 A1 | 9/2005 | Dawson |
| 2005/0202398 A1 | 9/2005 | Hegemann et al. |
| 2005/0215764 A1 | 9/2005 | Tuszynski et al. |
| 2005/0240127 A1 | 10/2005 | Seip et al. |
| 2005/0267011 A1 | 12/2005 | Deisseroth et al. |
| 2005/0267454 A1 | 12/2005 | Hissong et al. |
| 2006/0025756 A1 | 2/2006 | Francischelli et al. |
| 2006/0034943 A1 | 2/2006 | Tuszynski |
| 2006/0057192 A1 | 3/2006 | Kane |
| 2006/0057614 A1* | 3/2006 | Heintz ............................. 435/6 |
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0106543 A1 | 5/2006 | Deco et al. |
| 2006/0155348 A1 | 7/2006 | deCharms |
| 2006/0161227 A1 | 7/2006 | Walsh et al. |
| 2006/0184069 A1 | 8/2006 | Vaitekunas |
| 2006/0190044 A1 | 8/2006 | Libbus et al. |
| 2006/0206172 A1 | 9/2006 | DiMauro et al. |
| 2006/0216689 A1 | 9/2006 | Maher et al. |
| 2006/0236525 A1 | 10/2006 | Sliwa et al. |
| 2006/0241697 A1 | 10/2006 | Libbus et al. |
| 2006/0253177 A1 | 11/2006 | Taboada et al. |
| 2006/0271024 A1 | 11/2006 | Gertner et al. |
| 2007/0031924 A1 | 2/2007 | Li et al. |
| 2007/0054319 A1 | 3/2007 | Boyden et al. |
| 2007/0060915 A1 | 3/2007 | Kucklick |
| 2007/0135875 A1 | 6/2007 | Demarais et al. |
| 2007/0156180 A1 | 7/2007 | Jaax et al. |
| 2007/0191906 A1 | 8/2007 | Iyer et al. |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1 | 11/2007 | Hildebrand |
| 2007/0261127 A1 | 11/2007 | Boyden et al. |
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |

(56) References Cited

U.S. PATENT DOCUMENTS

| | | |
|---|---|---|
| 2008/0033569 A1 | 2/2008 | Ferren et al. |
| 2008/0046053 A1 | 2/2008 | Wagner et al. |
| 2008/0050770 A1 | 2/2008 | Zhang et al. |
| 2008/0051673 A1 | 2/2008 | Kong et al. |
| 2008/0060088 A1 | 3/2008 | Shin et al. |
| 2008/0065158 A1 | 3/2008 | Ben-Ezra et al. |
| 2008/0065183 A1 | 3/2008 | Whitehurst et al. |
| 2008/0077200 A1 | 3/2008 | Bendett et al. |
| 2008/0085265 A1 | 4/2008 | Schneider et al. |
| 2008/0103551 A1 | 5/2008 | Masoud et al. |
| 2008/0119421 A1 | 5/2008 | Tuszynski et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0176076 A1 | 7/2008 | Van Veggel et al. |
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2008/0228244 A1 | 9/2008 | Pakhomov et al. |
| 2008/0262411 A1 | 10/2008 | Dobak |
| 2008/0287821 A1 | 11/2008 | Jung et al. |
| 2008/0290318 A1 | 11/2008 | Van Veggel et al. |
| 2009/0030930 A1 | 1/2009 | Pradeep et al. |
| 2009/0088680 A1 | 4/2009 | Deisseroth et al. |
| 2009/0093403 A1 | 4/2009 | Zhang et al. |
| 2009/0099038 A1 | 4/2009 | Deisseroth et al. |
| 2009/0112133 A1 | 4/2009 | Deisseroth et al. |
| 2009/0118800 A1 | 5/2009 | Deisseroth et al. |
| 2009/0148861 A1 | 6/2009 | Pegan et al. |
| 2009/0157145 A1 | 6/2009 | Cauller |
| 2009/0131837 A1 | 10/2009 | Zhang et al. |
| 2009/0254134 A1 | 10/2009 | Nikolov et al. |
| 2009/0268511 A1 | 10/2009 | Birge et al. |
| 2009/0319008 A1 | 12/2009 | Mayer |
| 2009/0326603 A1 | 12/2009 | Boggs |
| 2010/0009444 A1 | 1/2010 | Herlitze et al. |
| 2010/0016783 A1 | 1/2010 | Bourke et al. |
| 2010/0145418 A1 | 6/2010 | Zhang et al. |
| 2010/0146645 A1 | 6/2010 | Vasar et al. |
| 2010/0190229 A1 | 7/2010 | Zhang et al. |
| 2010/0234273 A1 | 9/2010 | Deisseroth et al. |
| 2011/0021970 A1 | 1/2011 | Vo-Dinh et al. |
| 2011/0092800 A1 | 4/2011 | Yoo et al. |
| 2011/0105998 A1 | 5/2011 | Zhang et al. |
| 2011/0112179 A1 | 5/2011 | Deisseroth et al. |
| 2011/0112463 A1 | 5/2011 | Silver et al. |
| 2011/0125077 A1 | 5/2011 | Denison et al. |
| 2011/0125078 A1 | 5/2011 | Denison et al. |
| 2011/0159562 A1 | 6/2011 | Deisseroth et al. |
| 2011/0165681 A1 | 7/2011 | Boyden et al. |
| 2011/0166632 A1 | 7/2011 | Delp et al. |
| 2011/0172653 A1 | 7/2011 | Deisseroth et al. |
| 2011/0301529 A1 | 12/2011 | Zhang et al. |
| 2011/0311489 A1 | 12/2011 | Deisseroth et al. |
| 2012/0093772 A1 | 4/2012 | Horsager et al. |
| 2012/0165904 A1 | 6/2012 | Deisseroth et al. |
| 2012/0253261 A1 | 10/2012 | Poletto et al. |
| 2013/0019325 A1 | 1/2013 | Deisseroth et al. |
| 2013/0030275 A1 | 1/2013 | Seymour et al. |
| 2013/0144359 A1 | 6/2013 | Kishawi et al. |
| 2015/0112411 A1 | 4/2015 | Beckman et al. |

FOREIGN PATENT DOCUMENTS

| | | |
|---|---|---|
| EP | 1873566 | 1/2008 |
| JP | 2006-295350 | 10/1994 |
| JP | 2010227537 A | 10/2010 |
| WO | WO 96/32076 | 10/1996 |
| WO | WO 00/27293 | 5/2000 |
| WO | WO 2001-025466 | 4/2001 |
| WO | WO 03/106486 A2 | 2/2003 |
| WO | WO 03-040323 | 5/2003 |
| WO | WO 03-084994 | 10/2003 |
| WO | WO 03-102156 | 12/2003 |
| WO | WO 2004/033647 | 4/2004 |
| WO | WO 2007-024391 | 3/2007 |
| WO | WO 2007-131180 | 11/2007 |
| WO | WO 2008/086470 | 7/2008 |
| WO | WO 2008/106694 | 9/2008 |
| WO | WO 2009/025819 | 2/2009 |
| WO | WO2009/119782 | 10/2009 |
| WO | WO 2009-131837 | 10/2009 |
| WO | WO 2010/006049 | 1/2010 |
| WO | WO 2010/011404 A3 | 1/2010 |
| WO | WO 2010/056970 | 5/2010 |
| WO | WO-2010123993 | 10/2010 |
| WO | WO 2011/005978 | 1/2011 |
| WO | WO 2011/066320 A3 | 6/2011 |
| WO | WO 2011-116238 A2 | 9/2011 |
| WO | WO 2011/127088 A3 | 10/2011 |
| WO | WO 2012/032103 | 3/2012 |
| WO | WO 2012/061676 | 5/2012 |
| WO | WO2012/061681 | 5/2012 |
| WO | WO2012/061684 | 5/2012 |
| WO | WO2012/061688 | 5/2012 |
| WO | WO2012/061690 | 5/2012 |
| WO | WO 2012/061741 | 5/2012 |
| WO | WO 2012/061744 | 5/2012 |
| WO | 2012/106407 | 8/2012 |
| WO | WO 2012/134704 A2 | 10/2012 |
| WO | WO 2013/016486 | 1/2013 |
| WO | WO 2013/126521 | 8/2013 |
| WO | WO 2013/142196 | 9/2013 |

OTHER PUBLICATIONS

Ma et al. "Role of ER export signals in controlling surface potassium channel numbers." Science. (Jan. 12, 2001);291(5502):pp. 316-319.*

Li et al. "Surface Expression of Kv1 Channels is Governed by a C-terminal Motif." The Journal of Biological Chemistry(Apr. 2000); 275: pp. 11597-11602.*

Hutsler et al. "Acetylcholinesterase staining in human auditory and language cortices: regional variation of structural features." Cereb Cortex. (Mar.-Apr. 1996);6(2):pp. 260-270.*

Lonnerberg et al. "Regulatory region in choline acetyltransferase gene directs developmental and tissue-specific expression in transgenic mice." Proc Natl Acad Sci U S A. (Apr. 25, 1995);92(9):pp. 4046-4050.*

Arenkiel, et al. "In vivo light-induced activation of neural circuitry in transgenic mice expressing Channelrhodopsin-2", Neuron, 2007, 54:205-218.

Milella et al. "Opposite roles of dopamine and orexin in quinpirole-induced excessive drinking: a rat model of psychotic polydipsia" Psychopharmacology, 2010, 211:355-366.

Marin, et al., The Amino Terminus of the Fourth Cytoplasmic Loop of Rhodopsin Modulates Rhodopsin-Transduction Interaction, The Journal of Biological Chemistry, 2000, vol. 275, pp. 1930-1936.

Xiong et al., "Interregional connectivity to primary motor cortex revealed using MRI resting state images", Hum Brain Mapp, 1999, 8(2-3):151-156.

Hikida et al., "Increased sensitivity to cocaine by cholinergic cell ablation in nucleus accumbens", PNAS, Nov. 2001, 98(23): 13351-13354.

Hikida et al., "Acetylcholine enhancement in the nucleus accumbens prevents addictive behaviors of cocaine and morphine", PNAS, May 2003, 100(10):6169-6173.

Kitabatake et al., "Impairment of reward-related learning by cholinergic cell ablation in the striatum", PNAS, Jun. 2003, 100(13):7965-7970.

Tamai, "Progress in Pathogenesis and Therapeutic Research in Retinitis Pigmentosa and Age Related Macular Degeneration", Nippon Ganka Gakkai Zasshi, vol. 108, No. 12, Dec. 2004, pp. 750-769.

Berke, et al. "Addiction, Dopamine, and the Molecular Mechanisms of Memory", Molecular Plasticity, 2000, vol. 25: pp. 515-532.

Goshen et al. "Dynamics of Retrieval Strategies for Remote Memories", Cell, 2011, vol. 147: pp. 678-589.

Jimenez S.A & Maren S. et al/"Nuclear disconnection within the amygdala reveals adirect pathway to fear", Learning Memory, 2009, vol. 16: pp. 766-768.

(56) References Cited

OTHER PUBLICATIONS

Ehrlich I. et al. "Amygdala inhibitory circuits and the control of fear memory", Neuron, 2009. Friedrich Meischer Institute, vol. 62: pp. 757-771.

Berndt et al. "Bi-stable neural state switches", Nature Neuroscience, 2009, vol. 12, No. 2: pp. 229-234.

Simmons et al. "Localization and function of NK3 subtype Tachykinin receptors of layer pyramidal neurons of the guinea-pig medial prefrontal cortex", Neuroscience, 2008, vol. 156, No. 4: pp. 987-994.

Fox et al., "A gene neuron expression fingerprint of C. elegans embryonic motor neurons", BMC Genomics, 2005, 6(42):1-23.

Nonet, "Visualization of synaptic specializations in live C. elegans with synaptic vesicle protein-GFP fusions", J. Neurosci. Methods, 1999, 89:33-40.

Synapse, Chapter 13, http://michaeldmann.net/mann13.html, downloaded Apr. 2014.

Cazillis et al., "VIP and PACAP induce selective neuronal differentiation of mouse embryonic stem cells", Eur J Neurosci, 2004, 19(4):798-808.

Morelli et al., "Neuronal and glial cell type-specific promoters within adenovirus recombinants restrict the expression of the apoptosis-inducing molecule Fas ligand to predetermined brain cell types, and abolish peripheral liver toxicity", Journal of General Virology, 1999, 80:571-583.

Aebischer, et al. "Long-Term Cross-Species Brain Transplantation of a Polymer-Encapsulated Dopamine-Secreting Cell Line", Experimental Neurology, 1991, vol. 111, pp. 269-275.

Ahmad, et al. "The Drosophila rhodopsin cytoplasmic tail domain is required for maintenance of rhabdomere structure." The FASEB Journal, 2007, vol. 21, p. 449-455.

Airan, et al., "Temporally Precise in vivo Control of Intracellular Signaling", 2009, Nature, vol. 458, No. 7241, pp. 1025-1029.

Akirav, et al. "The role of the medial prefrontal cortex-amygdala circuit in stress effects on the extinction of fear", Neural Plasticity, 2007: vol. 2007 Article ID:30873, pp. 1-11.

Ang, et at. "Hippocampal CA1 Circuitry Dynamically Gates Direct Cortical Inputs Preferentially at Theta Frequencies." The Journal of Neurosurgery, 2005, vol. 25, No. 42, pp. 9567-9580.

Araki, et al. "Site-Directed Integration of the cre Gene Mediated by Cre Recombinase Using a Combination of Mutant lox Sites", Nucleic Acids Research, 2002, vol. 30, No. 19, pp. 1-8.

Aravanis, et al. "An optical neural interface: in vivo control of rodent motor cortex with integrated fiberoptic and optogenetic technology," J. Neural. Eng., 2007, vol. 4(3):S143-S156.

Argos, et al. "The integrase family of site-specific recombinases: regional similarities and global diversity", The EMBO Journal, 1986, vol. 5, No. 2, pp. 433-440.

Bamberg et al. "Light-driven proton or chloride pumping by halorhodopsin." Proc. Natl. Academy Science USA, 1993, vol. 90, No. 2, p. 639-643.

Banghart, et al. "Light-activated ion channels for remote control of neuronal firing". Nature Neuroscience, 2004, vol. 7, No. 12 pp. 1381-1386.

Basil et al. "Is There Evidence for Effectiveness of Transcranial Magnetic Stimulation in the Treatment of Psychiatric Disorders?" Psychiatry, 2005, pp. 64-69.

Bebbington et al., "The use of vectors based on gene amplification for the expression of cloned genes in mammalian cells in DNA cloning" vol. 3, Academic Press, New York, 1987.

Benabid "Future strategies to restore brain functions," Conference proceedings from Medicine Meets Millennium: World Congress of Medicine and Health, 2000, 6 pages.

Benoist et al. "In vivo sequence requirements of the SV40 early promotor region" Nature (London), 1981, vol. 290(5804): pp. 304-310.

Berges et al., "Transduction of Brain by Herpes Simplex Virus Vectors", Molecular Therapy, 2007, vol. 15, No. 1: pp. 20-29.

Berridge et al., "The Versatility and Universality of Calcium Signaling", Nature Reviews: Molecular Cell Biology, 2000, vol. 1: pp. 11-21.

Bocquet et al. "A prokaryotic proton-gated ion channel from the nicotinic acetylcholine receptor family." Nature Letters, 2007, vol. 445, p. 116-119.

Boyden, et al. "Millisecond-timescale, genetically targeted optical control of neural activity" Nature Neuroscience, 2005, vol. 8, No. 9: pp. 1263-1268.

Bi, et al. "Ectopic Expression of a Microbial-Type Rhodopsin Restores Visual Responses in Mice with Photoreceptor Degeneration", Neuron, 2006, vol. 50, No. 1: pp. 23-33.

Bi, et al. "Synaptic Modifications in Cultured Hippocampal Neurons: Dependence on Spike Timing, Synaptic Strength, and Postsynaptic Cell Type", Journal of Neuroscience, 1998, vol. 18, No. 24: pp. 10464-1 0472.

Blomer et al., "Highly Efficient and Sustained Gene Transfer in Adult Neurons with Lentivirus Vector", Journal of Virology,1997, vol. 71, No. 9: pp. 6641-6649.

Braun, "Two Light-activated Conductances in the Eye of the Green Alga Volvox carteri", 1999, Biophys J., vol. 76, No. 3, pp. 1668-1678.

Brinton, et al. "Preclinical analyses of the therapeutic potential of allopregnanolone to promote neurogenesis in vitro and in vivo in transgenic mouse model of Alzheimer's disease." Current Alzheimer Research, 2006, vol. 3, No. 1: pp. 11-17.

Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.

Brown, et al. "Long-term potentiation induced by θ frequency stimulation is regulated by a protein phosphate-operated gate." The Journal of Neuroscience, 2000, vol. 20, No. 21, pp. 7880-7887.

Callaway, et al. "Photostimulation using caged glutamate reveals functional circuitry in living brain slices", Proc. Natl. Acad. Sci. USA., 1993, vol. 90: pp. 7661-7665.

Campagnola et al. "Fiber-coupled light-emitting diode for localized photostimulation of neurons expressing channelrhodopsin-2." Journal of Neuroscience Methods , 2008, vol. 169, Issue 1. Abstract only.

Cardin, et al. "Driving Fast spiking Cells Induces Gamma Rhythm and Controls Sensory Responses", 2009, Nature, vol. 459, vol. 7247, pp. 663-667.

Cenatiempo "Prokaryotic gene expression in vitro: transcription-translation coupled systems", Biochimie, 1986, vol. 68(4): pp. 505-515.

Claudio et al. "Nucleotide and deduced amino acid sequences of Torpedo californica acetylcholine receptor gamma subunit." PNAS USA,1983, vol. 80, p. 1111-1115.

Collingridge et al. "Inhibitory post-synaptic currents in rat hippocampal CA1 neurones." J. Physiol., 1984, vol. 356, pp. 551-564.

Covington, et al. "Antidepressant Effect of Optogenetic Stimulation of the Medial Prefrontal Cortex." Journal of Neuroscience, 2010, vol. 30(48), pp. 16082-16090.

Crouse, et al. "Expression and amplification of engineered mouse dihydrofolate reductase minigenes" Mol. Cell. Biol. , 1983, vol. 3(2): pp. 257-266.

Cucchiaro et al., "Phaseolus vulgaris leucoagglutinin (PHA-L): a neuroanatomical tracer for electron microscopic analysis of synaptic circuitry in the cat's dorsal lateral geniculate nucleus" J. Electron. Microsc. Tech., 1990, 15 (4):352-368.

Cucchiaro et al., "Electron-Microsoft Analysis of Synaptic Input from the Perigeniculate Nucleus to A-Lamine of the Lateral Geniculate Nucleus in Cats", The Journal of Comparitive Neurology, 1991, vol. 310, pp. 316-336.

Cui, et al., "Electrochemical deposition and characterization of conducting polymer polypyrrole/PSS on multichannel neural probes," Sensors and Actuators, 2001, vol. 93(1): pp. 8-18.

Date, et al. "Grafting of Encapsulated Dopamine-Secreting Cells in Parkinson's Disease: Long-Term Primate Study", Cell Transplant, 2000, vol. 9, pp. 705-709.

Dalva, et al. "Rearrangements of Synaptic Connections in Visual Cortex Revealed by Laser Photostimulation", Science, 1994,vol. 265, pp. 255-258.

(56) References Cited

OTHER PUBLICATIONS

Dederen, et al. "Retrograde neuronal tracing with cholera toxin B subunit: comparison of three different visualization methods", Histochemical Journal, 1994, vol. 26, pp. 856-862.
De Foubert et al. "Fluoxetine-Induced Change in Rat Brain Expression of Brain-Derived Neurotrophic Factor Varies Depending on Length of Treatment," Neuroscience, 2004, vol. 128, pp. 597-604.
Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.
Deisseroth et al., "Translocation of Calmodulin to the Nucleus Supports CREb Phosphorylation in Hippocampal Neurons", Nature, 1998, vol. 392, pp. 198-202.
Deisseroth et al., "Signaling from Synapse to Nucleus: the logic Behind the Mechanisms", Currrent Opinion in Neurobiology, 2003, vol. 13, pp. 354-65.
Deisseroth et al., "Excitation-neurogenesis Coupling in Adult Neural Stem/Progenitor Cells", 2004, Neuron, vol. 42, pp. 535-552.
Deisseroth "Next-generation optical technologies for illuminating genetically targeted brain circuits," The Journal of Neuroscience, 2006, vol. 26, No. 41, pp. 10380-10386.
Denk, W., et al. "Anatomical and functional imaging of neurons using 2-photon laser scanning microscopy", Journal of Neuroscience Methods, 1994, vol. 54, pp. 151-162.
Ditterich, et al. "Microstimulation of visual cortex affects the speed of perceptual decisions", 2003, Nature Neuroscience, vol. 6, No. 8, pp. 891-898.
Dittgen, et al. "Lentivirus-based genetic manipulations of cortical neurons and their optical and electrophysiological monitoring in vivo", PNAS, 2004, vol. 101, No. 52, pp. 18206-18211.
Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.
Ensell, et al. "Silicon-based microelectrodes for neurophysiology, micromachined from silicon-on-insulator wafers," Med. Biol. Eng. Comput., 2000, vol. 38, pp. 175-179.
Eisen, "Treatment of amyotrophic lateral sclerosis", Drugs Aging, 1999; vol. 14, No. 3, pp. 173-196.
Ernst, et al. "Photoactivation of Channelrhodopsin", 2008, vol. 283, No. 3, pp. 1637-1643.
Evanko "Optical excitation yin and yang" Nature Methods, 2007, 4:384.
Esposito et al. "The integrase family of tyrosine recombinases: evolution of a conserved active site domain" , Nucleic Acids Research, 1997, vol. 25, No. 18, pp. 3605-3614.
Fabian et al. "Transneuronal transport of lectins" Brain Research, 1985, vol. 344, pp. 41-48.
Falconer et al. "High-throughput screening for ion channel modulators," Journal of Biomolecular Screening, 2002, vol. 7, No. 5, pp. 460-465.
Farber, et al. "Identification of Presynaptic Neurons by Laser Photostimulation", Science, 1983, vol. 222, pp. 1025-1027.
Feng, et al. "Imaging Neuronal Subsets in Transgenic Mice Expressing Multiple Spectral Variants of GFP", Neuron, 2000, vol. 28, pp. 41-51.
Fisher, J. et al. "Spatiotemporal Activity Patterns During Respiratory Rhythmogenesis in the Rat Ventrolateral Medulla," The Journal of Neurophysiol, 2006, vol. 95, pp. 1982-1991.
Fitzsimons et al., "Promotors and Regulatory Elements that Improve Adeno-Associated Virus Transgene Expression in the Brain", 2002, Methods, vol. 28, pp. 227-236.
Foster, "Bright blue times", Nature, 2005, vol. 433, pp. 698-699.
Genbank Accession No. DQ094781 (Jan. 15, 2008).
Gelvich et al. "Contact flexible microstrip applicators (CFMA) in a range from microwaves up to short waves," IEEE Transactions on Biomedical Engineering, 2002, vol. 49, Issue 9: 1015-1023.
Gigg, et al. "Glutamatergic hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.
Gilman, et al. "Isolation of sigma-28-specific promoters from *Bacillus subtilis* DNA" Gene, 1984, vol. 32(1-2): pp. 11-20.
Glick et al. "Factors affecting the expression of foreign proteins in *Escherichia coli*", Journal of Industrial Microbiology, 1987, vol. 1(5): pp. 277-282.
Goekoop, R. et al. "Cholinergic challenge in Alzheimer patients and mild cognitive impairment differentially affects hippocampal activation-a pharmacological fMRI study." Brain, 2006, vol. 129, pp. 141-157.
Gold, et al. "Representation of a perceptual decision in developing oculomotor commands", Nature, 2000, vol. 404, pp. 390-394.
Gonzalez, et al., "Cell-Based Assays and Instrumentation for Screening Ion-Channel Targets", DDT, 1999, vol. 4, No. 9, pp. 431439.
Gordon, et al. "Regulation of Thy-1 Gene Expression in Transgenic Mice", Cell, 1987, vol. 50, pp. 445-452.
Gorelova et al., "The course of neural projection from the prefrontal cortex to the nucleus accumbens in the rat ", Neuroscience, 1997, vol. 76, No. 3, pp. 689-706.
Gottesman et al."Bacterial regulation: global regulatory networks," Ann. Rev. Genet. , 1984, vol. 18, pp. 415-441.
Gradinaru, et al. "ENpHR: a Natronomonas Halorhodopsin Enhanced for Optogenetic Applications", 2008, Brain Cell Biol., vol. 36 (1-4), pp. 129-139.
Greenberg, et al. "Three-year outcomes in deep brain stimulation for highly resistant obsessive-compulsive disorder," Neuropsychopharmacology, 2006, vol. 31, pp. 2384-2393.
Gregory, et al. "Integration site for *Streptomyces* phage φBT1 and development of site-specific integrating vectors", Journal of Bacteriology, 2003, vol. 185, No. 17, pp. 5320-5323.
Groth et al. "Phage integrases: biology and applications," Journal of Molecular Biology, 2004, vol. 335, pp. 667-678.
Groth, et al. "A phage integrase directs efficient site-specific integration in human cells", PNAS, 2000, vol. 97, No. 11, pp. 5995-6000.
Guatteo, et al. "Temperature sensitivity of dopaminergic neurons of the substantia nigra pars compacta: Involvement of transient receptor potential channels," Journal of Neurophysiol. , 2005, vol. 94, pp. 3069-3080.
Gulick, et al. "Transfection using DEAE-Dextran" Supplement 40, Current Protocols in Molecular Biology, 1997, Supplement 40, 9.2.1-9.2.10.
Gur et al., "A Dissociation Between Brain Activity and Perception: Chromatically Opponent Cortical Neurons Signal Chromatic Flicker that is not Perceived", Vision Research, 1997, vol. 37, No. 4, pp. 377-382.
Hallet et al. "Transposition and site-specific recombination: adapting DNA cut-and-paste mechanisms to a variety of genetic rearrangements," FEMS Microbiology Reviews, 1997, vol. 21, No. 2, pp. 157-178.
Hamer, et al. "Regulation In Vivo of a cloned mammalian gene: cadmium induces the transcription of a mouse metallothionein gene in SV40 vectors," Journal of Molecular Applied Genetics, 1982, vol. 1, No. 4, pp. 273-288.
Hausser, et al. "Tonic Synaptic Inhibition Modulates Neuronal Output Pattern and Spatiotemporal Synaptic Integration", Neuron, 1997, vol. 19, pp. 665-678.
Hegemann et al., "All-trans Retinal Constitutes the Functional Chromophore in *Chlamydomonas* rhodopsin", Biophys. J. , 1991, vol. 60, pp. 1477-1489.
Herlitze, et al., "New Optical Tools for Controlling Neuronal Activity", 2007, Curr Opin Neurobiol, vol. 17, No. 1, pp. 87-94.
Herry, et al. "Switching on and off fear by distinct neuronal circuits," Nature, 2008, vol. 454, pp. 600-606.
Hildebrandt et al, "Bacteriorhodopsin expressed in *Schizosaccharomyces pombe* pumps protons through the plasma membrane, " PNAS, 1993, vol. 90, pp. 3578-3582.
Hirase, et al. "Multiphoton stimulation of neurons", J Neurobiol, 2002, vol. 51, No. 3: pp. 237-247.
Hodaie, et al., "Chronic Anterior Thalamus Stimulation for Intractable Epilepsy," Epilepsia, 2002, vol. 43, pp. 603-608.

(56) References Cited

OTHER PUBLICATIONS

Hoffman et al., "K+ Channel Regulation of Signal Propagation in Dendrites of Hippocampal Pyramidal Neurons", 1997, Nature, vol. 387: pp. 869-874.

Hosokawa, T. et al. "Imaging spatio-temporal patterns of long-term potentiation in mouse hippocampus." Philos. Trans. R. Soc. Lond. B., 2003, vol. 358, pp. 689-693.

Hynynen, et al. "Clinical applications of focused ultrasound-The brain." Int. J. Hyperthermia, 2007, vol. 23, No. 2: pp. 193-202.

International Search Report for International Application No. PCT/US2009/053474, dated Oct. 8, 2009.

Isenberg et al. "Cloning of a Putative Neuronal Nicotinic Aceylcholine Receptor Subunit," Journal of Neurochemistry, 1989, pp. 988-991.

Jekely, "Evolution of Phototaxis", 2009, Phil. Trans. R. Soc. B, vol. 364, pp. 2795-2808.

Johansen, et al., "Optical Activation of Lateral Amygdala Pyramidal Cells Instructs Associative Fear Learning", 2010, PNAS, vol. 107, No. 28, pp. 12692-12697.

Johnston et al. "Isolation of the yeast regulatory gene *GAL4* and analysis of its dosage effects on the galactose/melibiose regulon," PNAS, 1982, vol. 79, pp. 6971-6975.

Kandel, E.R., et al. "Electrophysiology of Hippocampal Neurons: I. Sequential Invasion and Synaptic Organization," J Neurophysiol, 1961, vol. 24, pp. 225-242.

Kandel, E.R., et al. "Electrophysiology of Hippocampal Neurons: II. After-Potentials and Repetitive Firing", J Neurophysiol., 1961, vol. 24, pp. 243-259.

Karreman et al. "On the use of double FLP recognition targets (FRTs) in the LTR of retroviruses for the construction of high producer cell lines", Nucleic Acids Research, 1996, vol. 24, No. 9: pp. 1616-1624.

Kato et al. "Present and future status of noninvasive selective deep heating using RF in hyperthermia." Med & Biol. Eng. & Comput 31 Supp: S2-11, 1993. Abstract. p. S2 only.

Katz, et al. "Scanning laser photostimulation: a new approach for analyzing brain circuits," Journal of Neuroscience Methods, 1994, vol. 54, pp. 205-218.

Khodakaramian, et al. "Expression of Cre Recombinase during Transient Phage Infection Permits Efficient Marker Removal in *Streptomyces*," Nucleic Acids Research, 2006, vol. 34, No. 3:e20, pp. 1-5.

Khossravani et al., "Voltage-Gated Calcium Channels and Idiopathic Generalized Epilepsies", Physiol. Rev., 2006, vol. 86: pp. 941-966.

Kianianmomeni, et al. "Channelrhodopsins of Volvox carted are Photochromic Proteins that are Specifically Expressed in Somatic Cells under Control of Light, Temperature, and the Sex Inducer", 2009, Plant Physiology, vol. 151, No. 1, pp. 347-366.

Kim et al., "Light-Driven Activation of β2-Adrenergic Receptor Signaling by a Chimeric Rhodopsin Containing the β2-Adrenergic Receptor Cytoplasmic Loops," Biochemistry, 2005, vol. 44, No. 7, pp. 2284-2292.

Kingston et al. "Transfection of DNA into Eukaryotic Cells," Supplement 63, Current Protocols in Molecular Biology, 1996, 9.1.1-9.1.11, 11 pages.

Kingston et al. "Transfection and Expression of Cloned DNA," Supplement 31, Current Protocols in Immunology, 1999, 10.13.1-1 0.13.9.

Kita, H. et al. "Effects of dopamine agonists and antagonists on optical responses evoked in rat frontal cortex slices after stimulation of the subcortical white matter," Exp. Brain Research, 1999, vol. 125, pp. 383-388.

Kitayama, et al. "Regulation of neuronal differentiation by *N*-methyl-D-aspartate receptors expressed in neural progenitor cells isolated from adult mouse hippocampus," Journal of Neurosci Research, 2004, vol. 76, No. 5: pp. 599-612.

Klausberger, et al. "Brain-state- and cell-type-specific firing of hippocampal interneurons in vivo", Nature, 2003, vol. 421: pp. 844-848.

Kocsis et al., "Regenerating Mammalian Nerve Fibres: Changes in Action Potential Wavefrom and Firing Characteristics Following Blockage of Potassium Conductance", 1982, Proc. R. Soc. Lond., vol. B 217: pp. 77-87.

Knopfel, et al. "Optical Probin of Neuronal Circuit Dynamics: Gentically Encoded Versus Classical Fluorescent Sensors", 2006, Trends Neurosci, vol. 29, No. 3, pp. 160-166.

Kuhlman et al. (2008) "High-Resolution Labeling and Functional Manipulation of Specific Neuron Types in Mouse Brain by Cre-Activated Viral Gene Expression" PLoS One, 2005, vol. 3, No. 4, pp. 1-11.

Kunkler, P. et at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.

Landy, A. "Mechanistic and structural complexity in the site-specific recombination pathways of Int and FLP", Current Opinion in Genetics and Development, 1993, vol. 3, pp. 699-707.

Lee et al. "Sterotactic Injection of Adenoviral Vectors that Target Gene Expression to Specific Pituitary Cell Types: Implications for Gene Therapy", Neurosurgery, 2000, vol. 46, No. 6: pp. 1461-1469.

Lee et al., "Potassium Channel Gone Therapy Can Prevent Neuron Deatch Resulting from Necrotic and Apoptotic Insults", Journal of Neurochemistry, 2003, vol. 85: pp. 1079-1088.

Levitan et al. "Surface Expression of Kv1 Voltage-Gated K+ Channels Is Governed by a C-terminal Motif," Trends Cardiovasc. Med., 2000, vol. 10, No. 7, pp. 317-320.

Li et al. "Fast noninvasive activation and inhibition of neural and network activity by vertebrate rhodopsin and green algae channelrhodopsin." PNAS, 2005, vol. 102, No. 49, p. 17816-17821.

Lim et al., "A Novel Targeting Signal for Proximal Clustering of the Kv2.1 K+ Channel in Hippocampal Neurons", Neuron, 2000, vol. 25: pp. 385-397.

Lima, et al. "Remote Control of Behavior through Genetically Targeted Photostimulation of Neurons" Cell, 2005, vol. 121: pp. 141-152.

Liman, et al. "Subunit Stoichiometry of a Mammalian K+ Channel Determined by Construction of Multimeric cDNAs," Neuron, 1992, vol. 9, pp. 861-871.

Louis et al. "Cloning and sequencing of the cellular-viral junctions from the human adenovirus type 5 transformed 293 cell line," Virology, 1997, vol. 233, pp. 423-429.

Luecke, et al. "Structural Changes in Bacteriorhodopsin During Ion Transport at 2 Angstrom Resolution," Science, 1999, vol. 286, pp. 255-260.

Lyznik, et al. "FLP-mediated recombination of *FRT* sites in the maize genome," Nucleic Acids Research, 1996, vol. 24, No. 19: pp. 3784-3789.

Ma et al. "Role of ER Export Signals in Controlling Surface Potassium Channel Numbers," Science, 2001, vol. 291, pp. 316-319.

Mann et at. "Perisomatic Feedback Inhibition Underlies Cholinergically Induced Fast Network Oscillations in the Rat Hippocampus in Vitro," Neuron, 2005, vol. 45, 2005, pp. 105-117.

Mattson, "Apoptosis in Neurodegenerative Disorders", Nature Reviews, 2000, vol. 1: pp. 120-129.

Mayberg et al. "Deep Brain Stimulation for Treatment-Resistant Depression," Focus, 2008, vol. VI, No. 1, pp. 143-154.

McAllister, "Cellular and Molecular Mechanisms of Dendrite Growth", 2000, Cereb Cortex, vol. 10, No. 10, pp. 963-973.

McKnight "Functional relationships between transcriptional control signals of the thymidine kinase gene of herpes simplex virus", Cell, 1982, vol. 31 pp. 355-365.

Melyan, Z., et al. "Addition of human melanopsin renders mammalian cells Photoresponsive", Nature, 2005, vol. 433: pp. 741-745.

Mermelstein, et al. "Critical Dependence of cAMP Response Element-Binding Protein Phosphorylation on L-Type Calcium Channels Supports a Selective Response to EPSPs in Preference to Action Potentials", The Journal of Neuroscience, 2000, vol. 20, No. 1, pp. 266-273.

Meyer, et al. "High density interconnects and flexible hybrid assemblies for active biomedical implants," IEEE Transactions on Advanced Packaging, 2001, vol. 24, No. 3, pp. 366-372.

(56) References Cited

OTHER PUBLICATIONS

Monje et al., "Irradiation Induces Neural Precursor-Cell Dysfunction", Natural Medicine, 2002, vol. 8, No. 9, pp. 955-962.
Mortensen et al. "Selection of Transfected Mammalian Cells," Supplement 86, Current Protocols in Molecular Biology, 1997, 9.5.1-09.5.19.
Nacher, et al. "NMDA receptor antagonist treatment increases the production of newneurons in the aged rat hippocampus", Neurobiology of Aging, 2003,vol. 24, No. 2: pp. 273-284.
Nagel et al. "Functional Expression of Bacteriorhodopsin in Oocytes Allows Direct Measurement of Voltage Dependence of Light Induced H+ Pumping," FEBS Letters, 1995, vol. 377, pp. 263-266.
Nagel, et al. "Channelrhodopsin-I: a light-gated proton channel in green algae", Science, 2002, vol. 296: pp. 2395-2398.
Nagel, et al. "Channelrhodopsin-2, a directly light-gated cation-selective membrane channel", PNAS, 2003, vol. 100, No. 24: pp. 13940-13945.
Nakagami, et al. "Optical Recording of Trisynaptic Pathway in Rat Hippocampal Slices with a Voltage-Sensitive Dye" Neuroscience, 1997, vol. 81, No. 1, pp. 1-8.
Naqvi, et al. "Damage to the insula disrupts addiction to cigarette smoking," Science; 2007, vol. 315 pp. 531-534.
Natochin, et al. "Probing rhodopsin-transducin interaction using *Drosophila* Rh1-bovine rhodopsin chimeras," Vision Res., 2006, vol. 46, No. 27: pp. 4575-4581.
Nirenberg, et al. "The Light Response of Retinal Ganglion Cells is Truncated by a Displaced Amacrine Circuit", Neuron, 1997, vol. 18: pp. 637-650.
Nunes-Duby, et al. "Similarities and differences among 105 members of the Int family of site-specific recombinases", Nucleic Acids Research, 1998, vol. 26, No. 2: pp. 391-406.
O'Gorman et al. "Recombinase-mediated gene activation and site-specific integration in mammalian cells", Science, 1991, 251(4999): pp. 1351-1355.
Olivares (2001) "Phage R4 integrase mediates site-specific integration in human cells", Gene, 2001, vol. 278, pp. 167-176.
Ory, et al. "A stable human-derived packaging cell line for production of high titer retrovirus/vesicular stomatitis virus G pseudotypes," PNAS, 1996, vol. 93: pp. 11400-11406.
Palmer et al., "The Adult Rat Hippocampus Contains Primordial Neural Stem Cells", Molecular and Cellular Neuroscience, 1997, vol. 8, pp. 389-404.
Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.
Pan et al. "Functional Expression of a Directly Light-Gated Membrane Channel in Mammalian Retinal Neurons: A Potential Strategy for Restoring Light Sensitivity to the Retina After Photoreceptor Degeneration," Investigative Opthalmology & Visual Science, 2005, 46 E-Abstract 4631. Abstract only.
Panda, et al. "Illumination of the Melanopsin Signaling Pathway", Science, 2005, vol. 307: pp. 600-604.
Pape, et al., "Plastic Synaptic Networks of the Amygdala for the Acquisition, Expression, and Extinction of Conditioned Fear", 2010, Physiol Rev, vol. 90, pp. 419-463.
Paulhe et al. "Specific Endoplasmic Reticulum Export Signal Drives Transport of Stem Cell Factor (Kitl) to the Cell Surface," the Journal of Biological Chemistry, 2004, vol. 279, No. 53, p. 55545-55555.
Pear "Transient Transfection Methods for Preparation of High-Titer Retroviral Supernatants" Supplement 68, Current Protocols in Molecular Biology, 1996, 9.1 1.I-9.1 1.I 8.
Peterlin, et al. "Optical probing of neuronal circuits with calcium indicators," PNAS, 2000, vol. 97, No. 7: pp. 3619-3624.
Petersen et al. "Spatiotemporal Dynamics of Sensory Responses in Layer 2/3 of Rat Barrel Cortex Measured In Vivo by Voltage-Sensitive Dye Imaging Combined with Whole-Cell Voltage Recordings and Neuron Reconstructions," The Journal of Neuroscience, 2003, vol. 23, No. 3, pp. 1298-1309.
Petrecca, et al. "Localization and Enhanced Current Density of the Kv4.2 Potassium Channel by Interaction with the Actin-Binding Protein Filamin," The Journal of Neuroscience, 2000, vol. 20, No. 23, pp. 8736-8744.
Pettit, et al. "Local Excitatory Circuits in the Intermediate Gray Layer of the Superior Colliculus", J Neurophysiol., 1999, vol. 81, No. 3: pp. 1424-1427.
Potter, "Transfection by Electroporation." Supplement 62, Current Protocols in Molecular Biology, 1996, 9.3.1-9.3.6.
Pouille, et al. "Routing of spike series by dynamic circuits in the hippocampus", Nature, 2004, vol. 429: pp. 717-723.
Qiu et al. "Induction of photosensitivity by heterologous expression of melanopsin", Nature, 2005, vol. 433: pp. 745-749.
Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7, pp. 2534-2546.
Randic, et al. "Long-term Potentiation and Long-term Depression of Primary Afferent Neurotransmission in the Rat Spinal Cord", 1993, Journal of Neuroscience, vol. 13, No. 12, pp. 5228-5241.
Rathnasingham et al., "Characterization of implantable microfabricated fluid delivery devices," IEEE Transactions on Biomedical Engineering, 2004, vol. 51, No. 1: pp. 138-145.
Ritter, et al., "Monitoring Light-induced Structural Changes of Channelrhodopsin-2 by UV-Visible and Fourier Transform Infared Spectroscopy", 2008, The Journal of Biological Chemistry, vol. 283, No. 50, pp. 35033-35041.
Rivera et al., "BDNF-Induced TrkB Activation Down-Regulates the K+-Cl-cotransporter KCC2 and Impairs Neuronal Cl-Extrusion", The Journal of Cell Biology, 2002, vol. 159: pp. 747-752.
Rosenkranz, et al. "The prefrontal cortex regulates lateral amygdala neuronal plasticity and responses to previously conditioned stimuli", J. Neurosci., 2003, vol. 23, No. 35: pp. 11054-11064.
Rousche, et al., "Flexible polyimide-based intracortical electrode arrays with bioactive capability," IEEE Transactions on Biomedical Engineering, 2001, vol. 48, No. 3, pp. 361-371.
Rubinson et at. "A lentivirus-based system to functionally silence genes in primary mammalian cells, stem cells and transgenic mice by RNA interference," Nature Genetics, 2003, vol. 33, p. 401-406.
Rudiger et at. "Specific arginine and threonine residues control anion binding and transport in the light-driven chloride pump halorhodopsin," The EMBO Journal, 1997, vol. 16, No. 13, pp. 3813-3821.
Salzman, et al. "Cortical microstimulation influences perceptual judgements of motion direction", Nature, 1990, vol. 346, pp. 174-177.
Sajdyk, et al., "Excitatory Amino Acid Receptors in the Basolateral Amygdala Regulate Anxiety Responses in the Social Interaction Test", Brain Research, 1997, vol. 764, pp. 262-264.
Sato et al. "Role of Anion-binding Sites in cytoplasmic and extracellular channels of *Natronomonas pharaonis* halorhodopsin," Biochemistry, 2005. vol. 44, pp. 4775-4784.
Sauer "Site-specific recombination: developments and applications," Current Opinion in Biotechnology, 1994, vol. 5, No. 5: pp. 521-527.
Schiff, et al. "Behavioral improvements with thalamic stimulation after severe traumatic brain injury," Nature, 2007, vol. 448, pp. 600-604.
Schlaepfer et al. "Deep Brain stimulation to Reward Circuitry Alleviates Anhedonia in Refractory Major Depresion," Neuropsychopharmacology, 2008, vol. 33, pp. 368-377.
Sclimenti, et al. "Directed evolution of a recombinase for improved genomic integration at a native human sequence," Nucleic Acids Research, 2001, vol. 29, No. 24: pp. 5044-5051.
Shepherd, et al. "Circuit Analysis of Experience-Dependent Plasticity in the Developing Rat Barrel Cortex", Neuron, 2003, vol. 38: pp. 277-289.
Shibasaki et al. "Effects of body temperature on neural activity in the hippocampus: Regulation of resting membrane potentials by transient receptor potential vanilloid 4," The Journal of Neuroscience, 2007, vol. 27, No. 7: pp. 1566-1575.
Silver, et al. "Amino terminus of the yeast *GAL4* gene product is sufficient for nuclear localization" PNAS, 1984, vol. 81, No. 19: pp. 5951-5955.

(56) References Cited

OTHER PUBLICATIONS

Singer et al. "Elevated Intrasynaptic Dopamine Release in Tourette's Syndrome Measured by PET," American Journal of Psychiatry, 2002, vol. 159: pp. 1329-1336.
Slimko et al., "Selective Electrical Silencing of Mammalian Neurons In Vitro by the use of Invertebrate Ligand-Gated Chloride Channels", The Journal of Neuroscience, 2002, vol. 22, No. 17: pp. 7373-7379.
Smith et al. "Diversity in the serine recombinases", Molecular Microbiology, 2002, vol. 44, No. 2: pp. 299-307.
Song et al. "Differential Effect of TEA on Long-Term Synaptic Modification in Hippocampal CA1 and Dentate Gyrus in vitro." Neurobiology of Learning and Memory, 2001, vol. 76, No. 3, pp. 375-387.
Song, "Genes responsible for native depolarization-activated K+ currents in neurons," Neuroscience Research, 2002, vol. 42, pp. 7-14.
Stark, et al. "Catalysis by site-specific recombinases," Trends Genet., 1992, vol. 8, No. 12: pp. 432-439.
Stockklausner et al. "A sequence motif responsible for ER export and surface expression of Kir2.0 inward rectifier K+ channels," FEBS Letters, 2001, vol. 493, pp. 129-133.
Stoll, et al. "Phage TP901-I site-specific integrase functions in human cells," Journal of Bacteriology, 2002, vol. 184, No. 13: pp. 3657-3663.
Swanson, "Lights, Opsins, Action! Optogenetics Brings Complex Neuronal Circuits into Sharper Focus", 2009, The Dana Foundation, [URL:http://www.dana.org/news/features/detail.aspx?id=24236], PDF File, pp. 1-3.
Swiss-Prot_Q2QCJ4, Opsin 1, Oct. 31, 2006, URL: http://www.ncbi.nlm.nig.gov/protein/Q2QCJ4.
Takahashi, et al."Diversion of the Sign of Phototaxis in a *Chlamydomonas reinhardtii* Mutant Incorporated with Retinal and Its Analogs," FFEBS Letters, 1992, vol. 314, No. 3, pp. 275-279.
Tatarkiewicz, et al. "Reversal of Hyperglycemia in Mice After Subcutaneous Transplantation of Macroencapsulated Islets", Transplantation, 1999, vol. 67, No. 5: pp. 665-671.
Tottene et al., "Familial Hemiplegic Migraine Mutations Increase $Ca^{2+}$ Influx Through Single Human $Ca_v2.1$ Current Density in Neurons", PNAS USA, 2002, vol. 99, No. 20: pp. 13284-13289.
Tsau et al. "Distributed Aspects of the Response to Siphon Touch in *Aplysia*: Spread of Stimulus Information and Cross-Correlation Analysis," The Journal of Neuroscience, 1994, vol. 14, No. 7, pp. 4167-4184.
[No Authors Listed] "Two bright new faces in gene therapy," Nature Biotechnology, 1996, vol. 14: p. 556.
Tye et. al., "Amygdala circuitry mediating reversible and bidirectional control of anxiety", Nature, 2011, vol. 471(7338): pp. 358-362.
Tye et. al., Supplementary Materials: "An optically-resolved microcircuit for bidirectional anxiety control", Nature, 2011, vol. 471(7338): pp. 358-362.
Tye, et al. "Optogenetic investigation of neural circuits underlying brain disease in animal models," Nature Reviews Neuroscience (Mar. 2012), 13(4):251-266.
"SubName: Full=Channelrhodopsin-1", retrieved from EBI accession No. UNIPROT: B4Y103. Database accession No. B4Y103. Sep. 23, 2008.
Ulmanen, et al. "Transcription and translation of foreign genes in *Bacillus subtilis* by the aid of a secretion vector," Journal of Bacteriology, 1985, vol. 162 No. 1: pp. 176-182.
Van Der Linden, "Functional brain imaging and pharmacotherapy in social phobia: single photon emission computed tomography before and after Treatment with the selective serotonin reuptake inhibitor citalopram," Prog Neuro-psychopharmacol Biot Psychiatry, 2000, vol. 24, No. 3: pp. 419-438.
Vanin, et al. "Development of high-titer retroviral producer cell lines by using Cre-mediated recombination," Journal of Virology, 1997, vol. 71, No. 10: pp. 7820-7826.
Vetter, et al. "Development of a Microscale Implantable Neural Interface (MINI) Probe System," Proceedings of the 2005 IEEE, Engineering in Medicine and Biology 27th Annual Conference, Shanghai, China, Sep. 1-4, 2005.

Wagner, "Noninvasive Human Brain Stimulation", Annual Rev. Biomed. Eng. 2007. 9:I9.I-19.39.
Ward, et al. "Construction and characterisation of a series of multicopy promoter-probe plasmid vectors for *Streptomyces* using the aminoglycoside phosphotransferase gene from Tn5 as indicator", 1986, Mol. Gen. Genet., vol. 203: pp. 468-478.
Watson, et al. "Targeted transduction patterns in the mouse brain by lentivirus vectors pseudotyped with VSV, Ebola, Mokola, LCMV, or MuLV envelope proteins," Molecular Therapy, 2002, vol. 5, No. 5, pp. 528-537.
Wang et al. "Direct-current Nanogenerator Driven by Ultrasonic Waves," Science, 2007, vol. 316, pp. 102-105.
Wang et. al., "High-speed mapping of synaptic connectivity using photostimulation in Channelrhodopsin-2 transgenic mice", PNAS, 2007, vol. 104, No. 19, pp. 8143-8148.
Weick et al. "Interactions with PDZ Proteins Are Required for L-Type Calcium Channels to Activate cAMP Response Element-Binding Protein-Dependent Gene Expression," The Journal of Neuroscience, 2003, vol. 23, No. 8, pp. 3446-3456.
Wells et al. "Application of Infrared light for in vivo neural stimulation," Journal of Biomedical Optics, 2005, vol. 10(6), pp. 064003-1-064003-12.
Witten et. al., Supporting Online Material for: "Cholinergic Interneurons Control Local Circuit Activity and Cocaine Conditioning", Science, 2010, vol. 330: 17 pages.
Witten et. al., "Cholinergic Interneurons Control Local Circuit Activity and Cocaine Conditioning", Science, 2010, vol. 330, No. 6011: pp. 1677-1681.
Yamazoe, et al. "Efficient generation of dopaminergic neurons from mouse embryonic stem cells enclosed in hollow fibers", Biomaterials, 2006, vol. 27, pp. 4871-4880.
Yan et al., "Cloning and Characterization of a Human β, β-Carotene-15, 15'-Dioxygenase that is Highly Expressed in the Retinal Pigment Epithelium", Genomics, 2001, vol. 72: pp. 193-202.
Yizhar et. al., "Neocortical excitation/inhibition balance in information processing and social dysfunction", Nature, 2011, vol. 477, pp. 171-178; and Supplemental Materials; 41 pages.
Yoon, et al., "A micromachined silicon depth probe for multichannel neural recording," IEEE Transactions Biomedical Engineering, 2000, vol. 47, No. 8, pp. 1082-1087.
Yoshimura, et al. "Excitatory cortical neurons form fine-scale functional networks", Nature, 2005, vol. 433: pp. 868-873.
Zacharias et al. "Recent advances in technology for measuring and manipulating cell signals," Current Opinion in Neurobiology, 2000, vol. 10: pp. 416-421.
Zemelman, et al. "Selective Photostimulation of Genetically ChARGed Neurons", Neuron, 2002, vol. 33: pp. 15-22.
Zemelman, et al. "Photochemical gating of heterologous ion channels: Remote control over genetically designated populations of neurons", PNAS, 2003, vol. 100, No. 3: pp. 1352-1357.
Zhang, et al. "Channelrhodopsin-2 and optical control of excitable cells," Nature Methods, 2006, vol. 3, No. 10, pp. 785-792.
Zhang, et al. "Red-Shifted Optogenetic Excitation: a Tool for Fast Neural Control Derived from *Volvox carteri*", Nature Neurosciences, 2008, vol. 11, No. 6, pp. 631-633.
Zhang "Multimodal fast optical interrogation of neural circuitry," Nature, 2007, vol. 446, pp. 633-641.
Zrenner, E., "Will Retinal Implants Restore Vision?" Science, 2002, vol. 295, No. 5557, pp. 1022-1025.
Zufferey, et al. "Self-Inactivating Lentivirus Vector for Safe and Efficient in Vivo Gene Delivery", Journal of Virology, 1998, vol. 72, No. 12, pp. 9873-9880.
U.S. Appl. No. 13/555,981, filed Jul. 23, 2012, Deisseroth, et al.
U.S. Appl. No. 13/622,809, filed Sep. 9, 2012, Deisseroth, et al.
U.S. Appl. No. 13/623,612, filed Sep. 20, 2012, Deisseroth, et al.
U.S. Appl. No. 13/718,243, filed Dec. 18, 2012, Deisseroth, et al.
U.S. Appl. No. 13/763,119, filed Feb. 8, 2013, Deisseroth, et al.
U.S. Appl. No. 13/763,132, filed Feb. 8, 2012, Deisseroth, et al.
U.S. Appl. No. 13/772,732, filed Feb. 21, 2013, Deisseroth, et al.
U.S. Appl. No. 13/847,653, filed Mar. 20, 2013, Deisseroth, et al.
U.S. Appl. No. 13/847,785, filed Mar. 20, 2013, Deisseroth, et al.
U.S. Appl. No. 13/849,913, filed Mar. 25, 2013, Deisseroth, et al.
U.S. Appl. No. 13/850,426, filed Mar. 26, 2013, Deisseroth, et al.

(56) References Cited

OTHER PUBLICATIONS

U.S. Appl. No. 13/850,428, filed Mar. 26, 2013, Deisseroth, et al.
U.S. Appl. No. 13/850,436, filed Mar. 26, 2013, Deisseroth, et al.
U.S. Appl. No. 13/850,709, filed Mar. 26, 2013, Deisseroth, et al.
U.S. Appl. No. 13/854,750, filed Apr. 1, 2013, Deisseroth, et al.
U.S. Appl. No. 13/854,754, filed Apr. 1, 2013, Deisseroth, et al.
U.S. Appl. No. 13/875,966, filed May 2, 2013, Deisseroth, et al.
U.S. Appl. No. 13/882,566, filed Nov. 4, 2013, Deisseroth, et al.
U.S. Appl. No. 13/882,666, filed Nov. 4, 2013, Deisseroth, et al.
U.S. Appl. No. 13/882,670, filed Nov. 4, 2013, Deisseroth, et al.
U.S. Appl. No. 13/882,703, filed Nov. 4, 2013, Deisseroth, et al.
U.S. Appl. No. 13/882,705, filed Nov. 4, 2013, Deisseroth, et al.
U.S. Appl. No. 13/882,719, filed Nov. 4, 2013, Deisseroth, et al.
Tam, B. et al., "Identification of an Outer Segment Targeting Signal in the COOH Terminus of Rhodopsin Using Transgenic Xenopus laevis", The Journal of Cell Biology, 2000, vol. 151, No. 7, pp. 1369-1380.
Lanyi et al. "The primary structure of a Halorhodopsin from *Natronobacterium Pharaonis*" Journal of Biological Chemistry 1990, vol. 265, No. 3, p. 1253-1260.
Hofherr et al. "Selective Golgi export of Kir2.1 controls the stoichiometry of functional Kir2.x channel heteromers"Journal of Cell Science, 2005, vol. 118, p. 1935-1943.
Loetterle, et al., "Cerebellar Stimulation: Pacing the Brain", American Journal of Nursing, 1975, vol. 75, No. 6, pp. 958-960.
Adamantidis, et al., "Optogenetic Interrogation of Dopaminergic Modulation of the Multiple Phases of Reward-Seeking Behavior", J. Neurosci, 2011, vol. 31, No. 30, pp. 10829-10835.
Han, et al., "Multiple-Color Optical Activation, Silencing, and Desynchronization of Neural Activity with Single-Spike Temporal Resolution", PLoS One, 2007, vol. 2, No. 3, pp. 1-12.
Kinoshita, et al., "Optogenetically Induced Supression of Neural Activity in the Macaque Motor Cortex", Poster Sessions Somatomotor System, Others,2010, pp. 141-154.
Rein, et al., "The Optogenetic (r)evolution", Mol. Genet. Genomics, 2012, vol. 287, No. 2, pp. 95-109.
Remy, et al., "Depression in Parkinson's Disease: Loss of Dopamine and Noradrenaline Innervation in the Limbic System", Brain, 2005, vol. 128 (Pt 6), pp. 1314-1322.
Tsai, et al., "Phasic Firing in Dopaminergic Neurons in Sufficient for Behavioral Conditioning", Science, 2009, vol. 324, pp. 1080-1084.
Zhao, et al., "Improved Expression of Halorhodopsin for Light-Induced Silencing of Neuronal Activity", Brain Cell Biology, 2008, vol. 36 (1-4), pp. 141-154.
Balint, et al., "The Nitrate Transporting Photochemical Reaction Cycle of the Pharaonis Halorhodopsin", Biophysical Journal, 2004, vol. 86, pp. 1655-1663.
Gradinaru, et al., Molecular and Cellular Approaches for Diversifying and Extending Optogenetics, Cell, 2010, vol. 141, No. 1, pp. 154-165.
RecName: Full=Halorhodopsin; Short=HR; Alt Name: Full=NpHR; XP002704922, retrieved from EBI accession No. UNIPROT: P15647. Database accession No. P15647. Apr. 1, 1990.
"N. pharaonis halorhodopsin (hop) gene, complete cds.", XP002704883, retrieved from EBI accession No. EMBL: J05199. Database accession No. J05199. Nov. 22, 1990.
"Subname: Fluu= Bacteriorhodopsin"; XP002704863, retrieved from EBI accession No. UNIPROT: B0R5N9. Database accession No. B0R5N9. Apr. 8, 2008.
Zhang, et al., "The Microbial Opsin Family of Optogenetic Tools", Cell, 2011, vol. 147, No. 7, pp. 1146-1457.
Wang, et al., "Molecular Determinants Differentiating Photocurrent Properties of Two Channelrhodopsins from Chlamydomonas", 2009, The Journal of Biological Chemistry, vol. 284, No. 9, pp. 5685-5696.
Delaney et al., "Evidence for a long-lived 13-cis-containing intermediate in the photocycle of the leu 93 → ala bacteriorhodopsin mutant", J. Physical Chemistry B, 1997, vol. 101, No. 29, pp. 5619-5621.
Fenno et al., "The development and application of optogenetics", Annual Review of Neuroscience, 2011, vol. 34, No. 1, pp. 389-412.

Gunaydin et al., "Ultrafast optogenetic control", Nature Neuroscience, 2010, vol. 13, No. 3, pp. 387-392.
Hira et al., "Transcranial optogenetic stimulation for functional mapping of the motor cortex", J Neurosci Methods, 2009, vol. 179, pp. 258-263.
Lalumiere, R., "A new technique for controlling the brain: optogenetics and its potential For use in research and the clinic", Brain Stimulation, 2011, vol. 4, pp. 1-6.
Lin, "A user's guide to channelrhodopsin variants: features, limitations and future developments", Exp Physiol, 2010, vol. 96, No. 1, pp. 19-25.
Mancuso et al., "Optogenetic probing of functional brain circuitry", Experimental Physiology, 2010, vol. 96.1, pp. 26-33.
Peralvarez-Marin et al., "Inter-helical hydrogen bonds are essential elements for intra-protein signal transduction: The role of Asp115 in bacteriorhodopsin transport function", J. Mol. Biol., 2007, vol. 368, pp. 666-676.
Pinkham et al., "Neural bases for impaired social cognition in schizophrenia and autism spectrum disorders", Schizophrenia Research, 2008, vol. 99, pp. 164-175.
Sohal et al., "Parvalbumin neurons and gamma rhythms enhance cortical circuit performance", Nature, 2009, vol. 459, No. 7247, pp. 698-702.
Yizhar et al., "Optogenetics in neural systems", Neuron Primer, 2011, vol. 71, No. 1, pp. 9-34.
Li et al., "Surface Expression of Kv1 Channels is Governed by a C-Terminal Motif", J. Bioi. Chem. (2000), 275(16):11597-11602.
Lonnerberg et al. "Regulatory Region in Choline Acetyltransferase Gene Directs Developmental and Tissue-Specific Expression in Transgenic mice", Proc. Natl. Acad. Sci. USA (1995), 92(9):4046-4050.
Varo et al.,"Light-Driven Chloride Ion Transport by Halorhodopsin from Natronobacterium pharaonis. 2. Chloride Release and Uptake, Protein Conformation Change, and Thermodynamics", Biochemistry (1995), 34(44):14500-14507.
Deisseroth, et al., "Controlling the Brain with Light", Scientific American, 2010, vol. 303, pp. 48-55.
Douglass, et al., "Escape Behavior Elicited by Single, Channelrhodopsin-2-evoked Spikes in Zebrafish Somatosensory Neurons", Curr Biol., 2008, vol. 18, No. 15, pp. 1133-1137.
Sineshchekov, et al., "Two Rhodopsins Mediate Phototaxis to Low and High Intensity Light in Chlamydomas Reinhardtil", PNAS, 2002, vol. 99, No. 13, pp. 8689-8694.
Tønnese, et al., "Optogenetic Control of Epileptiform Activity", PNAS, 2009, vol. 106, No. 29, pp. 12162-12167.
Gradinaru et al., "Targeting and readout strategies for fast optical neural control in vitro and in vivo", J Neuroscience, 2007, 27(52):14231-14238.
Fiala et al., "Optogenetic approaches in neuroscience", Current Biology, Oct. 2010, 20(20):R897-R903.
Gradinaru et al., "Optical deconstruction of parkinsonian neural circuitry", Science, Apr. 2009, 324(5925):354-359.
Liu et al., "Optogenetics 3.0", Cell, Apr. 2010, 141(1):22-24.
Malin et al., "Involvement of the rostral anterior cingulate cortex in consolidation of inhibitory avoidance memory: Interaction with the basolateral amygdala", Neurobiol Learning Mem, 2007, 87(2):295-302.
Mayford et al., "Control of memory formation through regulated expression of CAMKII Transgene", Science, Dec. 1996, 274:1678-1683.
Schroll et al., "Light-induced activation of distinct modulatory neurons triggers appetitive or aversive learning in drosophila larvae", Current Biology, Sep. 2006, 16(17):1741-1747.
Babin et al., "Zebrafish Models of Human Motor Neuron Diseases: Advantages and Limitations", Progress in Neurobiology (2014), 118:36-58.
Santana et al., "Can Zebrafish Be Used as Animal Model to Study Alzheimer's Disease?" Am. J. Neurodegener. Dis. (2012), 1(1):32-48.
Sheikh et al., "Neurodegenerative Diseases: Multifactorial Conformational Diseases and Their Therapeutic Interventions", Journal of Neurodegenerative Diseases (2013), Article ID 563481:1-8.

(56) References Cited

OTHER PUBLICATIONS

Suzuki et al., "Stable Transgene Expression from HSV Amplicon Vectors in the Brain: Potential Involvement of Immunoregulatory Signals", Molecular Therapy (2008), 16(10):1727-1736.
Thomas et al., "Progress and Problems with the Use of Viral Vectors for Gene", Nat. Rev. Genet. (2003), 4(5):346-358.
Shibasaki et al., "Effects of body temperature on neural activity in the hippocampus: Regulation of resting membrane potentials by transient receptor potential vanilloid 4," The Journal of Neuroscience, 2007, 27(7):1566-1575.
Takahashi, et al., "Induction of Pluripotent Stem Cells from Mouse Embryonic and Adult Fibroblast Cultures by Defined Factors", 2006, Cell, vol. 126, pp. 663-676.
Davis; "The many faces of epidermal growth factor repeats," The New Biologist; vol. 2, No. 5, pp. 410-419 (1990).
De Palma, et al.; "In Vivo Targeting of Tumor Endothelial Cells by Systemic Delivery of Lentiviral Vectors"; Human Gene Therapy; vol. 14, pp. 1193-1206 (Aug. 10, 2003).
Ebi accession No. UNIPROT: A7U0Y6; "SubName: Full=Bacteriorhodopsin"; (Aug. 10, 2010).
Ihara, et al.; "Evolution of the Archaeal Rhodopsins: Evolution Rate Changes by Gene Duplication and Functional Differentiation"; J. Mol. Biol.; vol. 285, pp. 163-174 (1999).
Kaiser; "Clinical research. Death prompts a review of gene therapy vector"; Science; 317(5838):580 (Aug. 3, 2007).
Kay; "State-of-the-art gene-based therapies: the road ahead"; Nature Reviews Genetics; vol. 12, pp. 316-328 (May 2011).
Singer; "Light Switch for Bladder Control"; Technology Review; pp. 1-2 (Sep. 14, 2009).
Skolnick, et al.; "From genes to protein structure and function: novel applications of computational approaches in the genomic era"; Trends Biotechnol; vol. 18, No. 1, pp. 34-39 (Jan. 2000).
Soofiyani, et al.; "Gene Therapy, Early Promises, Subsequent Problems, and Recent Breakthroughs"; Advanced Pharmaceutical Bulletin; vol. 3, No. 2, pp. 249-255 (2013).
Brewin; "The Nature and Significance of Memory Disturbance in Posttraumatic Stress Disorder"; Ann. Rev. Clin. Psychol.; vol. 7, pp. 203-227 (2011).
Raper, et al.; "Fatal systemic inflammatory response syndrome in a ornithine transcarbamylase deficient patient following adenoviral gene transfer." Mol. Genet. Metab.; vol. 80, No. 1-2, pp. 148-158 (Sep.-Oct. 2003).
Samuelson; "Post-traumatic stress disorder and declarative memory functioning: a review"; Dialogues in Clinical Neuroscience; vol. 13, No. 3, pp. 346-351 (2011).
Berndt et al., "Structure-Guided Transformation of Channelrhodopsin into a Light-Activated Chloride Channel", Science (Apr. 2014), 344(6182):420-424.
Chow et al., "Optogenetics and Translational Medicine", Science Translational Medicine (Mar. 2013), 5(177):177ps5.
Eijkelkamp, et al. "Neurological perspectives on voltage-gated sodium channels", Brain (Sep. 2012), 135(Pt 9):2585-2612.
Garrido et al., "A targeting motif involved in sodium channel clustering at the axonal initial segment", Science (Jun. 2003), 300(5628):2091-4.
Han; et al., "Two-color, bi-directional optical voltage control of genetically-targeted neurons", CoSyne (2007), Abstract Presentation, Poster III-67, p. 269, Presented Feb. 24, 2007.
Hustler; et al., "Acetylcholinesterase staining in human auditory and language cortices: regional variation of structural features", Cereb Cortex (Mar.-Apr. 1996), 6(2):260-70.
Iyer et al.,"Virally mediated optogenetic excitation and inhibition of pain in freely moving nontransgenic mice", Nat. Biotechnol., (Mar. 2014), 32(3):274-8
Ji et al., "Light-evoked Somatosensory Perception of Transgenic Rats that Express Channelrhodopsin-2 in Dorsal Root Ganglion Cells", PLoS One (2012), 7(3):e32699.
Jennings et al., "Distinct extended amygdala circuits for divergent motivational states," Nature (Apr. 2013), 496 (7444):224-8.
Kim et al., "PDZ domain proteins of synapses", Nature Reviews Neuroscience, (Oct. 2004), 5(10):771-81.
Kim et al., "Diverging neural pathways assemble a behavioural state from separable features in anxiety" Nature (Apr. 2013), 496(7444):219-23.
Kokel et al., "Photochemical activation of TRPA1 channels in neurons and animals", Nat Chem Biol (Apr. 2013), 9 (4):257-63.
Lammel et al., "Input-specific control of reward and aversion in the ventral tegmental area", Nature (Nov. 2012), 491 (7423): 212-7.
Liske et al., "Optical inhibition of motor nerve and muscle activity in vivo", Muscle Nerve (Jun. 2013), 47(6):916-21.
Llewellyn et al., "Orderly recruitment of motor units under optical control in vivo", Nature Medicine, (Oct. 2010), 16 (10):1161-5.
Mattis et al., "Principles for applying optogenetic tools derived from direct comparative analysis of microbial opsins", Nat Methods (Dec. 2011), 9(2):159-72.
Mourot et al., "Rapid Optical Control of Nociception with an Ion Channel Photoswitch", Nat Methods (Feb. 2012), 9 (4):396-402.
Nieh et al., "Optogenetic dissection of neural circuits underlying emotional valence and motivated behaviors", Brain Research, (May 2012), 1511:73-92.
Slamovits et al., "A bacterial proteorhodopsin proton pump in marie eukaryotes", Nature Communications (Feb. 2011), 2:183.
Towne et al., "Efficient transduction of non-human primate motor neurons after intramuscular delivery of recombinant AAV serotype 6", Gene Ther. (Jan. 2010), 17(1):141-6.
Towne et al., "Optogenetic control of targeted peripheral axons in freely moving animals", PLoS One (Aug. 2013), 8 (8):e72691.
Towne et al., "Recombinant adeno-associated virus serotype 6 (rAAV2/6)-mediated gene transfer to nociceptive neurons through different routes of delivery", Mol Pain (Sep. 2009), 5:52.
Wang et al., "Mrgprd-Expressing Polymodal Nociceptive Neurons Innervate Most Known Classes of Substantia Gelatinosa Neurons", J Neurosci (Oct. 2009), 29(42):13202-13209.
Williams et al., "From optogenetic technologies to neuromodulation therapies", Sci Transl Med. (Mar. 2013), 5 (177):177ps6.
Ageta-Ishihara et al., "Chronic overload of SEPT4, a parkin substrate that aggregates in Parkinson's disease, cause behavioral alterations but not neurodegeneration in mice", Molecular Brain, 2013, vol. 6, 14 pages.
Axoclamp-28 Microelectrode claim theory and operation. Accessed from https://physics.ucsd.edu/neurophysics/Manuals/Axon%020Instruments/Axoclamp-2B_Manual.pdf on Dec. 12, 2014.
Cowan et al., "Targeting gene expression to endothelium in transgenic animals: a comparison of the human ICAM-2, PECAM-1, and endoglin promoters", Xenotransplantation, 2003, vol. 10, pp. 223-231.
Definition of Psychosis (2015).
Ebert et al., "A Moloney MLV-rat somatotropin fusion gene produces biologically active somatotropin in a transgenic pig", Mol. Endocrinology, 1988, vol. 2, pp. 277-283.
Hammer et al., "Spontaneous inflammatory disease in transgenic rats expressing HLA-B27 and Human $B_2m$: an animal model of HLA-B27-associated human disorders", Cell, 1990, vol. 63, pp. 1099-1112.
Karra, et al. "Transfection Techniques for Neuronal Cells", The Journal of Neuroscience, 2010, vol. 30, No. 18, pp. 6171-6177.
Kelder et al., "Glycoconjugates in human and transgenic animal milk", Advances in Exp. Med. and Biol., 2001, vol. 501, pp. 269-278.
Mullins et al., "Fulminant hypertension in transgenic rats harbouring the mouse *Ren-2* gene", Nature, 1990, vol. 344, pp. 541-544.
Mullins et al., "Expression of the DBA/2J *Ren-2* gene in the adrenal gland of transgenic mice", EMBO, 1989, vol. 8, pp. 4065-4072.
Taurog et al., "HLA-B27 in inbred and non-inbred transgenic mice", J. Immunol., 1988, vol. 141, pp. 4020-4023.
Wall, "Transgenic livestock: Progress and prospects for the future", Theriogenology, 1996, vol. 45, pp. 57-68.
Wang, et al., "High-speed mapping of synaptic connectivity using photostimulation in Channelrhodopsin-2 transgenic mice", Proceedings of the National Academy of Sciences, 2007, vol. 104, No. 19, pp. 8143-8148.

(56) References Cited

OTHER PUBLICATIONS

Written opinion of PCT Application No. PCT/US2011/059383 (May 9, 2012).

Han, et a.; "Virogenetic and optogenetic mechanisms to define potential therapeutic targets in psychiatric disorders"; Neuropharmacology; vol. 62, pp. 89-100 (2012).

Zhang, et al.; "Optogenetic interrogation of neural circuits: Technology for probing mammalian brain structures"; Nature Protocols; vol. 5, No. 3, pp. 439-456 (Mar. 1, 2010).

Ali; "Gene and stem cell therapy for retinal disorders"; vision-research.en—The Gateway to European Vision Research; accessed from http://www.vision-research.eu/index.php?id=696, 10 pages (accessed Jul. 24, 2015).

Mueller, et al.; "Clinical Gene Therapy Using Recombinant Adeno-Associated Virus Vectors"; Gene Therapy; vol. 15, pp. 858-863 (2008).

Asano, et al.; "Optically Controlled Contraction of Photosensitive Skeletal Muscle Cells"; Biotechnology & Bioengineering; vol. 109, No. 1, pp. 199-204 (Jan. 2012).

Bruegmann, et al.; "Optogenetic control of heart muscle in vitro and in vivo"; Nature Methods; vol. 7, No. 11, pp. 897-900(Nov. 2010).

Bruegmann, et al.; "Optogenetics in cardiovascular research: a new tool for light-induced depolarization of cardiomyocytes and vascular smooth muscle cells in vitro and in vivo"; European Heart Journal; vol. 32, No. Suppl . 1, p. 997 (Aug. 2011).

Genbank Accession No. AAG01180.1; Idnurm, et al.; pp. 1 (Mar. 21, 2001).

Genbank Accession No. ABT17417.1; Sharma, et al.; pp. 1 (Aug. 15, 2007).

Genbank Accession No. BAA09452.1; Mukohata et al.; pp. 1 (Feb. 10, 1999).

Kessler, et al.; "Gene delivery to skeletal muscle results in sustained expression and systemic delivery of a therapeutic protein"; Proc. Natl. Acad. Sci. USA; vol. 93, pp. 14082-14087 (Nov. 1996).

Wang, et al.; "Laser-evoked synaptic transmission in cultured hippocampal neurons expressing channelrhodopsin-2 delivered by adeno-associated virus"; Journal of Neuroscience Methods; vol. 183, pp. 165-175 (2009).

Han, et al., "Millisecond-Timescale Optical Control of Neural Dynamics in the Nonhuman Primate Brain"; Neuron; vol. 62, pp. 191-198 (Apr. 30, 2009).

Ibbin I, et al.; "A Field Conjugation Method for Direct Synthesis of Hyperthermia Phased-Array Heating Patterns"; IEEE Transactions on Ultrasonics, Ferroelectrics, and Frequency Control; vol. 36, No. 1, pp. 3-9 (Jan. 1989).

Berlanga, et a.; "Cholinergic Interneurons of the Nucleus Accumbens and Dorsal Striatum are Activated by the Self-Administration of Cocaine"; Neuroscience; vol. 120, pp. 1149-1156 (2003).

Day, et al.; "The Nucleus Accumbens and Pavlovian Reward Learning"; Neuroscientist; vol. 13, No. 2, pp. 148-159 (Apr. 2007).

Knopfel, et al.; "A comprehensive concept of optogenetics"; Progress in Brain Research; vol. 196, pp. 1-28 (2012).

Packer, et al.; "Targeting Neurons and Photons for Optogenetics"; Nature Neuroscience; vol. 16, No. 7, pp. 805-815 (Jul. 2013).

\* cited by examiner

MAMMALIAN CODON OPTIMIZED NUCLEOTIDE SEQUENCE THAT ENCODES A VARIANT OPSIN POLYPEPTIDE DERIVED FROM NATROMONAS PHARAONIS (NPHR)

RELATED PATENT DOCUMENTS

This application is a continuation of U.S. patent application Ser. No. 13/208,419, filed Aug. 12, 2011, which is a continuation of U.S. patent application Ser. No. 12/041,628, filed Mar. 3, 2008, and claims benefit under 35 U.S. §119(e) of U.S. Provisional Application Ser. No. 60/904,303 filed on Mar. 1, 2007, which applications are incorporated by reference herein in their entirety.

FEDERALLY-SPONSORED RESEARCH OR DEVELOPMENT

This invention was made with Government support under contract OD000616 awarded by the National Institutes of Health. The Government has certain rights in this invention.

INCORPORATION-BY-REFERENCE OF MATERIAL SUBMITTED ELECTRONICALLY

Incorporated by reference in its entirety is a computer-readable nucleotide/amino acid sequence listing and identified as follows: One 27,705 Byte ASCII (Text) file named "stfd-165PA_ST25" created on Nov. 19, 2010.

FIELD OF THE INVENTION

The present invention relates generally to systems and approaches for stimulating target cells, and more particularly to using optics to stimulate the target cells.

BACKGROUND

The stimulation of various cells of the body has been used to produce a number of beneficial effects. One method of stimulation involves the use of electrodes to introduce an externally generated signal into cells. One problem faced by electrode-based brain stimulation techniques is the distributed nature of neurons responsible for a given mental process. Conversely, different types of neurons reside close to one another such that only certain cells in a given region of the brain are activated while performing a specific task. Alternatively stated, not only do heterogeneous nerve tracts move in parallel through tight spatial confines, but the cell bodies themselves may exist in mixed, sparsely embedded configurations. This distributed manner of processing seems to defy the best attempts to understand canonical order within the central nervous system (CNS), and makes neuromodulation a difficult therapeutic endeavor. This architecture of the brain poses a problem for electrode-based stimulation because electrodes are relatively indiscriminate with regards to the underlying physiology of the neurons that they stimulate. Instead, physical proximity of the electrode poles to the neuron is often the single largest determining factor as to which neurons will be stimulated. Accordingly, it is generally not feasible to absolutely restrict stimulation to a single class of neuron lasing electrodes.

Another issue with the use of electrodes for stimulation is that because electrode placement dictates which neurons will be stimulated, mechanical stability is frequently inadequate, and results in lead migration of the electrodes from the targeted area. Moreover, after a period of time within the body, electrode leads frequently become encapsulated with glial cells, raising the effective electrical resistance of the electrodes, and hence the electrical power delivery required to reach targeted cells. Compensatory increases in voltage, frequency or pulse width, however, may spread the electrical current and increase the unintended stimulation of additional cells.

Another method of stimulus uses photosensitive bio-molecular structures to stimulate target cells in response to light. For instance, light activated proteins can be used to control the flow of ions through cell membranes. By facilitating or inhibiting the flow of positive or negative ions through cell membranes, the cell can be briefly depolarized, depolarized and maintained in that state, or hyperpolarized. Neurons are an example of a type of cell that uses the electrical currents created by depolarization to generate communication signals (i.e., nerve impulses). Other electrically excitable cells include skeletal muscle, cardiac muscle, and endocrine cells. Neurons use rapid depolarization to transmit signals throughout the body and for various purposes, such as motor control (e.g., muscle contractions), sensory responses (e.g., touch, hearing, and other senses) and computational functions (e.g., brain functions). Thus, the control of the depolarization of cells can be beneficial for a number of different purposes, including (but not limited to) psychological therapy, muscle control and sensory functions.

SUMMARY

The claimed invention is directed to photosensitive bio-molecular structures and related methods. The present invention is exemplified in a number of implementations and applications, some of which are summarized below.

According to one example embodiment of the present invention, an implantable arrangement is implemented having a light-generation device for generating light. The arrangement also has a biological portion that modifies target cells for stimulation in response to light generated by the light-generation means in vivo.

According to another example embodiment of the present invention, target cells are stimulated using an implantable arrangement. The arrangement includes an electrical light-generation means for generating light and a biological portion. The biological portion has a photosensitive bio-molecular arrangement that responds to the generated light by stimulating target cells in vivo. Stimulation may be manifest as either upregulation, or down-regulation of activity at the target.

According to another example embodiment of the present invention, an implantable device delivers gene transfer vector, such as a virus, which induces expression of photosensitive bio-molecular membrane proteins. The device has a light generator, responsive to (for example, charged by or triggered by) an external signal, to generate light and a biological arrangement that includes the photosensitive bio-molecular protein that responds to the generated light by interacting with target cells in vivo. In this manner, the electronic portions of the device may be used to optically stimulate target cells. Stimulation may be manifested as either upregulation (e.g., increased neuronal firing activity), or downregulation (e.g., neuronal hyperpolarization, or alternatively, chronic depolarization) of activity at the target.

According to another example embodiment of the present invention, a method is implemented for stimulating target cells using photosensitive proteins that bind with the target cells. The method includes a step of implanting the photosensitive proteins and a light generating device near the target cells. The light generating device is activated and the photosensitive protein stimulates the target cells in response to the generated light.

Applications include those associated with any population of electrically-excitable cells, including neurons, skeletal, cardiac, and smooth muscle cells, and insulin-secreting pancreatic beta cells. Major diseases with altered excitation-effector coupling include heart failure, muscular dystrophies, diabetes, pain, cerebral palsy, paralysis, depression, and schizophrenia. Accordingly, the present invention has utility in the treatment of a wide spectrum of medical conditions, from Parkinson's disease and brain injuries to cardiac dysrhythmias, to diabetes, and muscle spasm.

According to other example embodiments of the present invention, methods for generating an inhibitory neuron-current flow involve, in a neuron, engineering a protein that responds to light by producing an inhibitory current to dissuade depolarization of the neuron. In one such method, the protein is halorhodopsin-based and in another method the protein is an inhibitory protein that uses an endogenous cofactor.

According to another example embodiment of the present invention, a method for controlling action potential of a neuron involves the following steps: engineering a first light responsive protein in the neuron; producing, in response to light, an inhibitory current in the neuron that is generated from the first light responsive protein; engineering a second light responsive protein in the neuron; and producing, in response to light, an excitation current in the neuron from the second light responsive protein.

In another method for controlling a voltage level across a cell membrane of a cell, the method comprises: engineering a first light responsive protein in the cell; measuring the voltage level across the cell membrane; and producing, in response to light of a first wavelength and using the first light responsive protein, a current across the cell membrane that is responsive to the measured voltage level.

According to another example embodiment of the present invention, a method for generating an inhibitory-current flow in neurons is implemented. The method includes in a neuron, engineering an inhibitory protein that responds to light by producing an inhibitory current to dissuade depolarization of the neuron, wherein the inhibitory protein does not have the sequence as set forth in GenBank accession number EF474018 and uses an endogenous cofactor to produce the inhibitory current.

According to another example embodiment of the present invention, a method for generating an inhibitory-current flow in neurons is implemented. The method includes in a neuron, engineering a protein that responds to light by producing an inhibitory current to dissuade depolarization of the neuron, wherein the protein uses an endogenous cofactor and results in a toxicity of the engineered neuron that is less than about 75%.

According to another example embodiment of the present invention, a method for controlling action potential of a neuron is implemented. A first light responsive protein is engineered in the neuron. The first light responsive protein does not have the sequence as set forth in GenBank accession number EF474018 and uses an endogenous cofactor to produce the inhibitory current. In response to light, an inhibitory current is produced in the neuron, the current generated from the first light responsive protein. A second light responsive protein is engineered in the neuron. In response to light, an excitation current is produced in the neuron from the second light responsive protein.

According to another example embodiment of the present invention, a method for controlling a voltage level across a cell membrane of a cell is implemented. A first light responsive protein is engineered in the cell. The voltage level across the cell membrane is measured. Light of a first wavelength is generated in response to the measured voltage level. In response to light of a first wavelength and using the first light responsive protein, a first current is produced across the cell membrane that.

According to another example embodiment of the present invention, system controls an action potential of a neuron in vivo. A delivery device introduces a light responsive protein to the neuron, wherein the light responsive protein produces an inhibitory current and is not the sequence as set forth in GenBank accession number EF474018. A light source generates light for stimulating the light responsive protein. A control device controls the generation of light by the light source.

According to another example embodiment of the present invention, a method for treatment of a disorder is implemented. In a group of neurons associated with the disorder, inhibitory proteins are engineered that use an endogenous cofactor to respond to light by producing an inhibitory current to dissuade depolarization of the neurons, wherein the engineered group of neurons has toxicity of less than about 75%. The neurons are exposed to light, thereby dissuading depolarization of the neurons.

According to an example embodiment of the present invention, a light-responsive opsin is provided for use in therapy. The opsin can be a NpHR-based molecule for use in therapy wherein the molecule is capable of responding to light by producing an inhibitory current to dissuade depolarization of a neuron and wherein the protein/molecule is capable of using an endogenous cofactor to produce the inhibitory current and manifests a toxicity level that is less than 75%, at a high expression level.

According to an example embodiment of the present invention, a light-responsive opsin is used in treating neurological diseases. The opsin can include a nucleic acid molecule comprising a nucleotide sequence encoding a NpHR based protein for use in the treatment of CNS disorders wherein said protein is capable of responding to light by producing an inhibitory current to dissuade depolarization of a neuron using an endogenous cofactor to produce the inhibitory current and manifests a toxicity level that is less than 50%, at a high expression level.

According to another example embodiment, a light-responsive opsin is used in the manufacture of a medicament for the treatment of neurological diseases. For example, an NpHR-based protein in the manufacture of a medicament for the treatment of CNS disorders wherein the said protein is capable of responding to light by producing an inhibitory current to dissuade depolarization of a neuron and is capable of using an endogenous cofactor to produce the inhibitory current and manifests a toxicity level that is less than 75%, at a high expression level.

According to another example embodiment, kit is provided for administering treatment. The kit includes, for example a product containing a first light-responsive opsin and a second-light responsive opsin as a combined preparation for simultaneous, separate or sequential use in the treatment of neurological diseases.

According to another example embodiment, a transgenic animal is produced with a light-responsive opsin expressed in one or more cells.

According to another example embodiment, cells are modified, in a live animal, using light-responsive opsins. The animal is sacrificed and the modified cells are removed for study.

Other aspects and embodiments are directed to systems, methods, kits, compositions of matter and molecules for ion pumps or for controlling inhibitory currents in a cell (e.g., in in vivo and in vitro environments).

The above summary of the present invention is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the detailed description of various embodiments of the invention that follows in connection with the accompanying drawings, in which.

Figure 1:
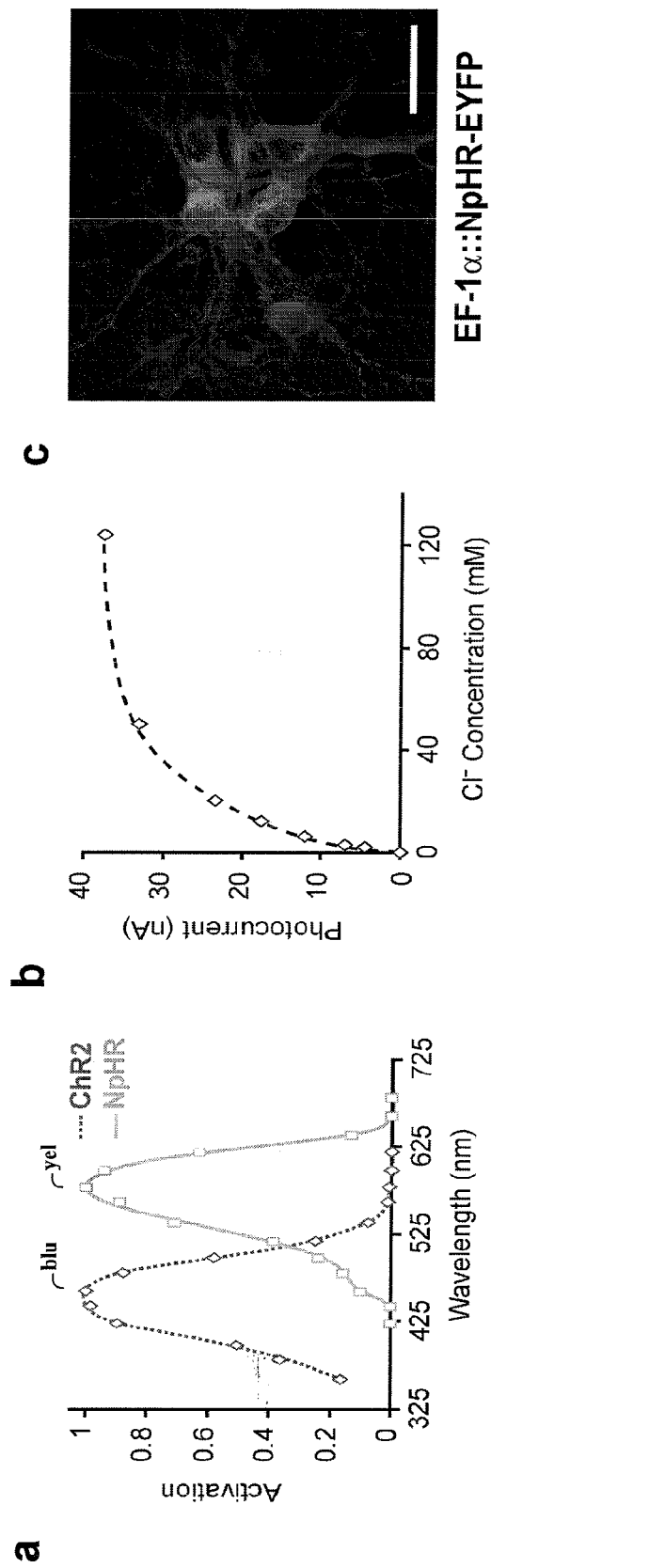
FIGS. 1A, 1B, 1C, 1D, 1E, 1F, 1G, 1H, 1I, 1J, 1K, 1L, 1M, 1N and 1O show experimental results that are consistent with an example embodiment of the present invention.
Figure 1:
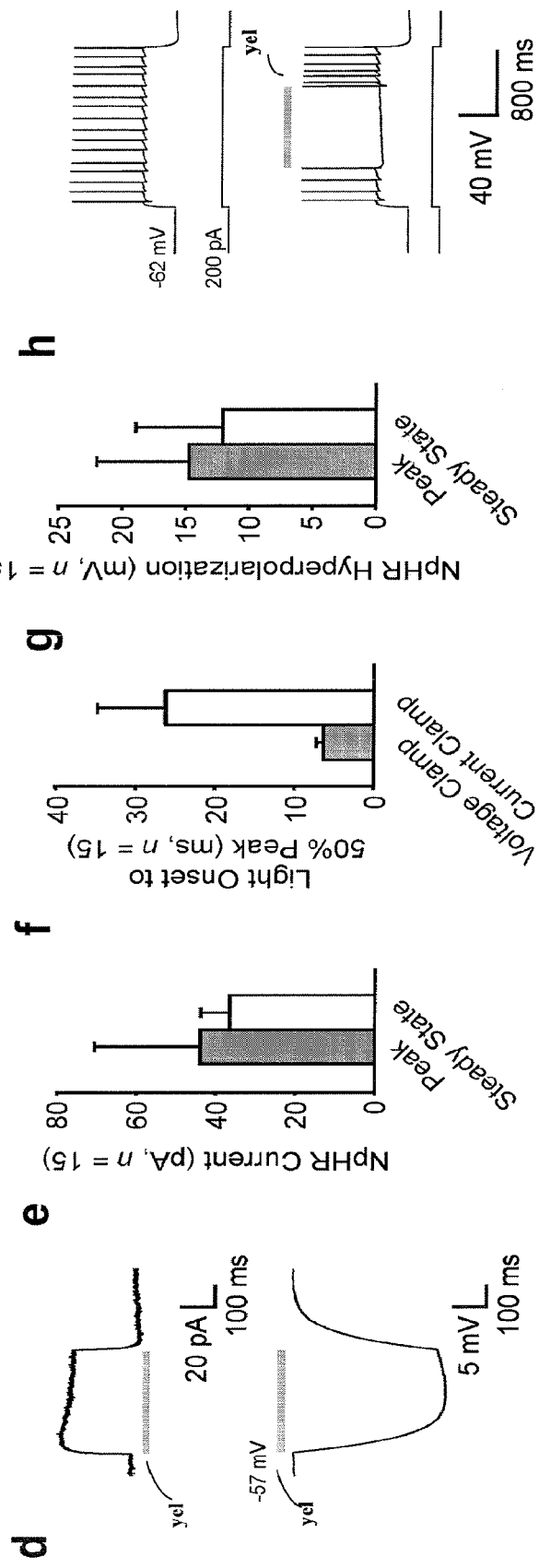
Figure 1:
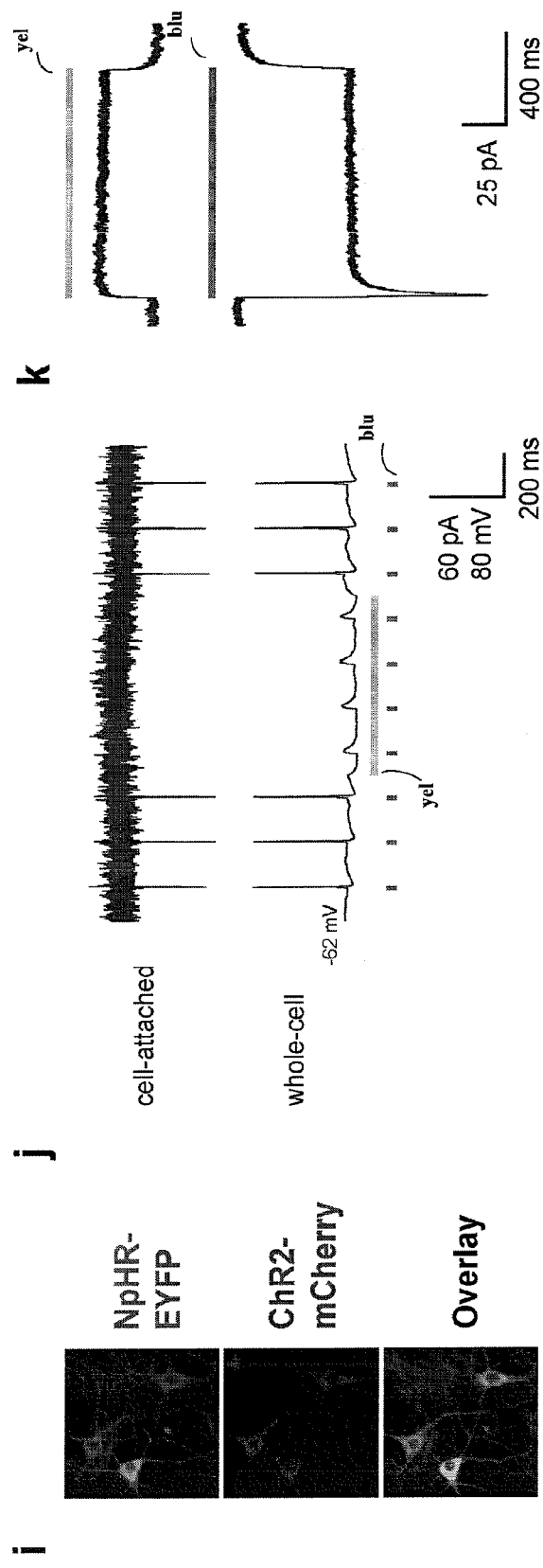
Figure 1:
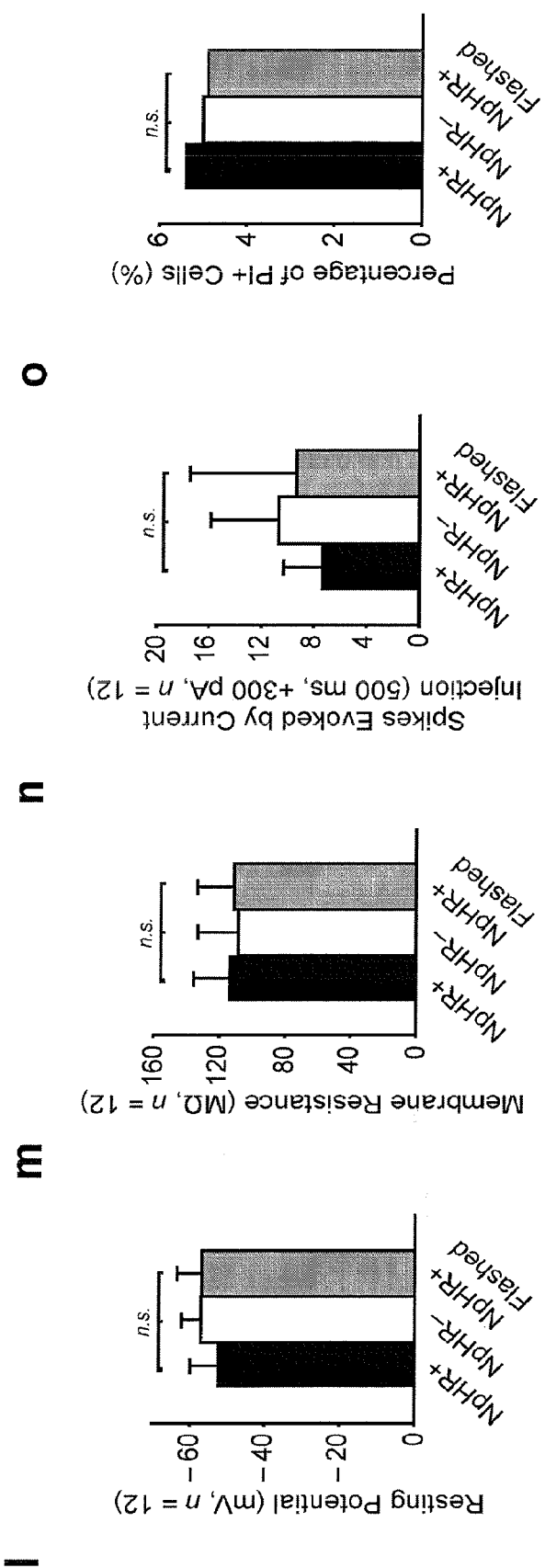

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be useful for facilitating practical application of a variety of photosensitive biomolecular structures, and the invention has been found to be particularly suited for use in arrangements and methods dealing with cellular membrane voltage control and stimulation. While the present invention is not necessarily limited to such applications, various aspects of the invention may be appreciated through a discussion of various examples using this context.

Consistent with one example embodiment of the present invention, a light-responsive protein/molecule is engineered in a cell. The protein affects a flow of ions across the cell membrane in response to light. This change in ion flow creates a corresponding change in the electrical properties of the cells including, for example, the voltage and current flow across the cell membrane. In one instance, the protein functions in vivo using an endogenous cofactor to modify ion flow across the cell membrane. In another instance, the protein changes the voltage across the cell membrane so as to dissuade action potential firing in the cell. In yet another instance, the protein is capable of changing the electrical properties of the cell within several milliseconds of the light being introduced. For details on delivery of such proteins, reference may be made to U.S. patent application Ser. No. 11/459,636 filed on Jul. 24, 2006 and entitled "Light-Activated Cation Channel and Uses Thereof", which is fully incorporated herein by reference.

Consistent with a more specific example embodiment of the present invention a protein, NpHR, from *Natronomonas pharaonis* is used for temporally-precise optical inhibition of neural activity. NpHR allows for selective inhibition of single action potentials within rapid spike trains and sustained blockade of spiking over many minutes. The action spectrum of NpHR is strongly red-shifted relative to ChannelRhodopsin-2 (ChR2) (derived from *Chlamydomonas reinhardtii*) but operates at similar light power, and NpHR functions in mammals without exogenous cofactors. In one instance, both NpHR and ChR2 can be expressed in the target cells. Likewise, NpHR and ChR2 can be targeted to *C. elegans* muscle and cholinergic motoneurons to control locomotion bidirectionally. In this regard, NpHR and ChR2 form an optogenetic system for multimodal, high-speed, genetically-targeted, all-optical interrogation of living neural circuits.

Certain aspects of the present invention are based on the identification and development of an archaeal light-driven chloride pump, such as halorhodopsin (NpHR), from *Natronomonas pharaonis*, for temporally-precise optical inhibition of neural activity. The pump allows both knockout of single action potentials within rapid spike trains and sustained blockade of spiking over many minutes, and it operates at similar light power compared to ChR2 but with a strongly red-shifted action spectrum. The NpHR pump also functions in mammals without exogenous cofactors.

According to other example embodiments of the present invention, methods for generating an inhibitory neuron-current flow involve, in a neuron, engineering a protein that responds to light by producing an inhibitory current to dissuade depolarization of the neuron. In one such method, the protein is halorhodopsin-based and in another method the protein is an inhibitory protein that uses an endogenous cofactor.

In another example embodiment, a method for controlling action potential of a neuron involves the following steps: engineering a first light responsive protein in the neuron; producing, in response to light, an inhibitory current in the neuron and from the first light responsive protein; engineering a second light responsive protein in the neuron; and producing, in response to light, an excitation current in the neuron from the second light responsive protein.

Another embodiment involves method for controlling a voltage level across a cell membrane of a cell, the method includes: engineering a first light responsive protein in the cell; measuring the voltage level across the cell membrane; and producing, in response to light of a first wavelength and using the first light responsive protein, a current across the cell membrane that is responsive to the measured voltage level.

Another aspect of the present invention is directed to a system for controlling an action potential of a neuron in vivo. The system includes a delivery device, a light source, and a control device. The delivery device introduces a light responsive protein to the neuron, with the light responsive protein producing an inhibitory current. The light source generates light for stimulating the light responsive protein, and the control device controls the generation of light by the light source.

In more detailed embodiments, such a system is further adapted such that the delivery device introduces the light responsive protein by one of transfection, transduction and microinjection, and/or such that the light source introduces light to the neuron via one of an implantable light generator and fiber-optics.

Another aspect of the present invention is directed to a method for treatment of a disorder. The method targets a group of neurons associated with the disorder; and in this group, the method includes engineering an inhibitory protein that uses an endogenous cofactor to respond to light by producing an inhibitory current to dissuade depolarization of the neurons, and exposing the neurons to light, thereby dissuading depolarization of the neurons.

According to yet another aspect of the present invention is directed to identifying and developing an archaeal light-driven chloride pump, such as halorhodopsin (NpHR), from *Natronomonas* pharaonic, for temporally-precise optical inhibition of neural activity. The pump allows both knockout of single action potentials within rapid spike trains and sustained blockade of spiking over many minutes, and it operates at similar light power compared to ChR2 but with a strongly red-shifted action spectrum. The NpHR pump also functions in mammals without exogenous cofactors.

More detailed embodiments expand on such techniques. For instance, another aspect of the present invention co-expresses NpHR and ChR2 in the species (e.g., a mouse and *C. elegans*). Also, NpHR and ChR2 are integrated with calcium imaging in acute mammalian brain slices for bidirectional optical modulation and readout of neural activity. Likewise, NpHR and ChR2 can be targeted to *C. elegans* muscle and cholinergic motoneurons to control locomotion bidirectionally. Together NpHR and ChR2 can be used as a complete and complementary opto-genetic system for multimodal, high-speed, genetically-targeted, all-optical interrogation of living neural circuits.

In addition to NpHR and ChR2, there are a number of channelrhodopsins, halorhodopsins, and microbial opsins that can be engineered to optically regulate ion flux or second messengers within cells. Various embodiments of the invention include codon-optimized, mutated, truncated, fusion proteins, targeted versions, or otherwise modified versions of such ion optical regulators. Thus, ChR2 and NpHR (e.g., GenBank accession number is EF474018 for the 'mammalianized' NpHR sequence and EF474017 for the 'mammalianized' ChR2(1-315) sequence) are used as representative of a number of different embodiments. Discussions specifically identifying ChR2 and NpHR are not meant to limit the invention to such specific examples of optical regulators. For further details regarding the above mentioned sequences reference can be made to "Multimodal fast optical interrogation of neural circuitry" by Feng Zhang, et al, Nature (Apr. 5, 2007) Vol. 446: 633-639, which is fully incorporated herein by reference.

Consistent with an example embodiment of the present invention, a method is implemented for stimulating target cells in vivo using gene transfer vectors (for example, viruses) capable of inducing photosensitive ion channel growth (for example, ChR2 ion channels). The vectors can be implanted in the body.

Consistent with a particular embodiment of the present invention, a protein is introduced to one or more target cells. When introduced into a cell, the protein changes the potential of the cell in response to light having a certain frequency. This may result in a change in resting potential that can be used to control (dissuade) action potential firing. In a specific example, the protein is a halorhodopsin that acts as a membrane pump for transferring charge across the cell membrane in response to light. Membrane pumps are energy transducers which use electromagnetic or chemical bond energy for translocation of specific ions across the membrane. For further information regarding halorhodopsin membrane pumps reference can be made to "Halorhodopsin Is a Light-driven Chloride Pump" by Brigitte Schobert, et al, The Journal of Biological Chemistry Vol. 257, No. 17. Sep. 10, 1982, pp. 10306-10313, which is fully incorporated herein by reference.

The protein dissuades firing of the action potential by moving the potential of the cell away from the action potential trigger level for the cell. In many neurons, this means that the protein increases the negative voltage seen across the cell membrane. In a specific instance, the protein acts as a chloride ion pump that actively transfers negatively charged chloride ions into the cell. In this manner, the protein generates an inhibitory current across the cell membrane. More specifically, the protein responds to light by lowering the voltage across the cell thereby decreasing the probability that an action potential or depolarization will occur.

As used herein, stimulation of a target cell is generally used to describe modification of properties of the cell. For instance, the stimulus of a target cell may result in a change in the properties of the cell membrane that can lead to the depolarization or polarization of the target cell. In a particular instance, the target cell is a neuron and the stimulus affects the transmission of impulses by facilitating or inhibiting the generation of impulses by the neuron.

As discussed above, one embodiment of the present invention involves the use of an optically responsive ion-pump that is expressed in a cell. In a particular instance, the cell is either a neural cell or a stem cell. A specific embodiment involves in vivo animal cells expressing the ion-pump. Certain aspects of the present invention are based on the identification and development of an archaeal light-driven chloride pump, such as halorhodopsin (NpHR), from *Natronomonas* pharaonic, for temporally-precise optical inhibition of neural activity. The pump allows both knockout of single action potentials within rapid spike trains and sustained blockade of spiking over many minutes, and it operates at similar light power compared to ChR2 but with a strongly red-shifted action spectrum. The NpHR pump also functions in mammals without exogenous cofactors.

According to an example embodiment of the present invention, an optically responsive ion-pump and/or channel is expressed in one or more stem cells, progenitor cells, or progeny of stem or progenitor cells. Optical stimulation is used to activate expressed pumps/channels. The activation can be used to control the ion concentrations (e.g., chloride, calcium, sodium, and potassium) in the cells. This can be particularly useful for affecting the survival, proliferation, differentiation, de-differentiation, or lack of differentiation in the cells. Thus, optical stimulus is implemented to provide control over the (maturation) of stem or progenitor cells.

In a particular embodiment, optically-controlled stimulus patterns are applied to the stem or progenitor cells over a period of hours or days. For further details regarding the effects of membrane potentials and ion concentrations on such cells reference can be made to "Excitation-Neurogenesis Coupling in Adult Neural Stem/Progenitor Cells" by Karl Deisseroth, et al, Neuron (May 27, 2004) Neuron, Vol. 42, 535-552 and to U.S. Patent Publication No. 20050267011 (U.S. patent application Ser. No. 11/134,720) entitled "Coupling of Excitation and Neurogenesis in Neural Stem/Progenitor Cells" to Deisseroth et al and filed on May 19, 2005, which are each fully incorporated herein by reference.

In a particular embodiment, a method of driving differentiation in cells is implemented. The cells are caused to express light-activated NpHR-based protein. The cells are exposed to light to activate the NpHR-based protein. The activation drives differentiation of the exposed cell or the progeny of the exposed cell.

In another embodiment, the cells comprise stem cells.

Two exemplary ion pumps originate from two strains of archaea, *Halobacterium salinarum* (HsHR) and *Natronomonas pharaonis* (NpHR). Illumination of HsHR or NpHR-expressing oocytes leads to rapid outward currents. Both HsHR and NpHR have excitation maxima near 580 nm as shown in FIG. 1A. Specifically, FIG. 1A shows the action spectrum of NpHR when measured in *Xenopus oocytes* using a Xenon short arc lamp and narrowbandwidth 20 nm filters, which is red-shifted from the known ChR2 maximum of ~460 nm. This spectral separation allows for ChR2 and an HR to be activated independently or in synchrony to effect bidirectional optical modulation of membrane potential.

In an experimental test, HsHR was found to have a lower extracellular Cl− affinity than NpHR (Km, NpHR=16 mM in FIG. 1B, Km, HsHR=32 mM) and measured currents displayed rapid rundown at low extracellular [Cl−] that did not fully recover in darkness.

The influence of cytoplasmic [Cl−] on HR pump currents was studied using excised giant patches. HR pump currents were not influenced by cytoplasmic [Cl−](from 0 to 124 mM), indicating a very low affinity for Cl− on the cytoplasmic side where Cl− ions are released, as expected since HR-mediated chloride pumping can achieve molar concentrations of cytoplasmic Cl−. The pump current exhibits more or less linear voltage dependence, and Cl− current is robust for both HRs across all physiological voltage regimes.

In one instance, a mammalian codon-optimized NpHR gene fused with enhanced yellow fluorescent protein (NpHR-EYFP) was introduced into cultured rat hippocampal CA3/CA1 neurons using lentiviruses carrying the ubiquitous EF-1α promoter (EF1α::NpHR-EYFP). Cells expressing NpHR-EYFP exhibited robust expression for weeks after infection (FIG. 1C). In voltage clamp, illumination of NpHR-EYFP cells with yellow light (bandwidth 573-613 nm via Semrock filter FF01-593/40-25; 300 W xenon lamp) induced rapid outward currents (FIG. 1D, top) with a peak level of 43.8±25.9 pA and a steady-state level of 36.4±24.4 pA (mean±s.d. reported throughout this paper, n=15; FIG. 1E). The relatively small difference between the peak and steady-state currents is believed to be indicative of rare deprotonation of the NpHR Schiff base during the pump cycle24. The rise time from light onset to 50% of the peak current is consistent across all cells (6.0±1.0 ms; FIG. 1F) with rise and decay time constants of Ton=6.1±2.1 ms and Toff=6.9±2.2 ms respectively. Light-evoked responses were never seen in cells expressing EYFP alone. In current clamp, NpHR-EYFP neurons exhibited light-evoked hyperpolarization (FIG. 1D; bottom) with an average peak of 14.7±6.9 mV and a steady-state of 12.1±6.6 mV (FIG. 1G). The delay from light onset to 50% of hyperpolarization peak was 26.0±8.6 ms (FIG. 1F) and the rise and decay time constants were Ton=35.6±15.1 ms and Toff=40.5±25.3 ms respectively. To test whether NpHR-mediated hyperpolarization could inhibit neuronal firing, current-clamped neurons were injected with a 200 pA current step for 2 s to evoke robust spike firing; concurrent light delivery abolished the evoked activity (FIG. 1H).

Images of NpHR-EYFP and ChR2-mCherry co-expressed in cultured hippocampal neurons were taken (FIG. 1I). NpHR function was probed using cell-attached recordings with ChR2 photostimulation to drive reliable spike trains. Indeed, whereas trains of blue light pulses (see "blu" in FIG. 1J) were able to evoke action potentials, concomitant yellow light illumination (see "yel" in FIG. 1J) abolished spike firing in both cell-attached and subsequent whole-cell recoding modes (FIG. 1J). After achieving the whole-cell configuration, voltage-clamp recording showed that independent exposure to yellow or blue light led to outward or inward photocurrents respectively (FIG. 1K), further confirming that ChR2 and NpHR can be combined to achieve bidirectional, independently addressable modulation of membrane potential in the same neuron. Further confirming that NpHR inhibitory function does not require a specific pipette chloride concentration under these recording conditions, it was found that NpHR-mediated inhibition is robust across a range of relevant whole-cell pipette chloride concentrations (4-25 mM) and physiologically negative resting potentials, as expected from the fact that NpHR is designed to deliver chloride ions to molar levels in the archaeal intracellular milieu.

Extensive controls were conducted to test whether heterologous expression of NpHR in neurons would alter the membrane properties or survival of neurons. Lentiviral expression of NpHR for at least 2 weeks did not alter neuronal resting potential (−53.1±6.3 mV for NpHR+ cells, −57.0±4.8 mV for NpHR− cells, and −56.7±5.7 mV for NpHR+ cells exposed to yellow light for 10 min followed by a delay period of 1 day; FIG. 1L, n=12 each) or membrane resistance (114.5±34.1 MΩ for NpHR+ cells, 108.9±20.1 MΩ for NpHR− cells, and 111.4±23 MΩ for the light-exposed NpHR+ cells; FIG. 1M, n=12 each). These electrical measurements indicated that NpHR has little basal electrical activity or passive current-shunting ability and can be acceptable regarding cell health.

The dynamic electrical properties of neurons were tested with and without NpHR. There was no significant difference in the number of spikes evoked by 500 ms current injection of 300 pA (7.5±2.8 for NpHR+ neurons, 10.7±7.9 for NpHR− neurons, and 9.3±5.1 for the light-exposed NpHR+ neurons; FIG. 1N).

To assess cell survivability, both live NpHR+ neurons (with and without light exposure) and NpHR− neurons were stained with the membrane-impermeant DNA-binding dye propidium iodide to assess cell survival. NpHR expression did not affect the percentage of neurons that took up propidium iodide (13/240 for NpHR+ cells, 7/141 for NpHR− cells, and 10/205 for the light-exposed NpHR+ cells; FIG. 1M, P>0.999 by $\chi^2$ test). These experiments indicated that NpHR expression does not significantly affect the health or basal electrical properties of neurons.

The tunability of NpHR efficacy with different intensities of delivered light was measured using a 200 pA current step that drove reliable action potential trains. It was discovered that maximal light intensity of 21.7 mW/mm2 under a 40×, 0.8 NA water-immersion objective inhibited 98.2±3.7% of the spikes.

Figure 2:
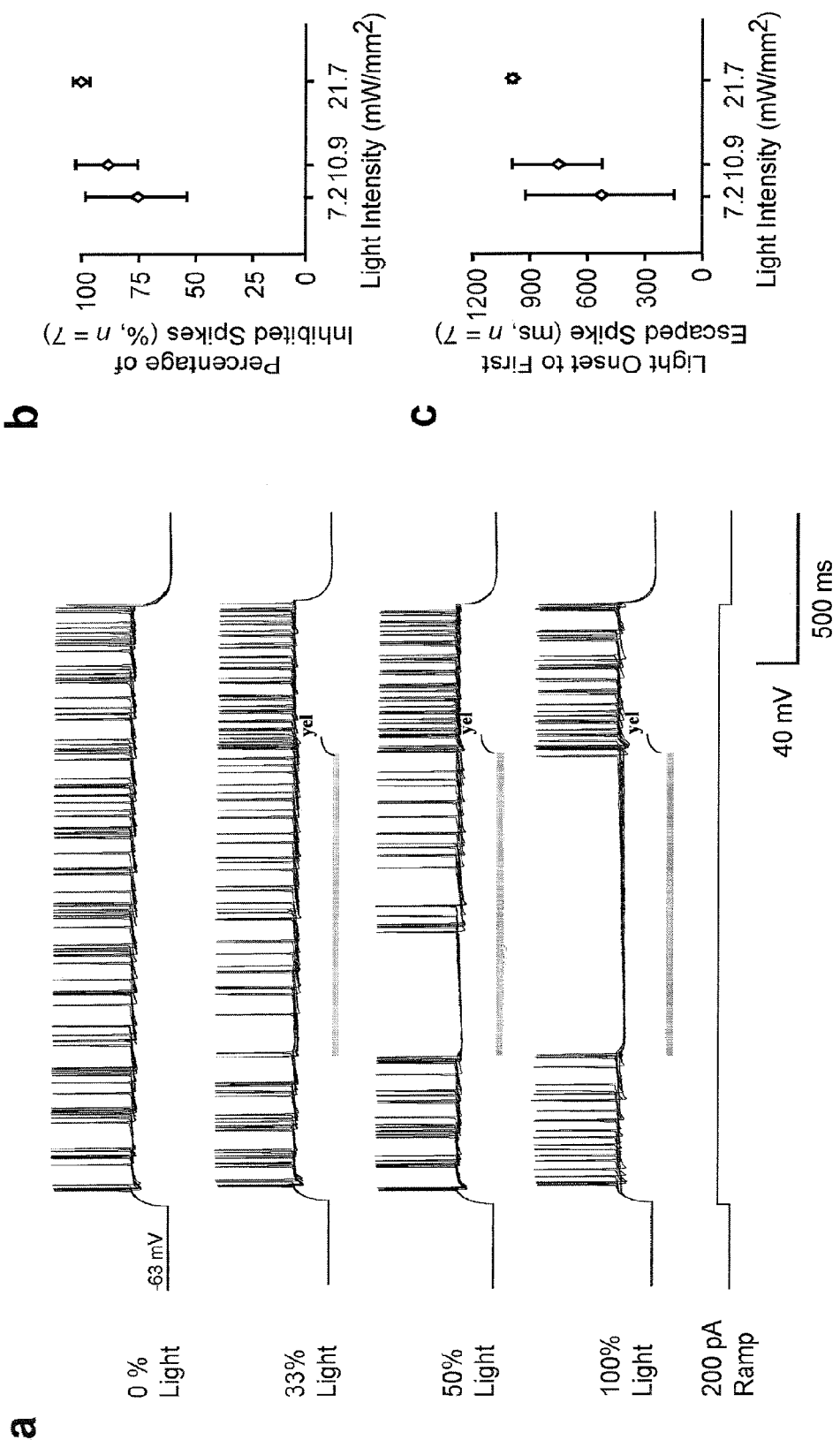
FIGS. 2A, 2B, 2C, 2D, 2E and 2F show experimental results that are consistent with an example embodiment of the present invention.
Figure 2:
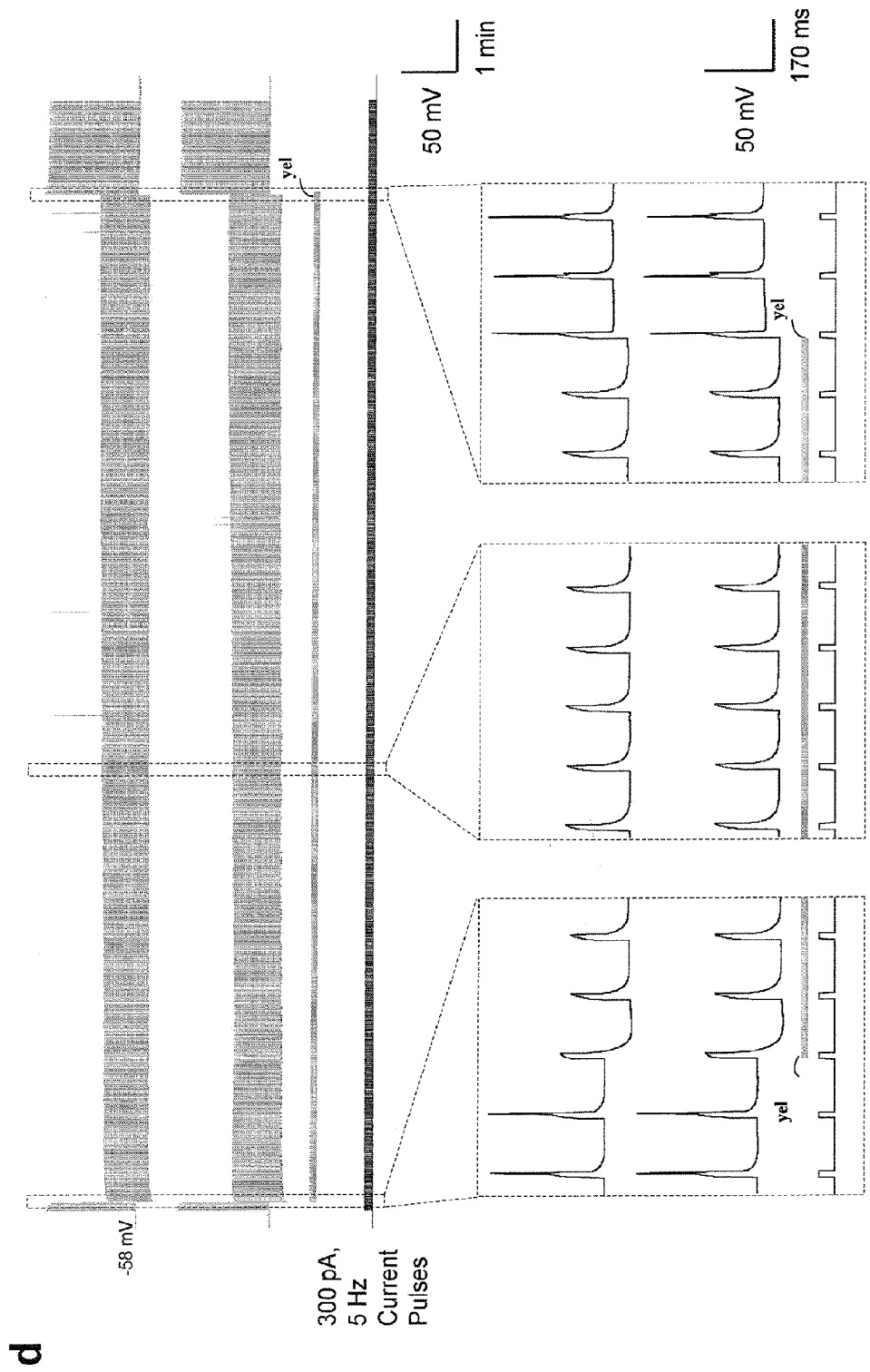
Figure 2:
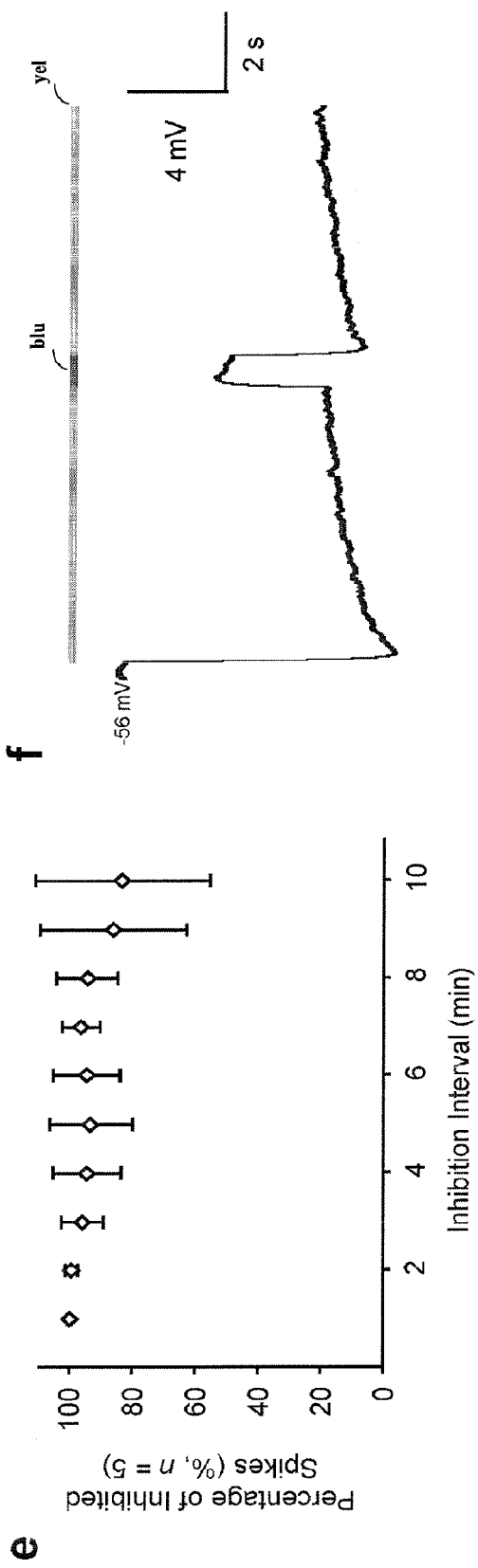

Using a 200 pA current step to drive reliable action potential trains, a maximal light intensity of 21.7 mW/mm$^2$ under 40×, 0.8 NA water-immersion objective inhibited 98.2±3.7% of spikes (FIGS. 2A and 2B). Using 33% or 50% of the full light intensity inhibited 74.9±22.2% and 87.3±13.5% of spikes, respectively (FIG. 2B). FIG. 2C shows that with steady current injection, lower intensities of light were effective for a shorter period of time; the delays from light onset to the first escaped spike under 33%, 50% and 100% light intensity were 533.65±388.2 ms, 757.5±235.5 ms, and 990.5±19.1 ms, respectively. Therefore inhibition is likely to be more effective early in the light pulse, presumably due to the slight inactivation of NpHR. Except where otherwise noted, the remaining experiments were conducted with 21.7 mW/mm2 yellow light delivered to the neurons.

Using trains of brief current pulses to generate spike trains, NpHR was tested for mediation of both long-term inhibition (to emulate lesions on the timescale of seconds to minutes) and short-term inhibition (to modify spike firing on the millisecond timescale). For long-term inhibition NpHR was tested over 10 min by injecting 300 pA current pulses at 5 Hz to drive steady action potential firing. Concurrent yellow light was delivered continuously for 10 minutes. NpHR mediated inhibition of spike trains remained effective over many minutes as shown by FIG. 2D. 99.0±1.9% of spikes were inhibited within the first two minutes while over 90% of spikes were inhibited for up to 8 minutes as shown in FIG. 2E, with n=5. The slight decrease in efficacy is likely due to accumulation of non-functional NpHRs with a deprotonated Schiff base over long periods of light exposure. While natural reprotonation of the Schiff base is slow, any non-functional NpHRs can be readily and quickly restored via brief illumination with blue light as shown by FIG. 2F.

Figure 3:
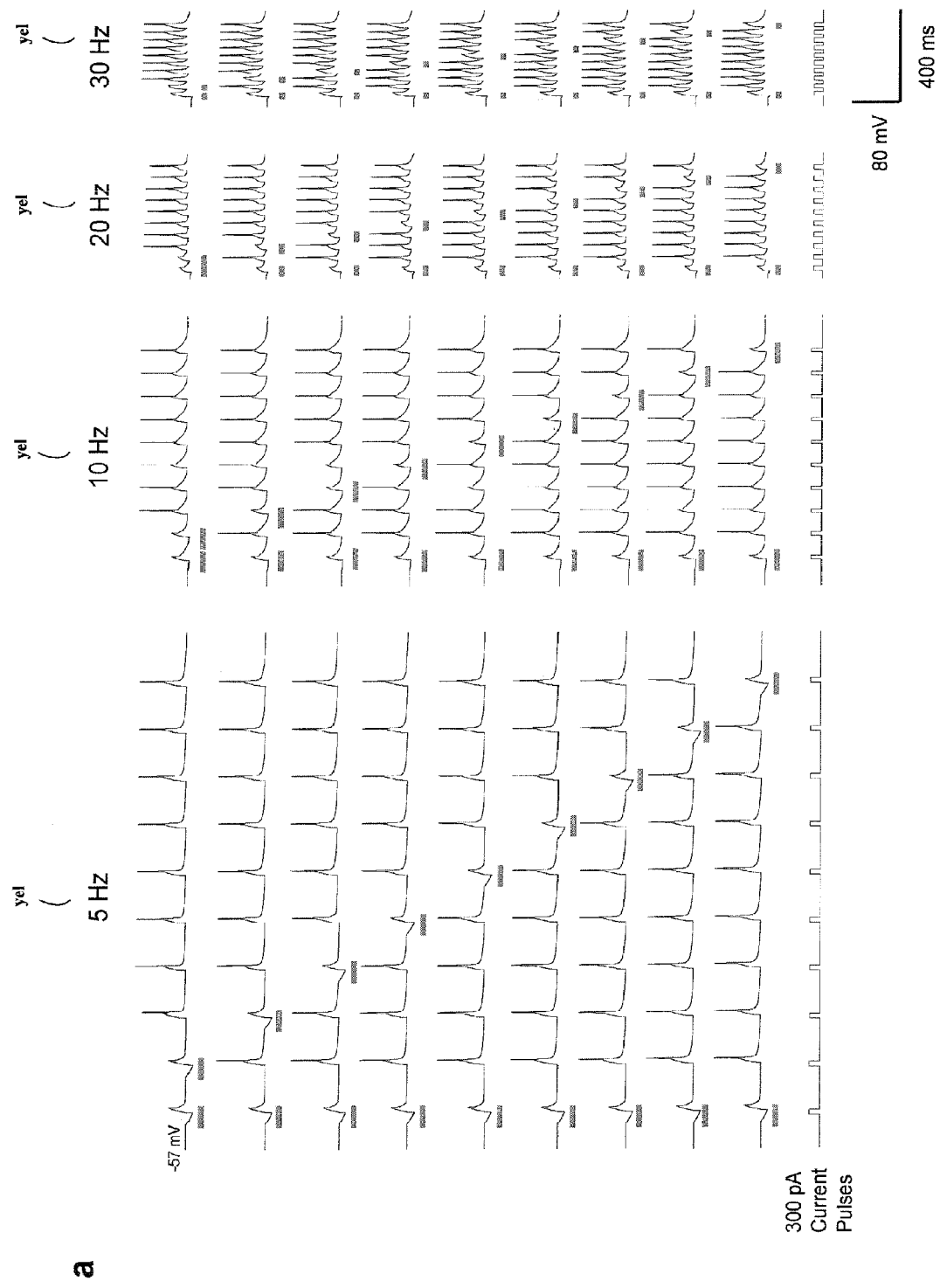
FIGS. 3A, 3B, 3C, 3D, 3E and 3F, show experimental results that are consistent with an example embodiment of the present invention.
Figure 3:
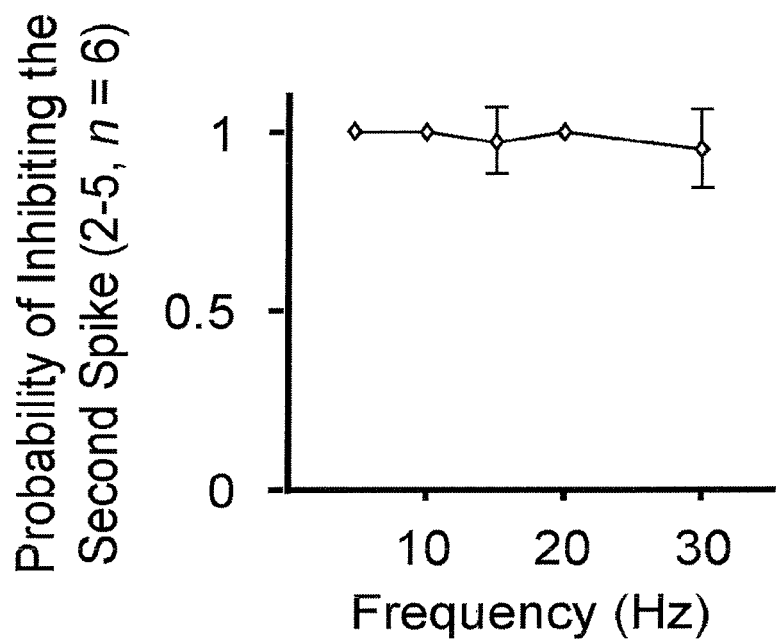
Figure 3:
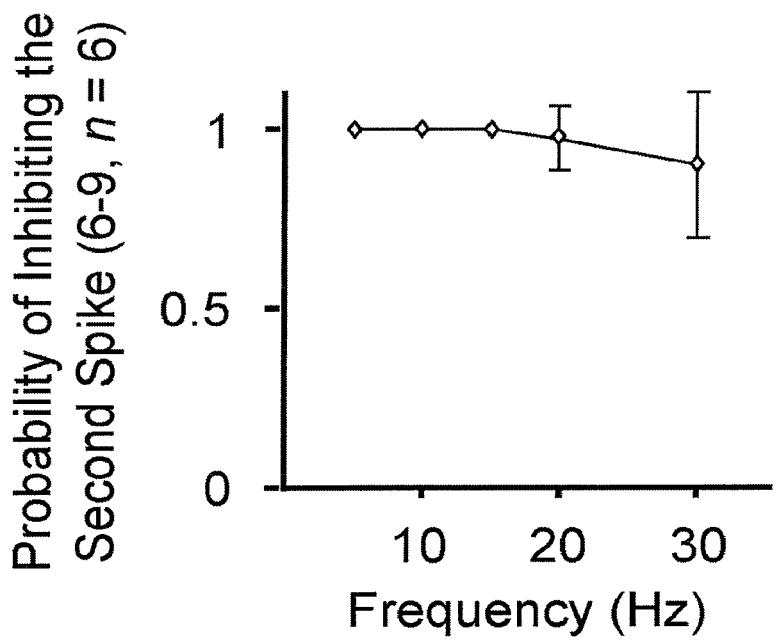
Figure 3:
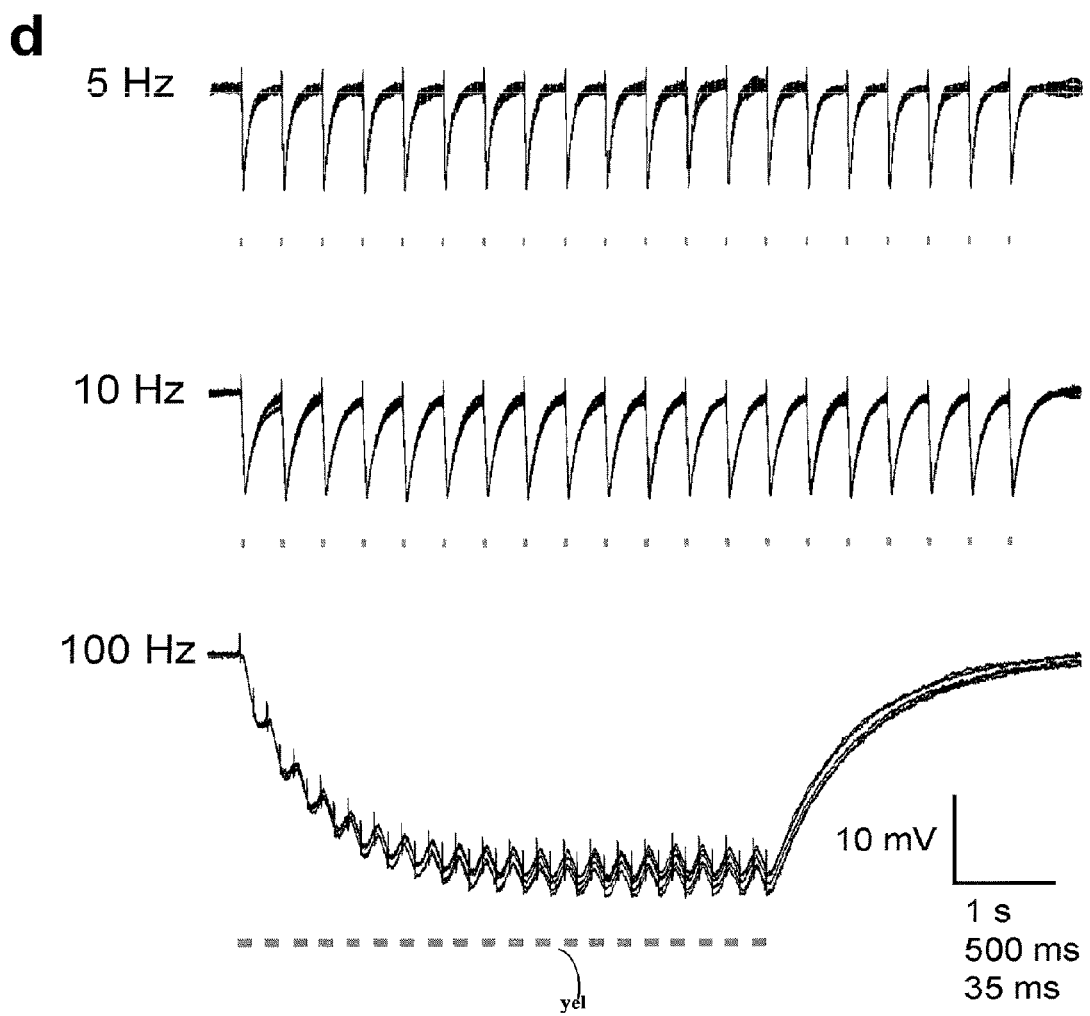
Figure 3:
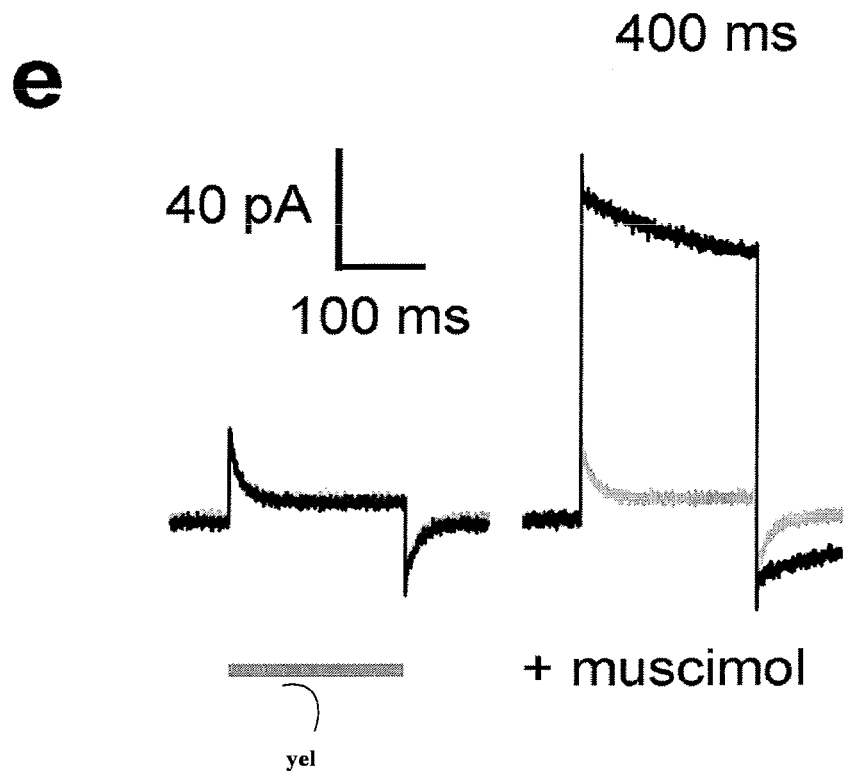
Figure 3:
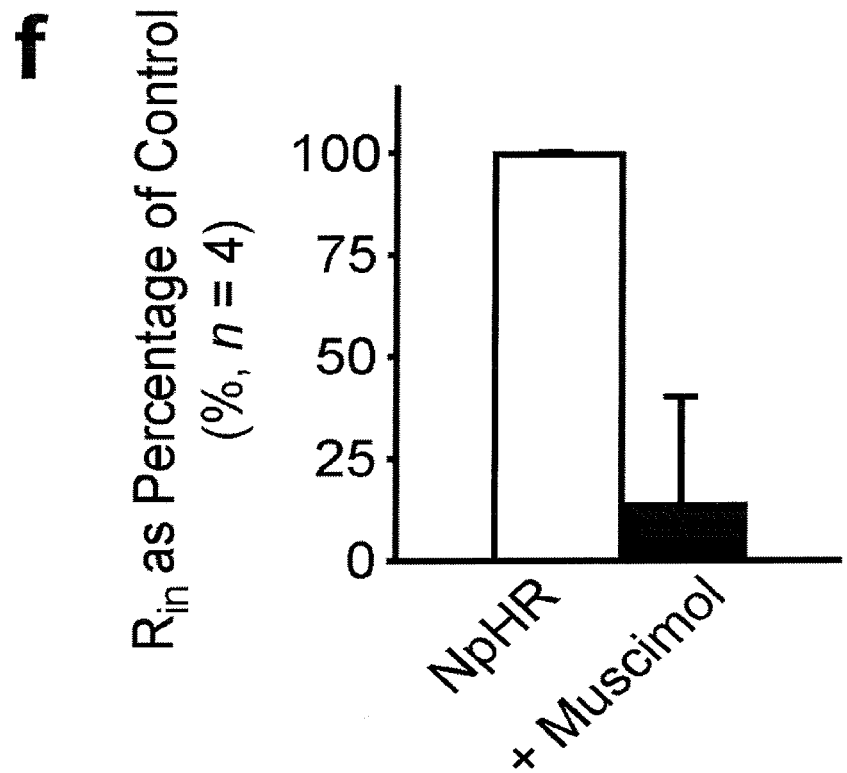

NpHR activation was tested for the ability to allow the "knockout" of single action potentials. The fast photocurrent of ChR2 enables brief pulses of blue light to drive reliable action potential trains. Concurrently applied brief pulses of yellow light were used to test NpHR-mediated inhibition. FIG. 3A shows the results of an attempt to inhibit pairs of spikes in action potential trains of 5, 10, 20, and 30 Hz. Indeed, single spikes could be reliably inhibited from within longer spike trains. Several pairs of spikes within a range of inter-spike temporal delays were inhibited in an effort to define the temporal precision of NpHR. FIGS. 3A, 3B and 3C show that both closely timed and temporally separated spike pairs were able to be reliably inhibited, while sparing spikes between the targeted times (n=6). Over spike rates of 5 to 30 Hz, the closely timed spikes could be selectively inhibited with a probability of 0.95 or greater. Moreover, FIG. 3D shows that by giving trains of millisecond-scale yellow light pulses, it is straightforward to simulate barrages of IPSP-like events with precise, reliable timing and amplitudes, from 5 to 100 Hz.

Since NpHR is a Cl– pump and not a channel, the light-driven inhibition acts by shifting the membrane potential and will not contribute (significantly) to shunting or input resistance changes. FIGS. 3E and 3F show that, whereas the $GABA_A$ chloride channel agonist muscimol significantly decreased neuronal input resistance, NpHR activation had no detectable effect on the input resistance.

Since both ChR2 and NpHR can be activated with high temporal precision using millisecondscale blue or yellow light pulses, an experiment was implemented to test the possibility of driving both proteins in intermingled temporally precise patterns. Such ability can be useful to noninvasively activate or inhibit single identified action potentials with light in the same experiment or even in the same cell. Cell attached and whole-cell recordings in hippocampal pyramidal neurons revealed that precisely patterned trains of yellow and blue light pulses can be used to evoke and inhibit neural activity with single spike precision, and that NpHR can be used to override multiple preselected ChR2-driven spikes at identified positions in prolonged spike trains.

Both NpHR and ChR2 can be functionally expressed in the mammalian brain without exogenous delivery of its required cofactor all-trans-retinal (ATR), presumably due to the presence of endogenous retinoids in the mammalian brain. As an experiment, lentiviruses carrying NpHR-EYFP were delivered under the neuronal CaMKIIα promoter into the hippocampus of the adult mouse. Neurons throughout the hippocampus exhibited stable expression of NpHR-EYFP, as indicated by a robust EYFP fluorescence.

NpHR-EYFP cells in acute hippocampal slices exhibited voltage clamp photocurrents similar to those observed in cultured neurons. A current clamp recording of NpHR-EYFP neurons revealed that temporally precise patterns of spike inhibition could be achieved readily as in dissociated culture. No exogenous cofactors were delivered at any point, indicating that NpHR can be functionally applied to mammalian systems in vivo.

In another instance, NpHR/ChR2 was combined in a system by expressing in living mammalian neural circuitry, with fura-2 calcium imaging, in an all-optical experiment. Lentiviruses carrying ChR2-mCherry under the neuron-specific CaMKIIα promoter and NpHR-EYFP under the EF-1α promoter were injected into the brain of postnatal d4 mouse pups; acute cortical slices were prepared at postnatal d10-14 and labeled with fura-2-AM. In neurons co-expressing ChR2-mCherry and NpHR-EYFP, initial simultaneous illumination with both blue and yellow light did not lead to [Ca2+] transients while subsequent pulsed blue light alone in the same neurons evoked ChR2-triggered [Ca2+] transients. This demonstrates that NpHR and ChR2 can be integrated to achieve multimodal, bidirectional control of neural activity in intact tissue. In the same imaged cells (where ChR2 stimulation led to a 3.1±0.3% increase in ΔF/F), the combination of NpHR and ChR2 activation resulted in a 0.0±0.2% effect on ΔF/F (n=6, P<0.0001). Yellow illumination alone had no detectable effect on [Ca2+]. Since not all targeted cells are necessarily affected to the same degree, this optical system could complement electrophysiology to probe successful modulation of the targeted cell population. Thus, according to one embodiment, the combination of ChR2 and NpHR with calcium imaging provides an all-optical system for interrogation of neural circuits.

Another set of experiments were conducted to show control of animal behavior in vivo. An in vivo experiment involved expression of NpHR-ECFP fusion protein in the body wall muscles of the nematode *Caenorhabditis elegans* using the muscle-specific myosin promoter (Pmyo-3). ECFP fluorescence could be readily observed throughout muscle cells and membranous muscle arm extensions. As worms (unlike mammals) appear not to have sufficient levels of endogenous retinoids, transgenic animals expressing NpHR in muscle were grown in medium containing ATR. Whole-cell voltage-clamp recordings from dissected muscles indeed demonstrated light-evoked outward currents (265±82 pA, n=9). To test effects on muscle activity, swimming behavior in liquid medium was analyzed. Consistent with the photocurrents observed, photoactivation of NpHR immediately (within ~150 ms) and essentially completely arrested swimming behavior. Transgenic animals, raised in the absence of ATR and wild type animals raised with and without ATR, were used as controls. Robust paralyzing effects of light were observed, but consistently only in transgenic animals raised in the presence of ATR.

When transgenic muscle-expressing animals were illuminated for 1 second, they quickly returned to their natural swimming rate after light stimulus termination. When NpHR was activated in muscle for 10 seconds, animals remained uncoordinated for prolonged periods (up to 40 seconds), before a full recovery became apparent and normal swimming commenced.

Another experiment involved targeting of NpHR to a specific class of genetically defined neurons in vivo. NpHR-ECFP was expressed in cholinergic motoneurons using the vesicular acetylcholine transporter promoter (Punc-17). When illuminated for 1 or 10 seconds, respectively, these animals also strongly reduced or essentially stopped swimming behavior. These animals, in contrast to the muscle targeted individuals, recovered to normal swimming behavior immediately, perhaps indicating more powerful Cl− homeostasis in neurons than in muscles, although in all cases full recovery was observed consistent with the lack of toxicity observed in mammalian neurons. When illuminated on solid agar substrate, transgenic animals expressing NpHR either in muscle, or in cholinergic motoneurons, exhibited rapid inhibition of movement and relaxed their bodies, resulting in overall elongation by up to 9% within ~600 ms of illumination.

ChR2 and NpHR were found to be able to be driven simultaneously in C. elegans. With either muscle or targeted cholinergic neuron expression (using the Pmyo-3 or Punc-17 promoters, respectively), NpHR rapidly and reversibly counteracted the shortening behavior observed with ChR2 alone. These experiments demonstrate that acetylcholine release can be efficiently triggered from C. elegans motoneurons using ChR2, and that ChR2 and NpHR work well together in nematodes as well as mammals. In some instances, such an NpHR/ChR2 system enables rapid bidirectional control of neurons on the timescale of milliseconds, thus enabling emulation or alteration of the neural code. These fast genetically based neural spike-controlling technologies powerfully augment existing tools for interrogating neural systems. Indeed, integration of the NpHR/ChR2 neural control system with optical activity markers like fura-2, and with GFP-based morphological markers, delivers a versatile triad of technologies for watching, listening to, and controlling living neural circuitry with light.

Both NpHR and ChR2 can be functionally expressed and operate at high speed in the mammalian brain without necessitating cofactor addition. Moreover, NpHR and ChR2 function in behaving C. elegans as well after simple dietary ATR supplementation. When combined with optical imaging or behavioral measures in intact tissue or freely moving animals, the NpHR/ChR2 system provides the capability to directly and causally link precisely defined patterns of neural activity with specific circuit behaviors.

The ability to use light to inhibit or activate neurons has practical applications beyond basic science investigations. The NpHR/ChR2 system may be genetically targeted to specific classes of neurons or other excitable cells involved in disease processes to enable highly precise optical therapeutic treatments. For example, in Parkinson's disease where electrode-based deep brain stimulation (DBS) can be therapeutic for symptomatic relief but also gives rise to side effects, delivery of these optogenetic tools targeted by cell type-specific promoters to distinct disease-related neuronal types may ultimately provide a more precise alternative with fewer side-effects. Whether in basic science or clinical applications, the spectral separation between the NpHR and ChR2 activation maxima allows for the first time bidirectional optical control in the same target tissue, and permits both sufficiency and necessity testing in elucidation of the roles of specific cell types in high-speed intact circuit function.

Oocyte microinjection and physiology were experimentally carried out using the following procedures. NpHR cRNA was generated using the T7-cap scribe kit from Ambion (Austin, Tex.). Stage V/VI oocytes were prepared. Each oocyte was injected with 30 to 50 ng cRNA, incubated for 4 to 7 days at 16 to 18° C. with 1 µM ATR in the medium (90 mM NaCl, 2 mM KCl, 1 mM MgCl2, 1.8 mM CaCl2, 5 mM HEPES, pH 7.4/NaOH) to reconstitute functional HR. As a control uninjected oocytes were incubated in the same medium. Oocytes were recorded using two-electrode voltage-clamp (Turbo Tec-05) and illuminated with a continuous He—Ne laser (594 nm, LYHR-0600M, Laser 2000, Wessling, Germany). The maximum light intensity was 3 mW/mm$^2$ and was focused to a diameter close to the dimensions of the oocyte. In giant patch experiments from halorhodopsin-expressing oocytes a continuous He—Ne laser of 633 nm with light intensities up to 400 mW/mm2 was used.

Figure 9:
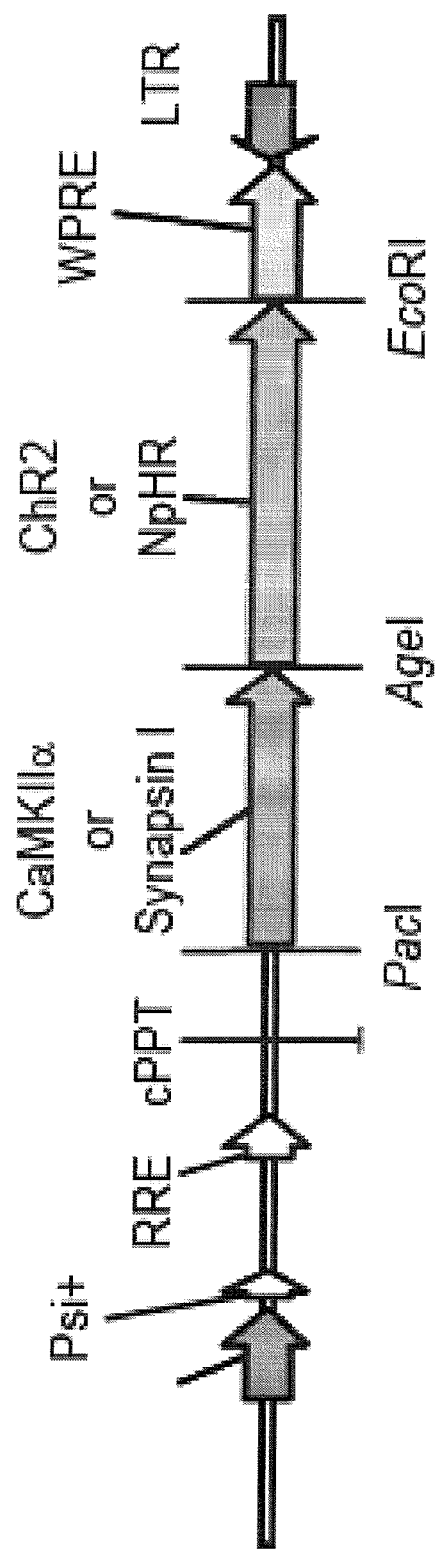
FIG. 9 shows Lentiviral vector construction, according to an example embodiment of the present invention.

Lentiviral vector construction was experimentally carried out using the following procedures. Lentiviral vectors containing Synapsin I::ChR2-mCherry, CaMKIIα::ChR2-mCherry, and CaMKIIα::NpHR-EYFP were based on the FCK(1.3)GW plasmid. For the construction of these lentiviral vectors, the promoter was PCR amplified and cloned into the PacI and AgeI restriction sites (FIG. 9). The transgene ChR2-mCherry or NpHR-EYFP were PCR amplified and cloned into the AgeI and EcoRI restriction sites. The pLEHYT vector is constructed in the same way as pLECYT3 by inserting the NpHR-EYFP gene into the AfeI and SpeI restriction sites of pLEGT.

For both NpHR-EYFP and ChR2-mCherry, the protein fusion was made via a NotI restriction site. The linker between the two proteins is 5'-GCGGCCGCC-3'. The start codon on the fluorescent protein was removed deliberately to avoid translation of the fluorescent protein alone. In addition to the promoter, each lentiviral vector contains the HIV-1 central polypurine tract (cPPT) and the Woodchuck Hepatitis Virus Post-transcriptional Regulatory Element (WPRE) to improve transduction efficiency.

Lentiviral production and transduction were experimentally carried out using the following procedures. High-titer lentiviruses were produced using a second generation lentiviral system, by cotransfection of 293FT cells (Invitrogen) with pCMVΔR8.74 and pMD2.G in addition to the viral vector. The following protocol was used.

Day 0: Split 4 T-225 flasks (Nunc) of 95% confluent 293FT cells into one 4 layer CellFactory (Nunc). Culture using 500 mL of DMEM with 10% FBS. Incubate the plates at 37° C. overnight. The cells should reach 90% confluence in 24 hours.

Day 1: Perform calcium phosphate transfection; make DNA mixture containing 690 µg of the viral vector, 690 µg of pCMVΔR8.74, and 460 µg of pMD2.G. Add 5.7 mL of 2M CaCl2 to the DNA mixture and bring the total volume to 23.75 mL with distilled H2O; then, quickly combine the DNA/CaCl2 solution with 23.75 mL of 2×HBS (50 mM HEPES, 1.5 mM Na2HPO4, 180 mM NaCl, pH 7.05; note that the pH is important); after quickly mixing by inverting 5 times, add the DNA/CaCl2/HBS solution to 500 mL of room-temperature DMEM with 10% FBS to make the transfection media; then, exchange the media in the CellFactory with the transfection media.

Day 2: 15 hours from the time of transfection, remove the transfection media from the CellFactory and wash the cells 3 times with fresh room-temperature DMEM; incubation longer than 15 hours may lead to cell death and reduced viral titer; finally, replace the media with 500 mL of fresh DMEM containing 10% FBS and incubate in a 37° C. incubator for 9 hours.

Day 2.5: 24 hours from the time of transfection, remove the media from the CellFactory and replace with 200 mL of serum-free media (UltraCULTURE, Cambrex) containing 5 mM Sodium Butyrate; return the CellFactory to the incubator.

Day 3: 40 hours from the time of transfection, collect the 200 mL of media from the CellFactory. This is the viral-containing supernatant. Centrifuge at 1000 rpm for 5 minutes to precipitate large cell debris and then filter the viral supernatant using a 0.45 µm low-protein binding filter flask. Then, centrifuge the supernatant using a SW-28 rotor (Beckman Coulter) for 2 hours at 55,000×g to precipitate the virus. Usually 6 centrifuge tubes are required to concentrate all of the viral supernatant. Before spinning, add 2 mL of PBS containing 20% sucrose to the bottom of the centrifuge tube to remove any remaining cell debris during centrifugation. After centrifugation, gently decant the liquid from the centrifuge tubes and re-suspend all 6 viral pellets with 100 µL of 4° C. PBS. Then, aliquot the viral solution and store at −80° C. for future use. If desired, 10 mL of unconcentrated viral supernatant can be stored before centrifugation for in vitro use in cultured neurons. For culture applications, neurons can be transduced simply by adding 50 µL of unconcentrated viral supernatant per 24-well plate well. Protein expression can be observed 4 to 5 days later. For in vivo applications, concentrated virus can be directly injected into the mammalian brain.

For whole-cell and cell-attached recording in cultured hippocampal neurons or acute brain slices, three intracellular solutions containing 4 mM chloride were prepared (135 mM K-Gluconate, 10 mM HEPES, 4 mM KCl, 4 mM MgATP, 0.3 mM Na3GTP, titrated to pH 7.2), 10 mM chloride (129 mM K-Gluconate, 10 mM HEPES, 10 mM KCl, 4 mM MgATP, 0.3 mM Na3GTP, titrated to pH 7.2), or 25 mM chloride (114 mM K-Gluconate, 10 mM HEPES, 25 mM KCl, 4 mM MgATP, 0.3 mM Na3GTP, titrated to pH 7.2).

For cultured hippocampal neurons, Tyrode's solution was employed as the extracellular solution (125 mM NaCl, 2 mM KCl, 3 mM CaCl2, 1 mM MgCl2, 30 mM glucose, and 25 mM HEPE, titrated to pH 7.3).

For preparation of acute brain slices, mice were sacrificed 2 weeks after viral injection. 250 µm acute brain slices were prepared in ice-cold cutting solution (64 mM NaCl, 25 mM NaHCO3, 10 mM glucose, 120 mM sucrose, 2.5 mM KCl, 1.25 mM NaH2PO4, 0.5 mM CaCl2, 7 mM MgCl2, and equilibrated with 95% o2/5% CO2) using a vibratome (VT1000S, Leica). Slices were incubated in oxygenated ACSF (124 mM NaCl, 3 mM KCl, 26 mM NaHCO3, 1.25 mM NaH2PO4, 2.4 mM CaCl2, 1.3 mM MgCl2, 10 mM glucose, and equilibrated with 95%+O2/5% CO2) at 32° C. for 30 min to recover.

For calcium imaging, lentiviruses were injected into the cortex of C57BL/6 mice at postnatal day 4 or 5 and acute brain slices were prepared 7 to 8 days later for adult mice.

Transgenic C. elegans Lines and Transgenes were experimentally developed using the following procedures. The NpHR gene was placed under the muscle-specific myo-3 promoter (untagged NpHR in transgene zxEx29[pmyo-3::NpHR; lin-15+] and NpHR-ECFP in transgene zxEx3O [pmyo-3::NpHR-ECFP; rol-6d]) or under the cholinergic motoneuron specific unc-17 promoter (NpHRECFP in transgene zxEx33[punc-17::NpHR-ECFP; lin-15+]). The NpHR-ECFP fusion (zxEx30 and zxEx34, see below) was employed to assess expression pattern. NpHR-ECFP (zxEx30) animals showed light induced effects that were comparable to the untagged version (zxEx29).

For co-activation of ChR2/NpHR in muscles or cholinergic motoneurons, transgenes zxEx32[pmyo-3::NpHR; pmyo-3::ChR2(H134R)-EYFP; lin-15+] and zxEx34[punc-17::NpHRECFP; punc-17::ChR2(gf)-YFP; rol-6d] were used. Table 1 lists examples of transgenes and worm lines used in various experimental tests.

TABLE 1

| Transgene | Genotype | Strain |
|---|---|---|
| zxEx29 [p myo-3::NpHR; lin-15+] | lin-15 (n765ts−) | ZX396 |
| zxEx30 [p myo-3::NpHR-ECFP; rol-6d] | N2 | ZX397 |
| zxEx32 [p myo-3::NpHR; p myo-3::ChR2(H134R)-EYFP; lin-15+] | lin-15 (n765ts−) | ZX399 |
| zxEx33 [p unc-17::NpHR-ECFP; lin-15+] | lin-15 (n765ts−) | ZX416 |
| zxEx34 [p unc-17::NpHR-ECFP; p unc-17:: ChR2(H134R)-EYFP; rol-6d] | N2 | ZX417 |

Experimental tests for bidirectional optical neural control and in vivo implementation were implemented. NpHR in muscle were grown in medium containing ATR. Whole-cell voltage-clamp recordings from dissected muscles indeed demonstrated light-evoked outward currents (265±82 pA, n=9). To test effects on muscle activity, swimming behavior in liquid medium was analyzed. Consistent with the photocurrents observed, photoactivation of NpHR immediately (within ~150 ms) and essentially completely arrested swimming behavior. As controls, transgenic animals that were raised in the absence of ATR, and wild type animals that were raised with and without ATR were used. Robust paralyzing effects of light were observed, but consistently only in transgenic animals raised in the presence of ATR. When muscle-expressing animals were illuminated for 1 s, they quickly returned to their natural swimming rate after light stimulus termination. When NpHR was activated in muscle for 10 s, animals remained uncoordinated for prolonged periods (up to 40 seconds), before a full recovery became apparent and normal swimming commenced.

Next, NpHR was targeted to a specific class of genetically defined neurons in vivo. NpHR-ECFP was expressed in cholinergic motoneurons using the vesicular acetylcholine transporter promoter (Punc-17). When illuminated for 1 or 10 s, respectively, these animals also strongly reduced or essentially stopped swimming behavior. These animals, in contrast to the muscle-targeted individuals, recovered to normal swimming behavior immediately, perhaps indicating more powerful Cl− homeostasis in neurons than in muscles, although in all cases full recovery was observed consistent with the lack of toxicity observed in mammalian neurons.

When illuminated on solid agar substrate, transgenic animals expressing NpHR either in muscle, or in cholinergic motoneurons, exhibited rapid inhibition of movement and relaxed their bodies, resulting in overall elongation by up to 9% within ~600 ms of illumination. It was found that ChR2 and NpHR could be driven simultaneously in C. elegans as well. With either muscle or targeted cholinergic neuron expression (using the Pmyo-3 or Punc-17 promoters, respectively), NpHR rapidly and reversibly counteracted the shortening behavior observed with ChR2 alone. These experiments demonstrate that acetylcholine release can be efficiently triggered from C. elegans motoneurons using ChR2, and that ChR2 and NpHR work well together in nematodes as well as mammals.

Slides were developed showing cell-attached (FIG. 4A left) and whole-cell (FIG. 4A right) recording of cultured hippocampal neurons co-expressing ChR2-mCherry and NpHR-EYFP. Action potentials were evoked via trains of blue light pulses (5 Hz trains, 15 ms pulse width, lowest set of bars). NpHR-mediated inhibition was co-administered by brief yellow light pulses (50 ms pulse width, upper sets of bars).

Figure 4:
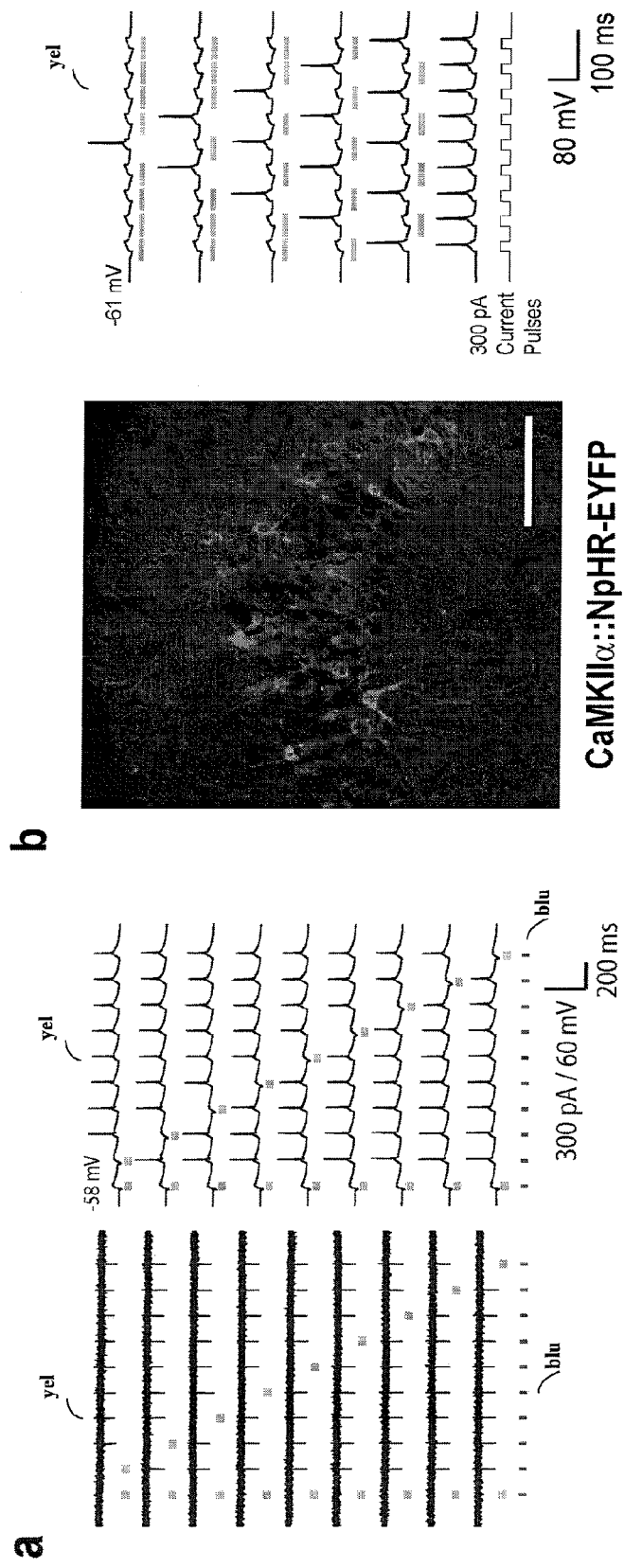
FIGS. 4A, 4B, 4C, 4D, 4E, 4F, 4G and 4H, show experimental results that are consistent with an example embodiment of the present invention.
Figure 4:
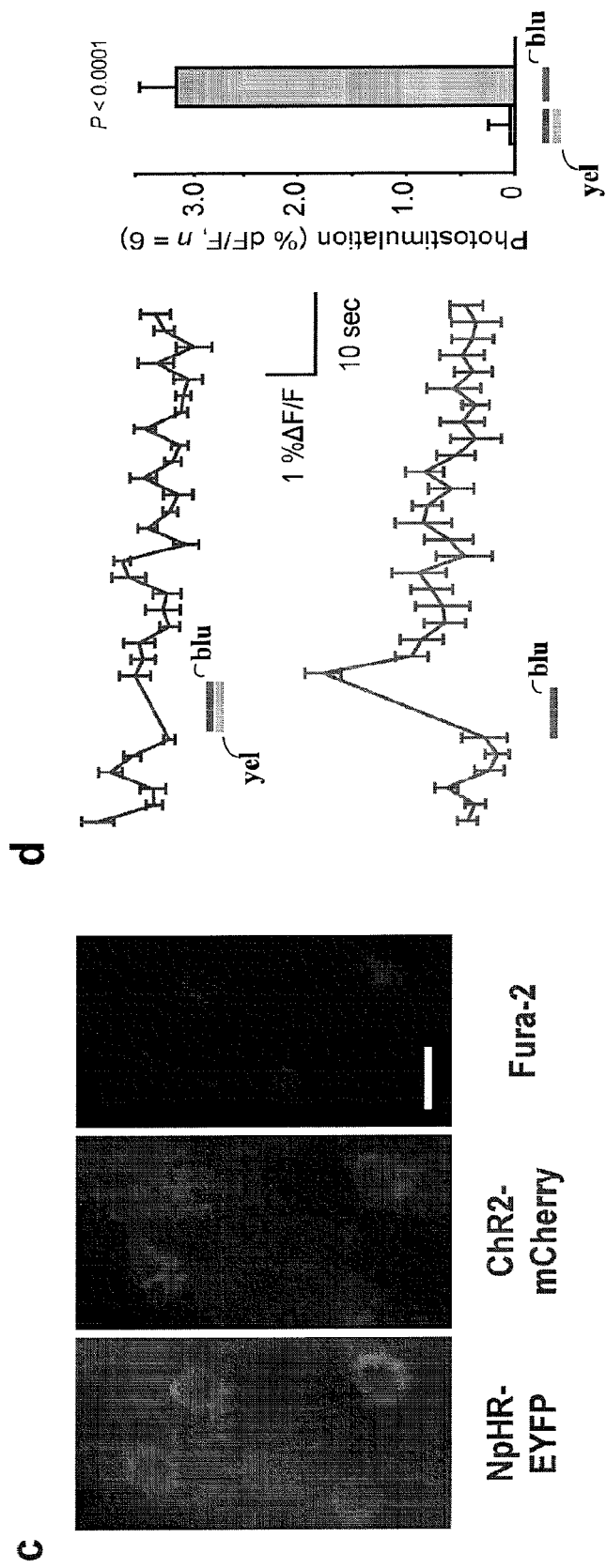
Figure 4:
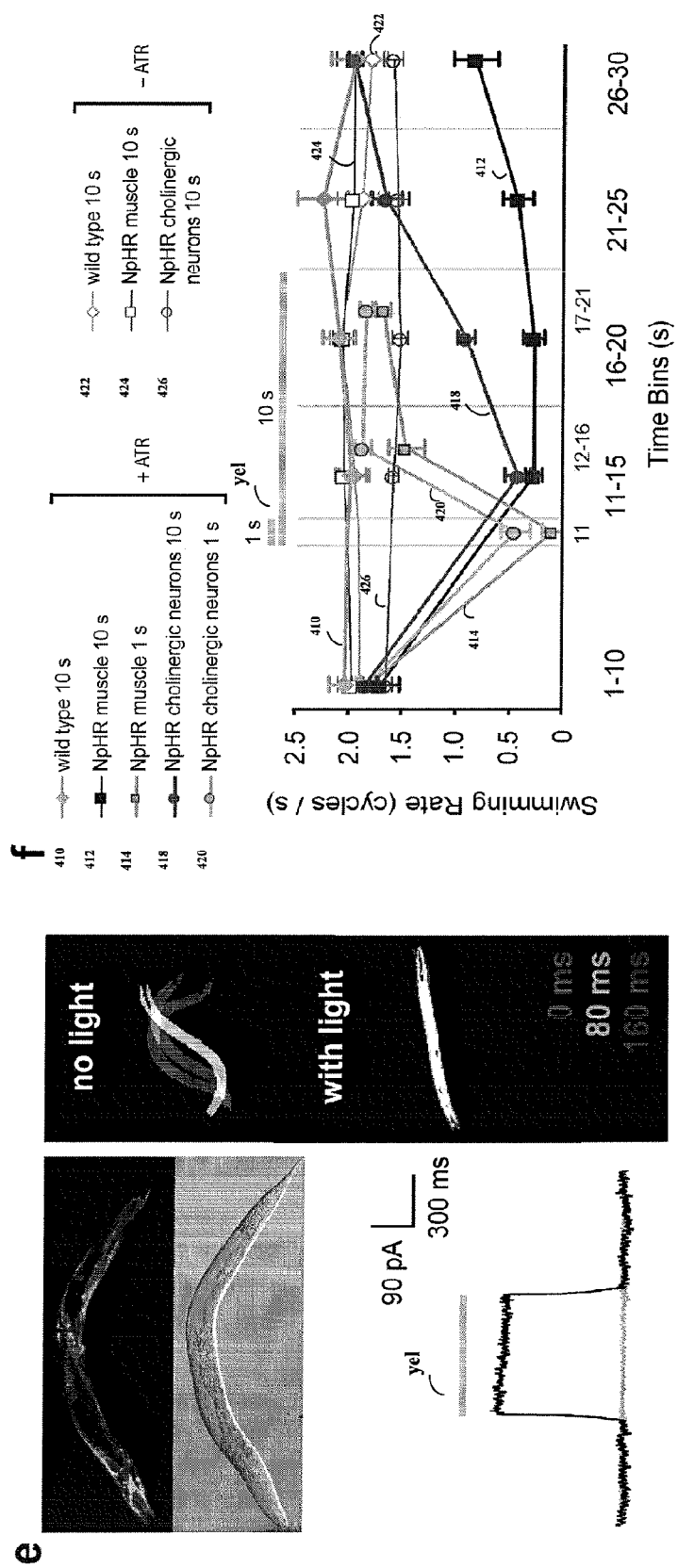
Figure 4:
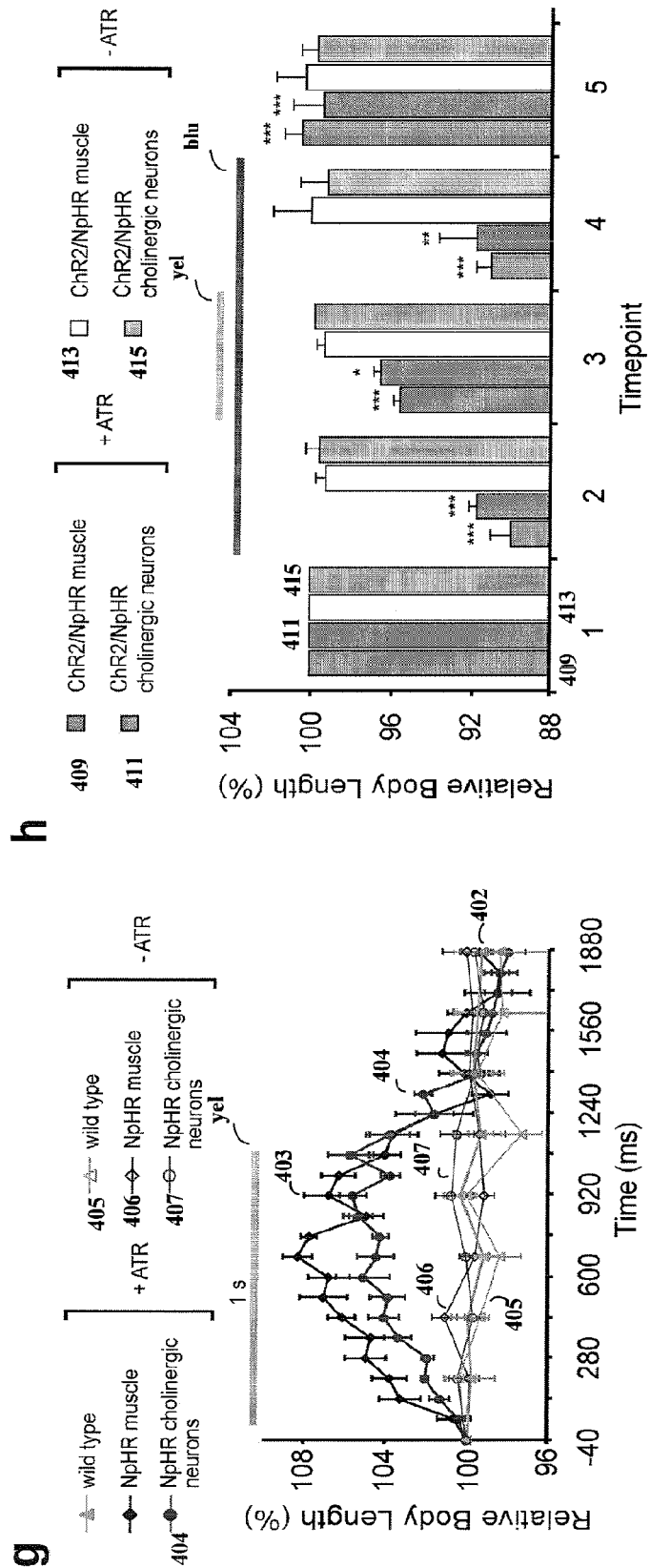

A confocal image was taken from acute mouse brain slice showing membrane-localized NpHR-EYFP expression in the hippocampal CA3 subfield (FIG. 4B left). Current clamp recording showed NpHR-mediated inhibition of specific spikes during a train of action potentials evoked by pulsed current injection (300 pA, 20 Hz, FIG. 4B right).

Epifluorescence images of cortical neurons triple-labeled with NpHR-EYFP, ChR2-mCherry, and Fura-2 showed expression in the neurons. (FIG. 4C)

Simultaneous illumination of cells co-expressing NpHR-EYFP and ChR2-mCherry with steady yellow (continuous illumination, 6 s) and pulsed blue light (50 pulses at 15 ms per flash, 10 Hz) prevented [Ca2+] transients (FIG. 4D). Subsequent photostimulation of the same cells with blue light pulses (50 pulses at 15 ms per flash, 10 Hz) evoked reliable [Ca2+] transients. A bar graph was generated that shows the photostimulation-induced fluorescence changes (FIG. 4D, n=6 ChR2-activated triple-labeled cells).

Epifluorescence images showed Pmyo-3-mediated (transgene zxEx30) NpHR-ECFP expression in the body wall muscles of C. elegans (FIG. 4E). A muscle voltage clamp trace showed photocurrent in transgenic C. elegans expressing NpHR-ECFP (transgene zxEx30) and raised in the presence of ATR. A lack of response in transgenic animal raised in the absence of ATR was noted. Animal postures from three consecutive movie frames (frame rate 12.5 Hz), either with or without NpHR photoactivation, were superimposed to show lack of movement in NpHR photoactivated animals.

The effect of 10 s illumination on swimming rate (n=10 for each set) in wild type controls, animals expressing NpHR in muscles (transgene zxEx29, FIG. 4F blue), or cholinergic motoneurons (transgene zxEx33, FIG. 4F red) was monitored. The number of swimming cycles per second was counted in bins of 5 s intervals. A briefer 1 s illumination protocol was also used, revealing rapid inhibition during illumination and faster recovery by comparison with the 10 s illumination.

The effect of is illumination on body length (n=5-6 for each set) was monitored (FIG. 4G). Movies were taken from transgenic worms expressing NpHR in muscles (transgene zxEx29) or cholinergic motoneurons (transgene zxEx33). Combined ChR2/NpHR expression in muscle cells (transgene zxEx32) or cholinergic motoneurons (transgene zxEx34) of behaving worms. A plot was generated that shows the body length during the first frame before illumination, the 13 frames during the illumination and the next 11 frames after illumination ended (FIGS. 4F, 4G and 4H) including controls and combined ChR2/NpHR expression in muscle cells (transgene zxEc32) or cholinergic motoneurons (transgene zxEx34) of behaving worms.

NpHR activation significantly reversed the muscle contraction caused by ChR2 activation (n=6 per condition; *, $p<0.05$; , $p<0.01$; *, $p<0.001$; between consecutive time points; t-test), but not in animals raised in the absence of ATR.

According to a first experimental method, swimming of a transgenic C. elegans expressing NpHR (transgene zxEx29) in muscles is instantaneously, and repeatedly, inhibited by photoactivation of HR.

According to a second experimental method, swimming of a transgenic C. elegans expressing NpHR in cholinergic motoneurons (transgene zxEx33) is instantaneously inhibited by photoactivation of NpHR.

According to a third experimental method, transgenic C. elegans expressing NpHR-ECFP in muscles (transgene zxEx30). Movement is rapidly inhibited (3×) by photoactivation of HR, and the body relaxes and dilates.

According to a fourth experimental method, one transgenic C. elegans expressing NpHR in muscles (transgene zxEx29), and one non-transgenic control animal. Movement of the transgenic animal is rapidly inhibited by photoactivation of HR.

According to a fifth experimental method, transgenic C. elegans expressing NpHR in cholinergic motoneurons (transgene zxEx33). Movement is rapidly inhibited by photoactivation of HR, and the body relaxes and dilates.

According to a sixth experimental method, co-expression and -activation of ChR2(H134R)-EYFP and NpHR in cholinergic motoneurons of transgenic C. elegans (transgene zxEx34). The animal is illuminated with blue light for ChR2 activation, causing contractions, then, while ChR2 is still photoactivated, NpHR is photoactivated by yellow light, causing significant body relaxation. When NpHR activation ends, the animal contracts again (ChR2 still activated), and finally, when ChR2 activation ends, the animal relaxes to the initial body length.

According to a seventh experimental method, co-expression and rapidly alternating activation of ChR2(H134R) EYFP and NpHR in muscles of transgenic C. elegans (transgene zxEx32). The animal is illuminated with alternating blue light (for ChR2 activation), causing contractions, and yellow light causing significant body relaxation.

Figure 5:
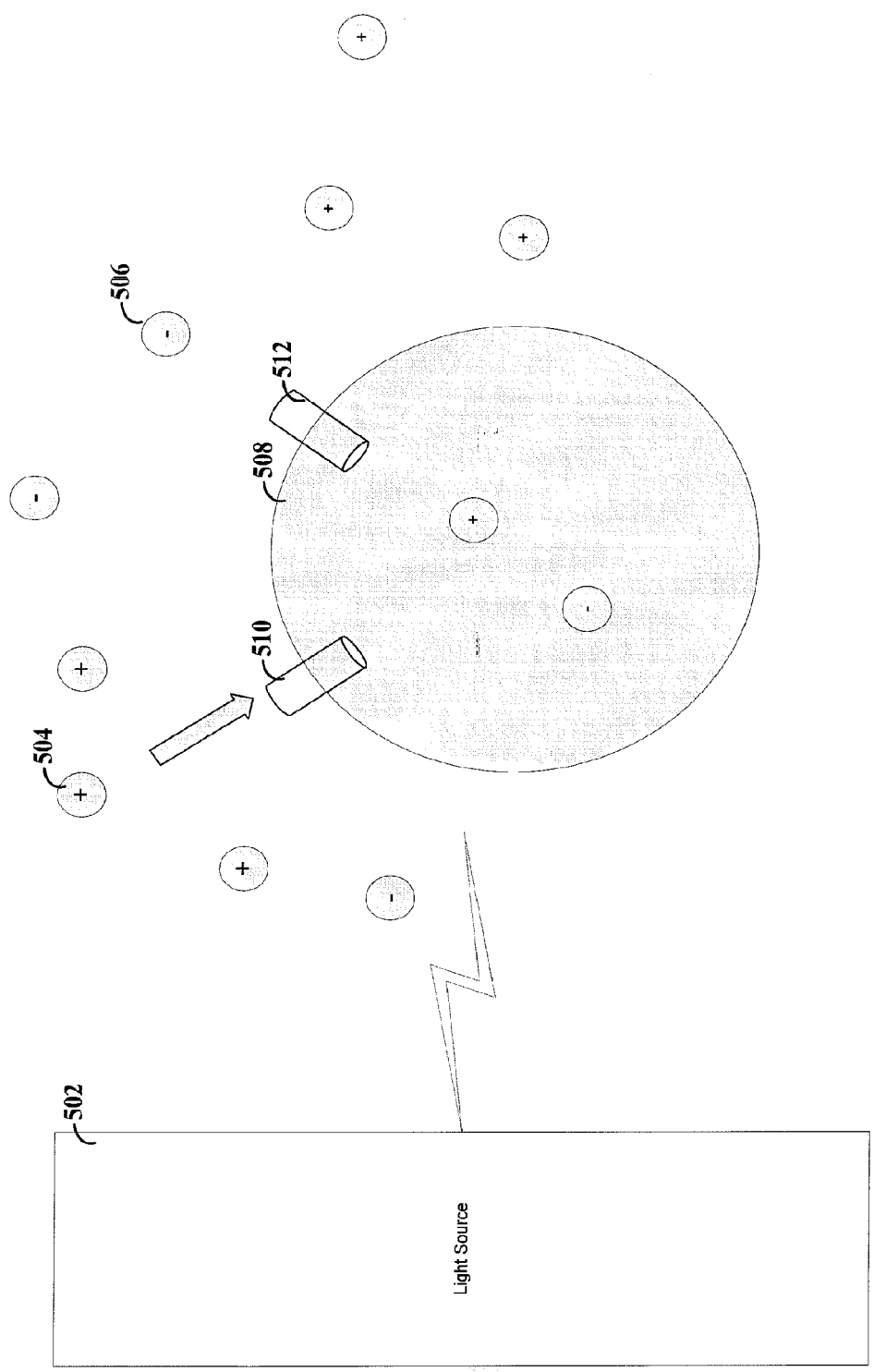
FIG. 5 shows a light source and modified cell, according to an example embodiment of the present invention.

FIG. 5 depicts an arrangement with multiple light sources, according to an example embodiment of the present invention. FIG. 5 shows light sources 502 and 504 that illuminate proteins 510 and 514. The proteins 510 and 514 are engineered within cell 512 to control current across the cell membrane in response to light from light sources 502 and 504, respectively. In one instance, the first protein 510 functions to dissuade action potential firing, while the second protein 514 functions to encourage action potential firing. Each of proteins 510 and 514 are responsive to light. In a particular instance, the first protein is responsive to light from light source 502 having a wavelength A and the second protein is responsive to light from light source 504 having a wavelength B. Thus, the light sources can be used to control each protein independently. This can be useful for both encouraging and dissuading action potentials in the cell. In another instance, having both types of proteins allows for both positive and negative control of the cell membrane voltage. Thus, the different light sources and proteins could be used to control the voltage or current level (e.g., clamping) of the cell membrane.

One method of determining responsiveness involves quantifying the responsiveness in terms of the intensity of light required to produce a given response. In some instances, the first or second protein can still be responsive to the alternate wavelength of light although the responsiveness of the protein may be less than that of the primary wavelength. Accordingly, a protein of a first type may have some responsiveness to the wavelength corresponding to the other type of protein while still maintaining sufficient independence of operation. In one such instance, control of the cell can be implemented by shifting either the wavelength of light or the intensity of the light. For instance, the wavelength can be shifted between A and B to induce a corresponding increase or decrease the membrane voltage potential.

Embodiments of the invention can be implemented with just the protein based ion pump(s). In a specific example, pump 510 is designed to operate using an endogenous cofactor, such as ATR, which can be found in people and many animals. This is particularly useful for minimizing intrusiveness of in vivo applications because it can reduce the need for foreign substances (e.g., cofactors). In a particular instance, pump is a halorhodopsin that acts as an anion pump (e.g., $Cl^-$) that is activated in response to light from light source 502 within milliseconds. Such a fast response allows for the system to control (dissuade) individual action potentials in the cell.

According to one embodiment of the present invention, pump 514 can optionally be implemented for purposes other than dissuading action potential firing, such as controlling the voltage level of cell 508. More specifically, a sensor can be used to provide feedback to the light source 502. For instance, this feedback could be a measurement of the voltage or current across the cell membrane. Thus, the light source could be configured to maintain a constant current or voltage (e.g., clamp) across the cell. Moreover, the amount of responsiveness can be controlled by modifying one or more of the intensity and wavelength of the light.

Figure 6:
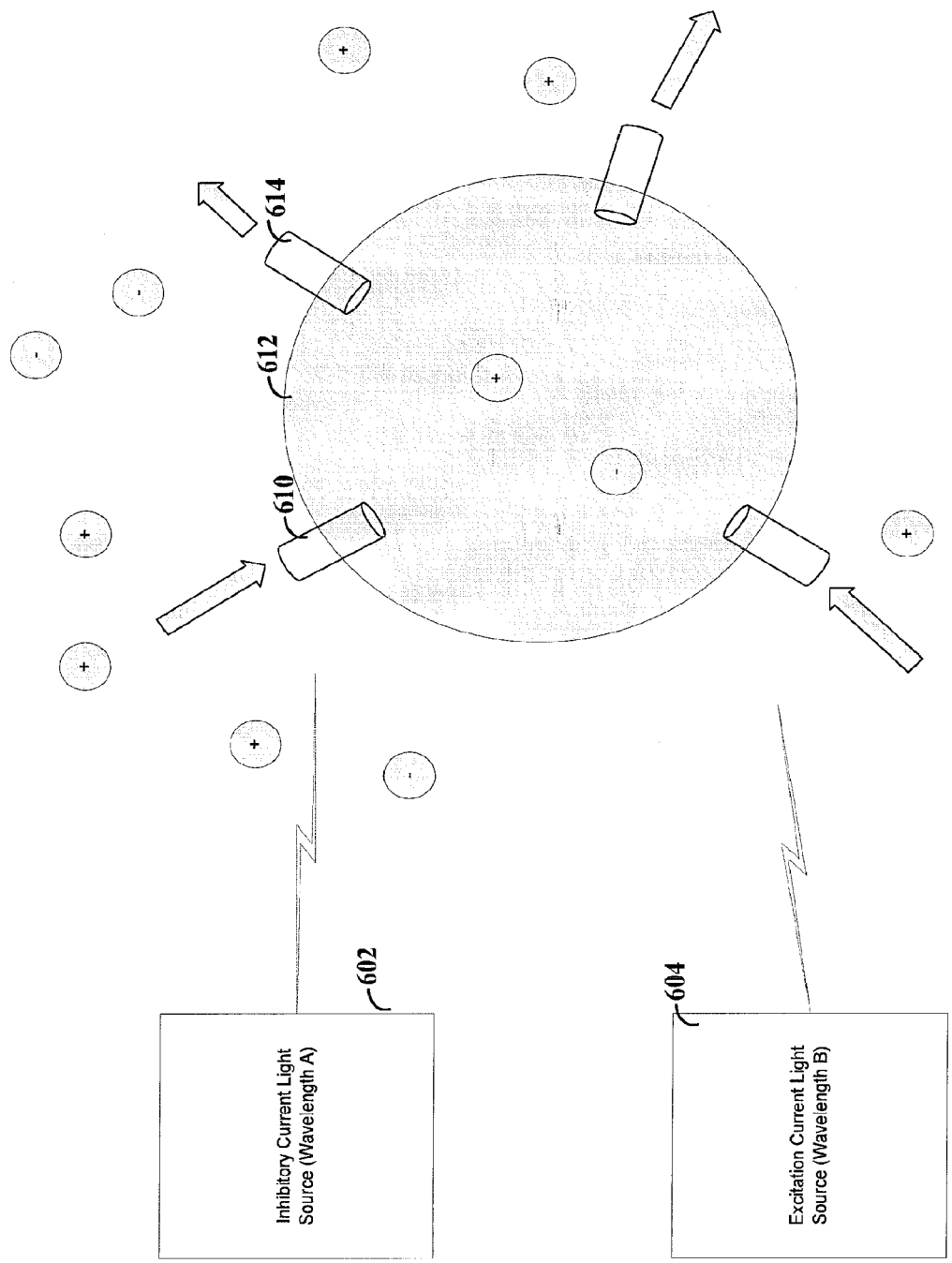
FIG. 6 depicts an arrangement with multiple light sources, according to an example embodiment of the present invention.

FIG. 6 shows a system for controlling electrical properties of one or more cells in vivo, according to an example embodiment of the present invention. Control/Interface unit 602 enables/disables light source 604 to illuminate target cells 608. A delivery mechanism, such as fiber optic cable 606, routes or otherwise directs the light to target cells 608. Fiber optic cable 606 may include a bundle of optical cables, each capable of carrying and directing light independently. Thus, fiber optic cable 606 can be configured to deliver light having one or more wavelengths to multiple locations. Sensor 610 can be implemented, e.g., as an optical device such as an optical scope or as a voltmeter, to provide feedback to control unit 642. In a particular instance, the feedback includes optical imaging of the target cells or of other related cells. In another instance, the feedback could monitor the voltage response of the target cells, including the amount of action potential firing.

Figure 7:
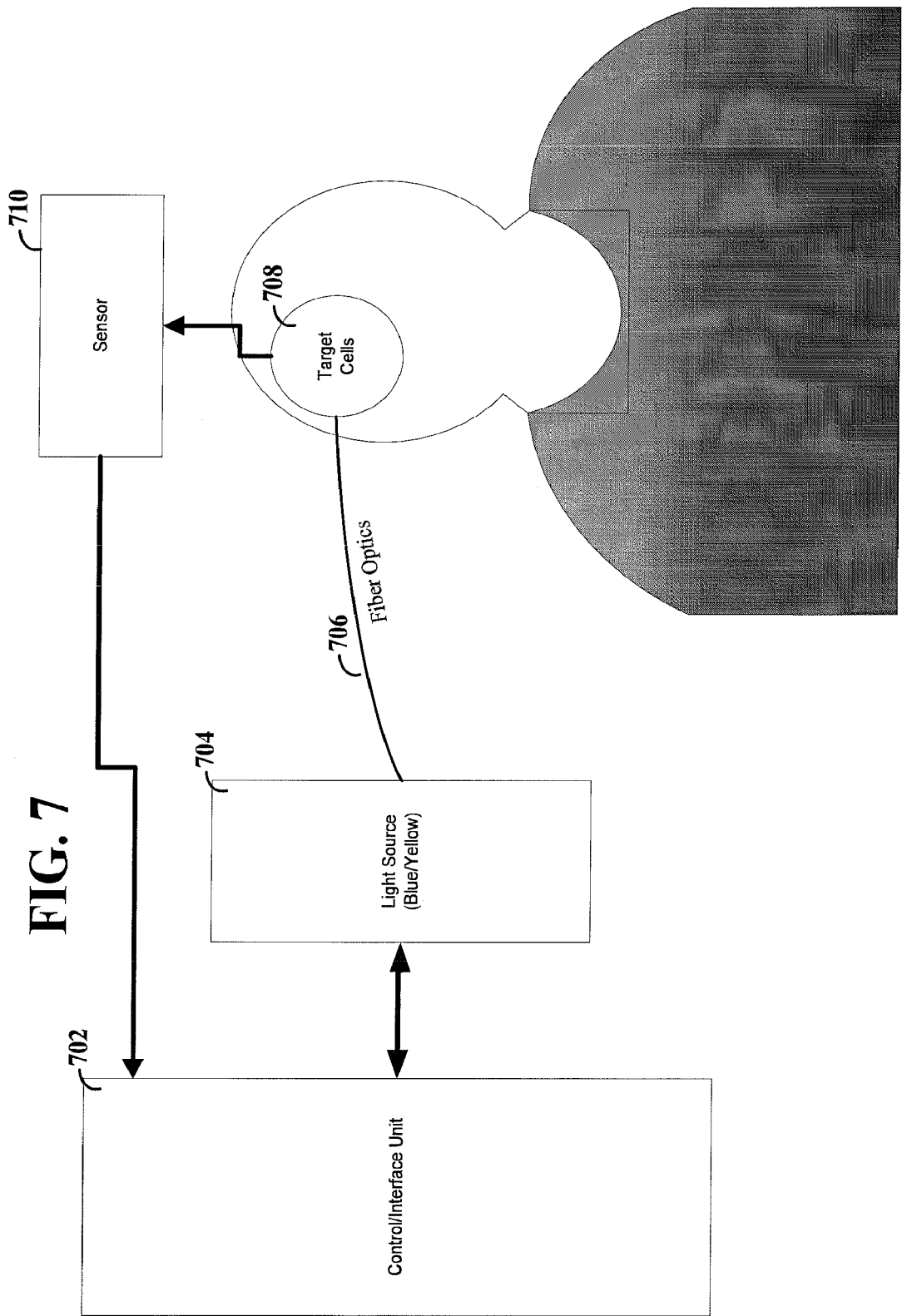
FIG. 7 shows a system for controlling electrical properties of one or more cells in vivo, according to an example embodiment of the present invention.
Figure 8:
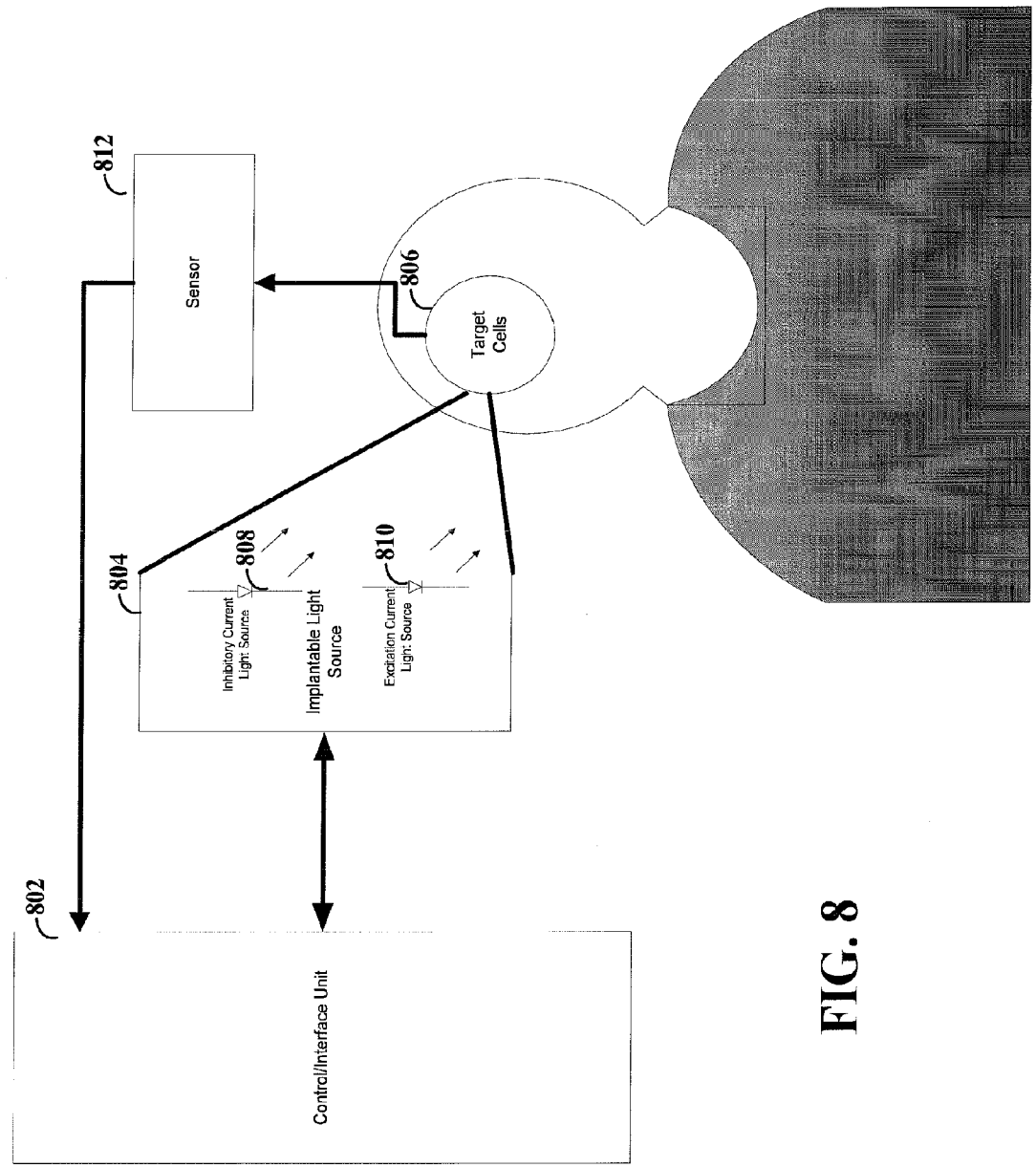
FIG. 8 shows a system for controlling electrical properties of one or more cells in vivo, according to an example embodiment of the present invention.

FIG. 7 shows a system for controlling electrical properties of one or more cells in vivo, according to an example embodiment of the present invention. Control/Interface unit 702 enables/disables implantable light source 704, which in turn illuminates target cells 706. Light source 704 is shown with two light source, inhibitory current light source 708 and excitation current light source 710. Light source 708 produces light at a wavelength and intensity that an inhibitory protein is responsive to, while light source 710 produces light at a wavelength and intensity that an excitation protein is responsive to. One skilled in the art would recognize that various configurations of light source 710 are possible, including a single inhibitory light source or an array of light sources having one or more wavelengths. Control/Interface unit 702 communicates with light source 704 through any suitable communication mechanisms, such as wired communications or wireless communications using radio-frequency signals, magnetic signals and the like. As discussed above in connection with FIG. 6, sensor 712 can optionally be implemented for providing feedback to control unit 702.

Another important aspect of the present invention concerns applications and uses which benefit by reducing toxicity of cells. In certain applications and uses, cells modified to include ion pump molecules can become intolerably toxic. Toxicity can become increasingly problematic as the expression level increases in a cell or the network, for example, when expecting consistent results under repeated tests using the same cell or neural network. A number of embodiments discussed above specifically mention the mammalianized NpHR sequence (GenBank Accession No. EF474018). In connection with the present invention, it has been discovered that this mammalianized NpHR coding sequence has a toxicity that is nearly 100%. It has been discovered that for high expression levels the mammalianized NpHR sequence manifests toxicity at 87% which is considered near enough complete toxicity to be considered as a baseline toxicity reference level which can be substantially reduced using different (NpHR-based but having a different NpHR-based sequence) molecules. Accordingly, various aspects of the present invention are implemented with significantly reduced toxicity.

The toxicity levels were obtained by a stringent process of identifying any cell abnormality, such as blebs on the cell membrane. For the purposes of this disclosure and the data presented herein, a cell with even single abnormality is considered toxic as are any dead cells. A "toxicity level," as used in this disclosure, means the percentage of cells that are considered toxic.

As discussed herein, the expression levels are obtained by increasing the original expression levels discussed above (i.e., about 2×10e7 infectious units (ifu) per milliliter) to one of high expression of at least 3×10e7 ifu per milliliter; very high expression of at least 4×10e7 ifu per milliliter; ultra high expression of at least 5×10e7 ifu per milliliter; or very ultra high expression of at least 1×10e8 ifu per milliliter. In a particular embodiment the expression levels can characterized in terms of their mean photo current being 44 pA or higher.

Various embodiments of the present invention allow for substantially reduced toxicity levels in high expression level (relative to the mammalianized NpHR sequence).

According to one embodiment, an opsin sequence is implemented that exhibits a toxicity of about 72%. A specific example is SPChR2-NpHR (SEQ ID NO 7), where a signal peptide (first 15aa) from ChR2 is added to the N-terminus (SEQ ID NO 11): DYGGALSAVGRELL.

According to one embodiment, an opsin sequence is implemented that exhibits a toxicity of about 69%. A specific example is SPnAChR-L-NpHR (SEQ ID NO 8), where signal peptide (23aa) from nicotinic acetylcholine receptor is added to the N-terminus (SEQ ID NO 12): MGLRALMLWL-LAAAGLVRESLQG.

According to one embodiment, an opsin sequence is implemented that exhibits a toxicity of about 59%. A specific example is NpHR-VSNL (SEQ ID NO 9), where the PDZ binding motif (SEQ ID NO 24) VSNL is added to the C-terminus.

According to one embodiment, an NpHR coding sequence is implemented with a toxicity of about half of the base-line toxicity. A specific example is an NpHR-based sequence that uses the codons originally present in *Natronomonas pharaonis*. Another example is an NpHR-based sequence where a signal peptide (18aa) from nicotinic acetylcholine receptor is added to the N-terminus (SEQ ID NO 13): MRGTPLLLV-VSLFSLLQD.

According to another embodiment, an NpHR coding sequence is implemented with a toxicity of between about 34% and 40%. A specific example is an NpHR-based sequence that is formed by adding the PDZ binding motif (SEQ ID NO 14) ETQZ to the C-terminus (NpHR-ETQV).

According to another embodiment, an NpHR coding sequence is implemented with a toxicity of between about 20% and 26%. A specific example is an NpHR-based sequence that is formed by adding the (SEQ ID NO 15) PTPP sequence to the C-terminus to promote interaction with actin-binding protein filamin (NpHR-actin).

According to another embodiment, an NpHR coding sequence is implemented with a toxicity of between about 4% and 10%. A specific example is an NpHR-based sequence that is formed by adding the ER export signal to the C-terminus: (SEQ ID NO 16) VLGSL or, more generally, (SEQ ID NO 17) VXXSL (NpHR-ERexport).

According to another embodiment, an NpHR coding sequence is implemented with a peak current of between about 11.1 pA and 50 pA. A specific example is an NpHR-based sequence that uses the codons originally present in *Natronomonas pharaonis*.

According to another embodiment, an NpHR coding sequence is implemented with a peak current of between about 40 pA and 61 pA. A specific example is an NpHR-based sequence where a signal peptide (18aa) from nicotinic acetylcholine receptor is added to the N-terminus: (SEQ ID NO 13) MRGTPLLLVVSLFSLLQD.

According to another embodiment, an NpHR coding sequence is implemented with a peak current of between about 49 pA and 77 pA. A specific example is an NpHR-based sequence that is formed by adding the PDZ binding motif (SEQ ID NO 14) ETQZ to the C-terminus (NpHR-ETQV).

According to another embodiment, an NpHR coding sequence is implemented with a peak current of between about 11 pA and 70 pA. A specific example is an NpHR-based sequence that is formed by adding the (SEQ ID NO 15) PTPP sequence to the C-terminus to promote interaction with actin-binding protein filamin (NpHR-actin). Another example is an NpHR-based sequence that is formed by adding the ER export signal to the C-terminus: VLGSL or, more generally, (SEQ ID NO 17) VXXSL (NpHR-ERexport).

Experimental data results showing toxicity and peak current for various NpHR sequences are shown in Table 2.

large round intracellular blobs either in the soma or dendrites were counted as toxic cells. The photocurrents for each of the constructs were assessed by electrophysiology as described herein and also similar to that taught by "Multimodal fast optical interrogation of neural circuitry" by Zhang, et al, Nature (Apr. 5, 2007) Vol. 446: 633-639, which is fully incorporated herein by reference. It should be noted that while the neurons were allowed to express protein for at least one week, this time frame was about half of the time allotted in various underlying experimental tests discussed above. Additional expression time would allow for more expression, which in turn would result in increased toxicity and photo-currents. Accordingly, assuming a near-linear increase in toxicity, the embodiments showing around 37% toxicity would reach about 74%.

Various embodiments are directed toward a construct that includes ER export signals, including, but not limited to: (SEQ ID NO 17) VXXSL; (SEQ ID NO 18) FXYENE (see "A sequence motif responsible for ER export and surface expression of Kir2.0 inward rectifier K(+) channels" Stockklausner et al., FEBS Lett.; 493 (2-3):129-133 March, 2001; and "Role of ER Export Signals in Controlling Surface Potassium Channel Numbers" Ma et al., Science Vol. 291. no. 5502:316-319, 2001); C-terminal valine residue (see "A Specific Endoplasmic Reticulum Export Signal Drives Transport of Stem Cell Factor (Kitl) to the Cell Surface" Paulhe et al., J. Biol. Chem., Vol. 279, Issue 53, 55545-55555, Dec. 31, 2004); VMI (see "Signal-dependent export of GABA transporter 1 from the ER-Golgi intermediate compartment is specified by a C-terminal motif" Farhan et al., J. Cell Sci. 121:753-761, Feb. 19,

TABLE 2

| Construct | Molecular Modification | Toxicity in neurons | Peak photocurrent (mean ± s.d) |
|---|---|---|---|
| Humanized NpHR (SEQ ID NO 1) | none | 87% | 48.0 ± 7.0 pA |
| Non-Humanized NpHR (SEQ ID NO 2) | use the original codons from bacteria | 37% | 29.6 ± 18.5 pA |
| $SP_{nAChR-S}$-NpHR (SEQ ID NO 3) | Added signal peptide (18 aa) from nicotinic acetylcholine receptor to the N-terminus: MRGTPLLLVVSLFSLLQD | 37% | 51.5 ± 9.2 pA |
| NpHR-ETQV (SEQ ID NO 4) | Added the PDZ binding motif ETQV to the C-terminus | 34% | 63.7 ± 12.7 pA |
| NpHR-actin (SEQ ID NO 5) | Added the PTPP sequence to the C-terminus to promote interaction with actin-binding protein filamin | 23% | 39.8 ± 20.2 pA |
| NpHR-ERexport (SEQ ID NO 6) | Added the ER export signal to the C-terminus: VLGSL (more general VXXSL) | 7% | 40.3 ± 28.5 pA |

Toxicity was assessed in cultured hippocampal neurons as follows: neurons 4 days in vitro were infected with lentivirus for each of the constructs and allowed to accumulate protein for two weeks before assessing toxicity. Cells that displayed 2008.) Each of the above-mentioned references is incorporated herein by reference in their entirety.

Various embodiments are directed toward a construct that includes signal peptides for insertion into plasma membrane including, but not limited to, signal peptides from other opsins or from other transmembrane proteins such as the nicotinic acetylcholine receptor (Isenberg et al., 1989, J. Neurochemistry).

For additional information regarding implementation of a signal peptide (first 15aa) from ChR2 added to the N-terminus reference can be made to "Millisecond-timescale, genetically-targeted optical control of neural activity" Boyden, et al., Nature Neuroscience 8(9):1263-1268 (2005), which is fully incorporated herein by reference.

For additional information regarding implementation of a signal peptide (23aa) from nicotinic acetylcholine receptor added to the N-terminus reference can be made to Bocquet et al., "A prokaryotic proton-gated ion channel from the nicotinic acetylcholine receptor family" Nature 445:116-119, January, 2007.

Various embodiments are directed toward a construct that includes PDZ binding motifs including, but not limited to, (SEQ ID NOS 19-20) X(S/T)XV (SEQ ID NO 21) ETQV) or (SEQ ID NOS 22-23) X(S/T)XL (e.g., VSNL).

For additional information regarding implementation of NpHR-VSNL, where the PDZ binding motif VSNL is added to the C-terminus, reference can be made to "Interactions with PDZ proteins are required for L-type calcium channels to activate cAMP response element-binding protein-dependent gene expression" Weick et al., J. Neurosci. 23:3446-3456, 2003, which is fully incorporated herein by reference.

For additional information regarding implementation of NpHR-ETQV-based sequences, reference can be made to "Targeting and Readout Strategies for Fast Optical Neural Control In Vitro and In Vivo" Gradinaru, et al., The Journal of Neuroscience 27(52):14231-14238, Dec. 26, 2007, which is fully incorporated herein by reference.

For additional information regarding implementation of original codon-based sequences, reference can be made to "Light Driven Proton Pump or Chloride Pump by Halorhodopsin" Bamberg, et al., Proc. Natl. Acad. Sci. USA Vol. 90: 639-643, January 1993 Biophysics, which is fully incorporated herein by reference.

For additional information regarding implementation of $SP_{nAchR-S}$-pHR-based sequences, reference can be made to "Rapid Communication Cloning of a Putative Neuronal Nicotinic Acetylcholine Receptor Subunit" Isenberg, et al., J. Neurochem. 52(3):988-991, 1989, which is fully incorporated herein by reference.

For additional information regarding implementation of NpHR-actin-based sequences, reference can be made to "Localization and Enhanced Current Density of the Kv4.2 Potassium Channel by Interaction with the Actin-binding Protein Filamin" Petrecca, et al., The Journal of Neuroscience 20(23):8763-8744, December, 2000, which is fully incorporated herein by reference.

For additional information regarding implementation of ERexport-based sequences, reference can be made to "Surface Expression of Kv1 Voltage-Gated K+Channels is Governed by a C-terminal Motif" Levitan, et al., TCM 10(7):317-320, 2000, which is fully incorporated herein by reference.

The various sequences need not be implemented in isolation. To the contrary, embodiments of the present invention involve various combinations of the above sequences with one another on the same gene. For example, the desired expression levels, peak currents and toxicity levels are tailored through a combination of two or more different sequences within the target cellular structure(s). Specific embodiments involve the selection and use of specific sequences that bind to different portions of the gene (e.g., the C-terminus and the N-terminus). Such selections results in characteristics (e.g., toxicity, current levels and expression levels) not present in embodiments that use only a single sequence. Thus, various embodiments are directed toward combinations of two or more of the above listed modifications. For example, a hybrid construct of $SP_{nAChR-S}$-NpHR-ERexport (SEQ ID NO 10). Another example involves the addition of ChR2 to the cell.

Thus, various embodiments can be implemented in which two or more constructs are used to express an NpHR-based protein in the cell. Each construct is capable of independently expressing the protein. In one instance, the constructs can be implemented in the same sequence. In another instance, the constructs can be sequentially delivered using two or more different sequences.

Additional constructs can be implemented by co-expressing helper proteins, such as chaperones, that could be useful in aiding NpHR folding and trafficking.

A few example sequence listings are provided in the Appendix, which forms part of this specification. It should be noted that all the sequences contain the EYFP fluorescent protein for visualization purposes. Embodiments of the present invention can be implemented without this EYFP fluorescent protein. For example, each of the sequences can be implemented either on the NpHR alone (with no fluorescent protein) or on the NpHR-X fluorescent protein complex.

Many human applications of the present invention require governmental approval prior to their use. For instance, human use of gene therapy may require such approval. However, similar gene therapies in neurons (nonproliferative cells that are non-susceptible to neoplasms) are proceeding rapidly, with active, FDA-approved clinical trials already underway involving viral gene delivery to human brains. This is likely to facilitate the use of various embodiments of the present invention for a large variety of applications. The following is a non-exhaustive list of a few examples of such applications and embodiments.

Addiction is associated with a variety of brain functions, including reward and expectation. Additionally, the driving cause of addiction may vary between individuals. According to one embodiment, addiction, for example nicotine addiction, may be treated with optogenetic stabilization of small areas on the insula. Optionally, functional brain imaging—for example cued-state PET or fMRI—may be used to locate a hypermetabolic focus in order to determine a precise target spot for the intervention on the insula surface.

Optogenetic excitation of the nucleus accumbens and septum may provide reward and pleasure to a patient without need for resorting to use of substances, and hence may hold a key to addiction treatment. Conversely, optogenetic stabilization of the nucleus accumbens and septum may be used to decrease drug craving in the context of addiction. In an alternative embodiment, optogenetic stabilization of hypermetabolic activity observed at the genu of the anterior cingulate (BA32) can be used to decrease drug craving. Optogenetic stabilization of cells within the arcuate nucleus of the medial hypothalamus which contain peptide products of pro-opiomelanocortin (POMC) and cocaine-and-amphetamine-regulating transcript (CART) can also be used to decrease drug addiction behavior. For further information in this regard, reference may be made to: Naqvi N H, Rudrauf D, Damasio H, Bechara A. "Damage to the insula disrupts addiction to cigarette smoking." Science. 2007 Jan. 26; 315(5811): 531-534, which is fully incorporated herein by reference.

Optogenetic stimulation of neuroendocrine neurons of the hypothalamic periventricular nucleus that secrete somatostatin can be used to inhibit secretion of growth hormone from the anterior pituitary, for example in acromegaly. Optogenetic stabilization of neuroendocrine neurons that secrete somatostatin or growth hormone can be used to increase growth and physical development. Among the changes that accompany "normal" aging, is a sharp decline in serum growth hormone levels after the $4^{th}$ and $5^{th}$ decades. Consequently, physical deterioration associated with aging may be lessened through optogenetic stabilization of the periventricular nucleus.

Optogenetic stabilization of the ventromedial nucleus of the hypothalamus, particularly the pro-opiomelanocortin (POMC) and cocaine-and-amphetamine-regulating transcript (CART) of the arcuate nucleus, can be used to increase appetite, and thereby treat anorexia nervosa. Alternatively, optogenetic stimulation of the lateral nuclei of the hypothalamus can be used to increase appetite and eating behaviors.

Optogenetic excitation in the cholinergic cells of affected areas including the temporal lobe, the NBM (Nucleus basalis of Meynert) and the posterior cingulate gyrus (BA 31) provides stimulation, and hence neurotrophic drive to deteriorating areas. Because the affected areas are widespread within the brain, an analogous treatment with implanted electrodes may be less feasible than an opto-genetic approach.

Anxiety disorders are typically associated with increased activity in the left temporal and frontal cortex and amygdala, which trends toward normal as anxiety resolves. Accordingly, the affected left temporal and frontal regions and amygdala may be treated with optogenetic stabilization, so as to dampen activity in these regions.

In normal physiology, photosensitive neural cells of the retina, which depolarize in response to the light that they receive, create a visual map of the received light pattern. Optogenetic ion channels can be used to mimic this process in many parts of the body, and the eyes are no exception. In the case of visual impairment or blindness due to damaged retina, a functionally new retina can be grown, which uses natural ambient light rather than flashing light patterns from an implanted device. The artificial retina grown may be placed in the location of the original retina (where it can take advantage of the optic nerve serving as a conduit back to the visual cortex). Alternatively, the artificial retina may be placed in another location, such as the forehead, provided that a conduit for the depolarization signals are transmitted to cortical tissue capable of deciphering the encoded information from the optogenetic sensor matrix. Cortical blindness could also be treated by simulating visual pathways downstream of the visual cortex. The stimulation would be based on visual data produced up stream of the visual cortex or by an artificial light sensor.

Treatment of tachycardia may be accomplished with optogenetic stimulation to parasympathetic nervous system fibers including CN X or Vagus Nerve. This causes a decrease in the SA node rate, thereby decreasing the heart rate and force of contraction. Similarly, optogenetic stabilization of sympathetic nervous system fibers within spinal nerves T1 through T4, serves to slow the heart. For the treatment of pathological bradycardia, optogenetic stabilization of the Vagus nerve, or optogenetic stimulation of sympathetic fibers in T1 through T4 will serve to increase heart rate. Cardiac disrhythmias resulting from aberrant electrical foci that outpace the sinoatrial node may be suppressed by treating the aberrant electrical focus with moderate optogenetic stabilization. This decreases the intrinsic rate of firing within the treated tissue, and permits the sinoatrial node to regain its role in pacing the heart's electrical system. In a similar way, any type of cardiac arrhythmia could be treated. Degeneration of cardiac tissue that occurs in cardiomyopathy or congestive heart failure could also be treated using this invention; the remaining tissue could be excited using various embodiments of the invention.

Optogenetic excitation stimulation of brain regions including the frontal lobe, parietal lobes and hippocampi, may increase processing speed, improve memory, and stimulate growth and interconnection of neurons, including spurring development of neural progenitor cells. As an example, one such application of the present invention is directed to optogenetic excitation stimulation of targeted neurons in the thalamus for the purpose of bringing a patient out of a near-vegetative (barely-conscious) state. Growth of light-gated ion channels or pumps in the membrane of targeted thalamus neurons is effected. These modified neurons are then stimulated, e.g., via optics which may also gain access by the same passageway, by directing a flash of light thereupon so as to modulate the function of the targeted neurons and/or surrounding cells. For further information regarding appropriate modulation techniques (via electrode-based treatment) or further information regarding the associated brain regions for such patients, reference may be made to: Schiff N D, Giacino J T, Kalmar K, Victor J D, Baker K, Gerber M, Fritz B, Eisenberg B, O'Connor J O, Kobylarz E J, Farris S, Machado A, McCagg C, Plum F, Fins J J, Rezai A R. Behavioral improvements with thalamic stimulation after severe traumatic brain injury. Nature. Vol 448. Aug. 2, 2007 pp 600-604.

In an alternative embodiment, optogenetic excitation may be used to treat weakened cardiac muscle in conditions such as congestive heart failure. Electrical assistance to failing heart muscle of CHF is generally not practical, due to the thin-stretched, fragile state of the cardiac wall, and the difficulty in providing an evenly distributed electrical coupling between an electrodes and muscle. For this reason, preferred methods to date for increasing cardiac contractility have involved either pharmacological methods such as Beta agonists, and mechanical approaches such as ventricular assist devices. In this embodiment of the present invention, optogenetic excitation is delivered to weakened heart muscle via light emitting elements on the inner surface of a jacket surround the heart or otherwise against the affected heart wall. Light may be diffused by means well known in the art, to smoothly cover large areas of muscle, prompting contraction with each light pulse.

Optogenetic stabilization in the subgenual portion of the cingulate gyrus (Cg25), yellow light may be applied with an implanted device. The goal would be to treat depression by suppressing target activity in manner analogous to what is taught by Mayberg H S et al., Deep Brain Stimulation for Treatment-Resistant Depression. Neuron, Vol. 45, 651-660, Mar. 3, 2005, 651-660, which is fully incorporated herein by reference. In an alternative embodiment, an optogenetic excitation stimulation method is to increase activity in that region in a manner analogous to what is taught by Schlaepfer et al., Deep Brain stimulation to Reward Circuitry Alleviates Anhedonia in Refractory Major Depression, Neuropsychopharmacology 2007 1-10, which is fully incorporated herein by reference. In yet another embodiment the left dorsolateral prefrontal cortex (LDPFC) is targeted with an optogenetic excitation stimulation method. Pacing the LDLPFC at 5-20 Hz serves to increase the basal metabolic level of this structure which, via connecting circuitry, serves to decrease activity in Cg 25, improving depression in the process. Suppression of the right dorsolateral prefrontal cortex (RDLPFC) is also an effective depression treatment strategy. This may be accomplished by optogenetic stabilization on the RDLPFC, or suppression may also be accomplished by using optogenetic excitation stimulation, and pulsing at a slow rate-1 Hz or less, improving depression in the process. Vagus nerve stimulation (VNS) may be improved using an optogenetic approach. Use of optogenetic excitation may be used in order to stimulate only the vagus afferents to the brain, such as the nodose ganglion and the jugular ganglion. Efferents from the brain would not receive stimulation by this approach, thus eliminating some of the side-effects of VNS including discomfort in the throat, a cough, difficulty swallowing and a hoarse voice. In an alternative embodiment, the hippocampus may be optogenetically excited, leading to increased dendritic and axonal sprouting, and overall growth of the hippocampus. Other brain regions implicated in depression that could be treated using this invention include the amygdala, accumbens, orbitofrontal and orbitomedial cortex, hippocampus, olfactory cortex, and dopaminergic, serotonergic, and noradrenergic projections. Optogenetic approaches could be used to control spread of activity through structures like the hippocampus to control depressive symptoms.

So long as there are viable alpha and beta cell populations in the pancreatic islets of Langerhans, the islets can be targeted for the treatment of diabetes. For example, when serum glucose is high (as determined manually or by closed loop glucose detection system), optogenetic excitation may be used to cause insulin release from the beta cells of the islets of Langerhans in the pancreas, while optogenetic stabilization is used to prevent glucagon release from the alpha cells of the islets of Langerhans in the pancreas. Conversely, when blood sugars are too low (as determined manually or by closed loop glucose detection system), optogenetic stabilization may be used to stop beta cell secretion of insulin, and optogenetic excitation may be used to increase alpha-cell secretion of glucagon.

For treatment of epilepsy, quenching or blocking epileptogenic activity is amenable to optogenetic approaches. Most epilepsy patients have a stereotyped pattern of activity spread resulting from an epileptogenic focus Optogenetic stabilization could be used to suppress the abnormal activity before it spreads or truncated it early in its course. Alternatively, activation of excitatory tissue via optogenetic excitation stimulation could be delivered in a series of deliberately asynchronous patterns to disrupt the emerging seizure activity. Another alternative involves the activation of optogenetic excitation stimulation in GABAergic neurons to provide a similar result. Thalamic relays may be targeted with optogenetic stabilization triggered when an abnormal EEG pattern is detected.

Another embodiment involves the treatment of gastrointestinal disorders. The digestive system has its own, semi-autonomous nervous system containing sensory neurons, motor neurons and interneurons. These neurons control movement of the GI tract, as well as trigger specific cells in the gut to release acid, digestive enzymes, and hormones including gastrin, cholecystokinin and secretin. Syndromes that include inadequate secretion of any of these cellular products may be treated with optogenetic stimulation of the producing cell types, or neurons that prompt their activity. Conversely, optogenetic stabilization may be used to treat syndromes in which excessive endocrine and exocrine products are being created. Disorders of lowered intestinal motility, ranging from constipation (particularly in patients with spinal cord injury) to megacolan may be treated with optogenetic excitation of motor neurons in the intestines. Disorders of intestinal hypermotility, including some forms of irritable bowel syndrome may be treated with optogenetic stabilization of neurons that control motility. Neurogentic gastric outlet obstructions may be treated with optogenetic stabilization of neurons and musculature in the pyloris. An alternative approach to hypomobility syndromes would be to provide optogenetic excitation to stretch-sensitive neurons in the walls of the gut, increasing the signal that the gut is full and in need of emptying.

In this same paradigm, an approach to hypermobility syndromes of the gut would be to provide optogenetic stabilization to stretch receptor neurons in the lower GI, thus providing a "false cue" that the gut was empty, and not in need of emptying. In the case of frank fecal incontinence, gaining improved control of the internal and external sphincters may be preferred to slowing the motility of the entire tract. During periods of time during which a patient needs to hold feces in, optogenetic excitation of the internal anal sphincter will provide for retention. Providing optogenetic stimulation to the external sphincter may be used to provide additional continence. When the patient is required to defecate, the internal anal sphincter, and then external anal sphincter should be relaxed, either by pausing the optogenetic stimulation, or by adding optogenetic stabilization.

Conductive hearing loss may be treated by the use of optical cochlear implants. Once the cochlea has been prepared for optogenetic stimulation, a cochlear implant that flashes light may be used. Sensorineural hearing loss may be treated through optical stimulation of downstream targets in the auditory pathway.

Another embodiment of the present invention is directed toward the treatment of blood pressure disorders, such as hypertension. Baroreceptors and chemoreceptors in regions such as the aorta (aortic bodies and paraaortic bodies) and the carotid arteries ("carotid bodies") participate the regulation of blood pressure and respiration by sending afferents via the vagus nerve (CN X), and other pathways to the medulla and pons, particularly the solitary tract and nucleus. Optogenetic excitation of the carotid bodies, aortic bodies, paraortic bodies, may be used to send a false message of "hypertension" to the solitary nucleus and tract, causing it to report that blood pressure should be decreased. Optogenetic excitation or stabilization directly to appropriate parts of the brainstem may also be used to lower blood pressure. The opposite modality causes the optogenetic approach to serve as a pressor, raising blood pressure. A similar effect may also be achieved via optogenetic excitation of the Vagus nerve, or by optogenetic stabilization of sympathetic fibers within spinal nerves T1-T4. In an alternative embodiment, hypertension may be treated with optogenetic stabilization of the heart, resulting in decreased cardiac output and lowered blood pressure. According to another embodiment, optogentic stabilization of aldosterone-producing cells within the adrenal cortex may be used to decrease blood pressure. In yet another alternative embodiment, hypertension may be treated by optogenetic stabilization of vascular smooth muscle. Activating light may be passed transcutaneously to the peripheral vascular bed.

Another example embodiment is directed toward the treatment of hypothalamic-pituitary-adrenal axis disorders. In the treatment of hypothyroidism, optogenetic excitation of parvocellular neuroendocrine, neurons in the paraventricular and anterior hypothalamic nuclei can be used to increase secretion of thyrotropin-releasing hormone (TRH). TRH, in turn, stimulates anterior pituitary to secrete TSH. Conversely, hyperthyroidism may be treated with optogenetic stabilization of the provocellular neuroendocrine neurons. For the treatment of adrenal insufficiency, or of Addison's disease, optogenetic excitation of parvocellular neuroendocrine neurons in the supraoptic nucleus and paraventricular nuclei may be used to increase the secretion of vasopressin, which, with the help of corticotropin-releasing hormone (CRH), stimulate anterior pituitary to secrete ACTH. Cushing syndrome, frequently caused by excessive ACTH secretion, may be treated with optogenetic stabilization of the parvocellular neuroendocrine neurons of supraoptic nuecleus via the same physiological chain of effects described above. Neuroendocrine neurons of the arcuate nucleus produce dopamine, which inhibits secretion of prolactin from the anterior pituitary. Hyperprolactinemia can therefore be treated via optogenetic excitation, while hypoprolactinemia can be treated with optogenetic stabilization of the neuroendocrine cells of the arcuate nucleus.

In the treatment of hyperautonomic states, for example anxiety disorders, optogenetic stabilization of the adrenal medulla may be used to reduce norepinephrine output. Similarly, optogenetic stimulation of the adrenal medulla may be used in persons with need for adrenaline surges, for example those with severe athsma, or disorders that manifest as chronic sleepiness.

Optogenetic stimulation of the adrenal cortex will cause release of chemicals including cortisol, testosterone, and aldosterone. Unlike the adrenal medualla, the adrenal cortex receives its instructions from neuroendocrine hormones secreted from the pituitary and hypothalamus, the lungs, and the kidneys. Regardless, the adrenal cortex is amenable to optogenetic stimulation. Optogenetic stimulation of the cortisol-producing cells of the adrenal cortex may be used to treat Addison's disease. Optogenetic stabilization of cortisol-producing cells of the adrenal cortex may be used to treat Cushing's disease. Optogenetic stimulation of testosterone-producing cells may be used to treat disorders of sexual interest in women: Optogenetic stabilization of those same cells may be used to decrease facial hair in women. Optogenetic stabilization of aldosterone-producing cells within the adrenal cortex may be used to decrease blood pressure. Optogenetic excitation of aldosterone-producing cells within the adrenal cortex may be used to increase blood pressure.

Ontogenetic excitation stimulation of specific affected brain regions may be used to increase processing speed, and stimulate growth and interconnection of neurons, including spurring the maturation of neural progenitor cells. Such uses can be particularly useful for treatment of mental retardation.

According to another embodiment of the present invention, various muscle diseases and injuries can be treated. Palsies related to muscle damage, peripheral nerve damage and to dystrophic diseases can be treated with optogenetic excitation to cause contraction, and optogenetic stabilization to cause relaxation. This latter relaxation via optogenetic stabilization approach can also be used to prevent muscle wasting, maintain tone, and permit coordinated movement as opposing muscle groups are contracted. Likewise, frank spasticity can be treated via optogenetic stabilization.

In areas as diverse as peripheral nerve truncation, stroke, traumatic brain injury and spinal cord injury, there is a need to foster the growth of new neurons, and assist with their integration into a functional network with other neurons and with their target tissue. Re-growth of new neuronal tracts may be encouraged via optogenetic excitation, which serves to signal stem cells to sprout axons and dendrites, and to integrate themselves with the network. Use of an optogenetic technique (as opposed to electrodes) prevents receipt of signals by intact tissue, and serves to ensure that new target tissue grows by virtue of a communication set up with the developing neurons, and not with an artificial signal like current emanating from an electrode.

Obesity can be treated with optogenetic excitation to the ventromedial nucleus of the hypothalamus, particularly the pro-opiomelanocortin (POMC) and cocaine-and-amphetamine-regulating transcript (CART) of the arcuate nucleus. In an alternative embodiment, obesity can be treated via optogenetic stabilization of the lateral nuclei of the hypothalamus.

In another embodiment, optogenetic stimulation to leptin-producing cells, or to cells with leptin receptors within the hypothalamus may be used to decrease appetite and hence treat obesity.

Destructive lesions to the anterior capsule, and analogous DBS to that region are established means of treating severe, intractable obsessive-compulsive disorder 48 (OCD48). Such approaches may be emulated using optogenetic stabilization to the anterior limb of the internal capsule, or to regions such as BA32 and Cg24 which show metabolic decrease as OCD remits.

Chronic Pain can be treated using another embodiment of the present invention. Electrical stimulation methods include local peripheral nerve stimulation, local cranial nerve stimulation and "subthreshold" motor cortex stimulation. Reasonable optogentic approaches include optogenetic stabilization at local painful sites. Attention to promoter selection would ensure that other sensory and motor fibers would be unaffected. Selective optogenetic excitation of interneurons at the primary motor cortex also may provide effective pain relief. Also, optogenetic stabilization at the sensory thalamus, (particularly medial thalamic nuclei), periventricular grey matter, and ventral raphe nuclei, may be used to produce pain relief. In an alternative embodiment, optogenetic stabilization of parvalbumin-expressing cells targeting as targeting strategy, may be used to treat pain by decreasing Substance P production. The release of endogenous opiods may be accomplished by using optogenetic excitation to increase activity in the nucleus accumbens. In an alternative embodiment, when POMC neurons of the arcuate nucleus of the medial hypothalamus are optogenetically excited, beta endorphin are increased, providing viable treatment approaches for depression and for chronic pain.

Parkinson's Disease can be treated by expressing optogenetic stabilization in the glutamatergic neurons in either the subthalamic nucleus (STN) or the globus pallidus interna (GPi) using an excitatory-specific promoter such as CaMKIIα, and apply optogenetic stabilization. Unlike electrical modulation in which all cell-types are affected, only glutamatergic STN neurons would be suppressed.

Certain personality disorders, including the borderline and antisocial types, demonstrate focal deficits in brain disorders including "hypofrontality." Direct or indirect optogenetic excitation of these regions is anticipated to produce improvement of symptoms. Abnormal bursts of activity in the amygdala are also known to precipitate sudden, unprompted flights into rage: a symptom of borderline personality disorder, as well as other conditions, which can benefit from optogenetic stabilization of the amygdala. Optogenetic approaches could improve communication and synchronization between different parts of the brain, including amygdala, striatum, and frontal cortex, which could help in reducing impulsiveness and improving insight.

The amygdalocentric model of post-traumatic-stress disorder (PTSD) proposes that it is associated with hyperarousal of the amygdala and insufficient top-down control by the medial prefrontal cortex and the hippocampus. Accordingly, PTSD may be treated with optogenetic stabilization of the amyedale or hippocampus.

Schizophrenia is characterized by abnormalities including auditory hallucinations. These might be treated by suppression of the auditory cortex using optogenetic stabilization. Hypofrontality associated with schizophrenia might be treated with optogenetic excitation in the affected frontal regions. Optogenetic approaches could improve communication and synchronization between different parts of the brain which could help in reducing misattribution of self-generated stimuli as foreign.

Optogenetic stabilization of cells within the arcuate nucleus of the medial hypothalamus, which contain peptide products of pro-opiomelanocortin (POMC) and cocaine-and-amphetamine-regulating transcript (CART) can be used to reduce compulsive sexual behavior. Optogentic excitation of cells within the arcuate nucleus of the medial hypothalamus which contain peptide products of pro-opiomelanocortin (POMC) and cocaine-and-amphetamine-regulating transcript (CART) may be used to increase sexual interest in the treatment of cases of disorders of sexual desire. In the treatment of disorders of hypoactive sexual desire testosterone production by the testes and the adrenal glands can be increased through optogenetic excitation of the pituitary gland. Optogentic excitation of the nucleus accumbens can be used for the treatment of anorgasmia.

The suprachiasmatic nucleus secretes melatonin, which serves to regulate sleep/wake cycles. Optogenetic excitation to the suprachiasmic nucleus can be used to increase melatonin production, inducing sleep, and thereby treating insomnia. Orexin (hypocretin) neurons strongly excite numerous brain nuclei in order to promote wakefulness. Optogentetic excitation of orexin-producing cell populations can be used to treat narcolepsy, and chronic daytime sleepiness.

Optogenetic stimulation of the supraoptic nucleus may be used to induce secretion of oxytocin, can be used to promote parturition during childbirth, and can be used to treat disorders of social attachment.

Like muscular palsies, the motor functions that have been de-afferented by a spinal cord injury may be treated with optogenetic excitation to cause contraction, and optogenetic stabilization to cause relaxation. This latter relaxation via optogenetic stabilization approach may also be used to prevent muscle wasting, maintain tone, and permit coordinated movement as opposing muscle groups are contracted. Likewise, frank spasticity may be treated via optogenetic stabilization. Re-growth of new spinal neuronal tracts may be encouraged via optogenetic excitation, which serves to signal stem cells to sprout axons and dendrites, and to integrate themselves with the network.

Stroke deficits include personality change, motor deficits, sensory deficits, cognitive loss, and emotional instability. One strategy for the treatment of stroke deficits is to provide optogenetic stimulation to brain and body structures that have been deafferented from excitatory connections. Similarly, optogenetic stabilization capabilities can be imparted on brain and body structures that have been deafferented from inhibitory connections.

Research indicates that the underlying pathobiology in Tourette's syndrome is a phasic dysfunction of dopamine transmission in cortical and subcortical regions, the thalamus, basal ganglia and frontal cortex. In order to provide therapy, affected areas are preferably first identified using techniques including functional brain imaging and magnetoencephalography (MEG). Whether specifically identified or not, optogenetic stabilization of candidate tracts may be used to suppress motor tics. Post-implantation empirical testing of device parameters reveals which sites of optogenetic stabilization, and which are unnecessary to continue.

In order to treat disorders of urinary or fecal incontinence optogenetic stabilization can be used to the sphincters, for example via optogenetic stabilization of the bladder detrussor smooth muscle or innervations of that muscle. When micturation is necessary, these optogenetic processes are turned off, or alternatively can be reversed, with optogenetic stabilization to the (external) urinary sphincter, and optogenetic excitation of the bladder detrussor muscle or its innervations. When a bladder has been deafferentated, for example, when the sacral dorsal roots are cut or destroyed by diseases of the dorsal roots such as tabes dorsalis in humans, all reflex contractions of the bladder are abolished, and the bladder becomes distended. Optogenetic excitation of the muscle directly can be used to restore tone to the detrussor, prevent kidney damage, and to assist with the micturition process. As the bladder becomes "decentralized" and hypersensitive to movement, and hence prone to incontinence, optogenetic stabilization to the bladder muscle can be used to minimize this reactivity of the organ.

In order to selectively excite/inhibit a given population of neurons, for example those involved in the disease state of an illness, several strategies can be used to target the optogenetic proteins/molecules to specific populations.

For various embodiments of the present invention, genetic targeting may be used to express various optogenetic proteins or molecules. Such targeting involves the targeted expression of the optogenetic proteins/molecules via genetic control elements such as promoters (e.g., Parvalbumin, Somatostatin, Cholecystokinin, GFAP), enhancers/silencers (e.g., Cytomaglovirus Immediate Early Enhancer), and other transcriptional or translational regulatory elements (e.g. Woodchuck Hepatitis Virus Post-transcriptional Regulatory Element). Permutations of the promoter+enhancer+regulatory element combination can be used to restrict the expression of optogenetic probes to genetically-defined populations.

Various embodiments of the present invention may be implemented using spatial/anatomical targeting. Such targeting takes advantage of the fact that projection patterns of neurons, virus or other reagents carrying genetic information (DNA plasmids, fragments, etc), can be focally delivered to an area where a given population of neurons project to. The genetic material will then be transported back to the bodies of the neurons to mediate expression of the optogenetic probes. Alternatively, if it is desired to label cells in a focal region, viruses or genetic material may be focally delivered to the interested region to mediate localized expression.

Various gene delivery systems are useful in implementing one or more embodiments of the present invention. One such delivery system is Adeno-Associated Virus (AAV). AAV can be used to deliver a promoter+optogenetic probe cassett to a specific region of interest. The choice of promoter will drive expression in a specific population of neurons. For example, using the CaMKIIa promoter will drive excitatory neuron specific expression of optogenetic probes. AAV will mediate long-term expression of the optogenetic probe for at least 1 year or more. To achieve more specificity, AAV may be pseudotyped with specific serotypes 1 to 8, with each having different trophism for different cell types. For instance, serotype 2 and 5 is known to have good neuron-specific trophism.

Another gene deliver mechanism is the use of a retrovirus. HIV or other lentivirus-based retroviral vectors may be used to deliver a promoter+optogenetic probe cassette to a specific region of interest. Retroviruses may also be pseudotyped with the Rabies virus envelope glycoprotein to achieve retrograde transport for labeling cells based on their axonal projection patterns. Retroviruses integrate into the host cell's genome, therefore are capable of mediating permanent expression of the optogenetic probes. Non-lentivirus based retroviral vectors can be used to selectively label dividing cells.

Gutless Adenovirus and Herpes Simplex Virus (HSV) are two DNA based viruses that can be used to deliver promoter+ optogenetic probe cassette into specific regions of the brain as well. HSV and Adenovirus have much larger packaging capacities and therefore can accommodate much larger promoter elements and can also be used to deliver multiple optogenetic probes or other therapeutic genes along with optogenetic probes.

Focal Electroporation can also be used to transiently transfect neurons. DNA plasmids or fragments can be focally delivered into a specific region of the brain. By applying mild electrical current, surrounding local cells will receive the DNA material and expression of the optogenetic probes.

In another instance, lipofection can be used by mixing genetic material with lipid reagents and then subsequently injected into the brain to mediate transfect of the local cells.

Various embodiments involve the use of various control elements. In addition to genetic control elements, other control elements (particularly promoters and enhancers whose activities are sensitive to chemical, magnetic stimulation, or infrared radiation) can be used to mediate temporally-controlled expression of the optogenetic probes. For example, a promoter whose transcriptional activity is subject to infrared radiation allows one to use focused radiation to fine tune the expression of optogenetic probes in a focal region at only the desired time.

According to one embodiment of the present invention, the invention may be used in animal models of DBS, for example in Parkinsonian rats, to identify the target cell types responsible for therapeutic effects (an area of intense debate and immense clinical importance). This knowledge alone may lead to the development of improved pharmacological and surgical strategies for treating human disease.

According to another embodiment of the present invention, genetically-defined cell types may be linked with complex systems-level behaviors, and may allow the elucidation of the precise contribution of different cell types in many different brain regions to high-level organismal functioning.

Other aspects and embodiments are directed to systems, methods, kits, compositions of matter and molecules for ion pumps or for controlling inhibitory currents in a cell (e.g., in in vivo and in vitro environments). As described throughout this disclosure, including the claims, such systems, methods, kits, compositions of matter are realized in manners consistent herewith. For example, in one embodiment, the present invention is directed to an assembly or kit of parts, having a product containing an NpHR-based molecular variant and another opsin-based molecule (ChR2-based and or NpHR-based) as a combined preparation for use in the treatment of disease of a neurological or CNS disorder (as a category of disorder types or a specific disorder as exemplified herein), wherein at least the NpHR-based molecular variant is useful for expressing a light-activated NpHR-based molecule that responds to light by producing an inhibitory current to dissuade depolarization of a cell, and wherein a high expression of the molecule manifests a toxicity level that is less than about 75%.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. For instance, such changes may include additional NPHR-based sequences other than those listed in the immediately following Appendix. Such modifications and changes do not depart from the true spirit and scope of the present invention, which is set forth in the following appended claims.

What is claimed is:

1. An isolated nucleic acid comprising a mammalian codon optimized nucleotide sequence that encodes a variant opsin polypeptide derived from *Natromonas pharaonis* (NpHR), wherein the variant NpHR polypeptide comprises a heterologous endoplasmic reticulum (ER) export signal comprising the amino acid sequence set forth in SEQ ID NO: 16, wherein the variant NpHR polypeptide inhibits depolarization of a neuron in response to light of a wavelength that activates the variant NpHR polypeptide, and wherein the variant NpHR polypeptide exhibits reduced toxicity in the neuron compared to toxicity induced by wild-type NpHR.

2. The nucleic acid of claim 1, wherein the variant NpHR polypeptide comprises a heterologous signal peptide.

3. The nucleic acid of claim 2, wherein the heterologous signal peptide is a nicotinic acetylcholine receptor signal peptide.

4. The nucleic acid of claim 3, wherein the heterologous signal peptide comprises the amino acid sequence set forth in SEQ ID NO:13.

5. A recombinant expression vector comprising the nucleic acid of claim 1.

6. The recombinant expression vector of claim 5, wherein the nucleotide sequence is operably linked to a neuron-specific promoter.

7. The recombinant expression vector of claim 6, wherein the neuron-specific promoter is a CaMKIIα promoter.

8. The recombinant expression vector of claim 6, wherein the neuron-specific promoter is a cholinergic neuron-specific promoter.

9. The recombinant expression vector of claim 5, wherein the expression vector is a viral expression vector.

10. The recombinant expression vector of claim 9, wherein the viral expression vector is an adeno-associated viral vector.

11. The nucleic acid of claim 5, wherein the variant NpHR polypeptide is encoded by nucleotides 1-873 of SEQ ID NO:1.

12. The recombinant expression vector of claim 9, wherein the viral expression vector is a lentivirus vector.

* * * * *

SEQUENCE LISTING

```
<160> NUMBER OF SEQ ID NOS: 24

<210> SEQ ID NO 1
<211> LENGTH: 1599
<212> TYPE: DNA
<213> ORGANISM: Artificial Sequence
<220> FEATURE:
<223> OTHER INFORMATION: humanized codon optimized sequence from
      Natronomonas pharaonis

<400> SEQUENCE: 1
atgacagaga    ccctgcctcc    cgtgaccgag    agtgccgtgg    cccttcaagc    cgaggttacc        60
caaagggagt    tgttcgagtt    cgtgctgaac    gacccttttgc    ttgcaagcag    tctctatatc       120
aacatcgcac    ttgcaggact    gagtatactg    ctgttcgttt    ttatgacccg    aggactcgat       180
gatccacggg    caaaacttat    tgctgtgtca    accatccttg    tgcctgtcgt    cagcattgcc       240
tcctacactg    gattggcgag    cggcctgaca    atttccgttc    ttgaaatgcc    agcgggccat       300
tttgcagaag    gcagctcagt    gatgctggga    ggagaagagg    tagatggtgt    agtcaccatg       360
tggggacggt    atctcacctg    ggcactttcc    acgcccatga    ttctcctcgc    tctgggtctc       420
ctggccggaa    gcaatgctac    aaagctcttc    acagctatca    ctttcgatat    cgctatgtgc       480
gtgactggcc    ttgccgcggc    cctgactacc    tcctcccacc    tcatgagatg    gttctggtac       540
gctatcagtt    gtgcatgctt    tctggtggtc    ttgtatatcc    tgctggtgga    gtgggcacag       600
gacgccaaag    ccgcgggaac    cgctgacatg    ttcaataccc    tgaagctgtt    gacagtagtg       660
atgtggctgg    ggtatccaat    tgtgtgggct    cttggagtcg    agggtatcgc    ggtgttgccc       720
```

```
gttggggtga cgagctgggg atattctttc ctggatatcg tggcaaagta cattttcgca    780
ttcttgctcc tgaactatct gacgtcaaac gaatctgtcg tgtccggcag cattttggat    840
gttccatctg cttctgggac cccggctgat gatgcggccg ccgtgagcaa gggcgaggag    900
ctgttcaccg gggtggtgcc catcctggtc gagctggacg gcgacgtaaa cggccacaag    960
ttcagcgtgt ccggcgaggg cgagggcgat gccacctacg gcaagctgac cctgaagttc   1020
atctgcacca ccggcaagct gcccgtgccc tggcccaccc tcgtgaccac cttcggctac   1080
ggcctgcagt gcttcgcccg ctaccccgac cacatgaagc agcacgactt cttcaagtcc   1140
gccatgcccg aaggctacgt ccaggagcgc accatcttct tcaaggacga cggcaactac   1200
aagacccgcg ccgaggtgaa gttcgagggc gacacccctg tgaaccgcat cgagctgaag   1260
ggcatcgact tcaaggagga cggcaacatc ctggggcaca gctggagta caactacaac   1320 agccacaacg tctatatcat ggccgacaag cagaagaacg gcatcaaggt gaacttcaag   1380
atccgccaca acatcgagga cggcagcgtg cagctcgccg accactacca gcagaacacc   1440
cccatcggcg acggccccgt gctgctgccc gacaaccact acctgagcta ccagtccgcc   1500
ctgagcaaag accccaacga gaagcgcgat cacatggtcc tgctggagtt cgtgaccgcc   1560
gccgggatca ctctcggcat ggacgagctg tacaagtaa                          1599
```

<210> SEQ ID NO 2
<211> LENGTH: 1599
<212> TYPE: DNA
<213> ORGANISM: Artificial Sequence
<220> FEATURE:
<223> OTHER INFORMATION: Original codons from from Natronomonas
      pharaonis with EYEFP

<400> SEQUENCE: 2

```
atgactgaga cattgccacc ggtaacggaa tcggctgttg cgctacaggc ggaggtgacc     60
cagagggagc tgttcgagtt cgttctcaac gaccccctcc tcgccagttc gctgtatatt    120
aatatcgcac tggcagggct gtcgatactg cttttcgtgt tcatgacgcg cggactcgac    180
gacccacggg cgaaactcat cgccgtttcg acgattttgg tgccggtggt ctctatcgcg    240
agctacaccg gccttgcatc ggggctcacc atcagcgtcc tcgagatgcc agccggccac    300
ttcgccgagg ggtcctcggt gatgctcggc ggcgaagagg tagacggcgt cgtgacgatg    360
tggggccgct atctgacgtg ggcccttcg acaccgatga tactgctggc gcttgggctg    420
cttgctggct ctaacgccac gaagctcttt accgccatca ccttcgacat cgcgatgtgt    480
gtcaccggcc tcgcagccgc gctgacgacc tcttcgcacc tgatgcggtg gttctggtac    540
gccatcagtt gtgcgtgttt cctcgtcgtc ctctacatcc tgctcgtcga gtgggcacag    600
gacgccaagg ctgccggtac tgcggatatg ttcaatacgc tgaagctgct gaccgttgtc    660
atgtggctcg gctaccccat cgtgtgggca ctcggcgttg agggcatcgc cgttcttccg    720
gtcggagtca cgtcgtgggg atacagcttc ctcgacatcg tcgcgaagta catcttcgcg    780
ttcctgctgc tcaactacct cacgtcgaac gagagcgtcg tctccggctc gatactcgac    840
gtgccgtccg cgtcgggcac tcccgctgac gacgcggccg ccgtgagcaa gggcgaggag    900
ctgttcaccg gggtggtgcc catcctggtc gagctggacg gcgacgtaaa cggccacaag    960
ttcagcgtgt ccggcgaggg cgagggcgat gccacctacg gcaagctgac cctgaagttc   1020
atctgcacca ccggcaagct gcccgtgccc tggcccaccc tcgtgaccac cttcggctac   1080
ggcctgcagt gcttcgcccg ctaccccgac cacatgaagc agcacgactt cttcaagtcc   1140
```

```
gccatgcccg aaggctacgt ccaggagcgc accatcttct tcaaggacga cggcaactac    1200
aagacccgcg ccgaggtgaa gttcgagggc gacaccctgg tgaaccgcat cgagctgaag    1260
ggcatcgact tcaaggagga cggcaacatc ctggggcaca agctggagta caactacaac    1320
agccacaacg tctatatcat ggccgacaag cagaagaacg gcatcaaggt gaacttcaag    1380
atccgccaca acatcgagga cggcagcgtg cagctcgccg accactacca gcagaacacc    1440
cccatcggcg acggccccgt gctgctgccc gacaaccact acctgagcta ccagtccgcc    1500
ctgagcaaag accccaacga aaagcgcgat cacatggtcc tgctggagtt cgtgaccgcc    1560
gccgggatca ctctcggcat ggacgagctg tacaagtaa                           1599
```

<210> SEQ ID NO 3
<211> LENGTH: 1641
<212> TYPE: DNA
<213> ORGANISM: Artificial Sequence
<220> FEATURE:
<223> OTHER INFORMATION: humanized codon optimized sequence from
      Natronomonas pharaonis with signal peptide (23aa) from nicotinic
      acetylcholine receptor added to the N-terminus

<400> SEQUENCE: 3

```
atgaggggta cgcccctgct cctcgtcgtc tctctgttct ctctgcttca ggacacagag      60
accctgcctc ccgtgaccga gagtgccgtg gcccttcaag ccgaggttac ccaaagggag     120
ttgttcgagt tcgtgctgaa cgacccttttg cttgcaagca gtctctatat caacatcgca    180
cttgcaggac tgagtatact gctgttcgtt tttatgaccc gaggactcga tgatccacgg     240
gcaaaactta ttgctgtgtc aaccatcctt gtgcctgtcg tcagcattgc ctcctacact     300
ggattggcga gcggcctgac aatttccgtt cttgaaatgc cagcgggcca ttttgcagaa     360
ggcagctcag tgatgctggg aggagaagag gtagatggtg tagtcaccat gtggggacgg     420
tatctcacct gggcactttc cacgcccatg attctcctcg ctctgggtct cctggccgga     480
agcaatgcta caaagctctt cacagctatc actttcgata tcgctatgtg cgtgactggc     540
cttgccgcgg ccctgactac ctcctcccac tcatgagat ggttctggta cgctatcagt     600
tgtgcatgct ttctggtggt cttgtatatc ctgctggtgg agtgggcaca ggacgccaaa     660
gccgcgggaa ccgctgacat gttcaatacc ctgaagctgt tgacagtagt gatgtggctg     720
gggtatccaa ttgtgtgggc tcttggagtc gagggtatcg cggtgttgcc cgttggggtg     780
acgagctggg gatattcttt cctggatatc gtggcaaagt acatttttcgc attcttgctc     840 ctgaactatc tgacgtcaaa cgaatctgtc gtgtccggca gcatttttga tgttccatct     900
gcttctggga ccccggctga tgatgtgagc aagggcgagg agctgttcac cggggtggtg     960
cccatcctgg tcgagctgga cggcgacgta aacggccaca agttcagcgt gtccggcgag    1020
ggcgagggcg atgccaccta cggcaagctg accctgaagt tcatctgcac caccggcaag    1080
ctgcccgtgc cctggcccac cctcgtgacc accttcggct acggcctgca gtgcttcgcc    1140 cgctacccccg accacatgaa gcagcacgac ttcttcaagt ccgccatgcc cgaaggctac    1200
gtccaggagc gcaccatctt cttcaaggac gacggcaact acaagacccg cgccgaggtg    1260
aagttcgagg gcgacaccct ggtgaaccgc atcgagctga agggcatcga cttcaaggag    1320
gacggcaaca tcctggggca caagctggag tacaactaca acagccacaa cgtctatatc    1380
atggccgaca agcagaagaa cggcatcaag gtgaacttca gatccgccca caacatcgag    1440
gacggcagcg tgcagctcgc cgaccactac cagcagaaca cccccatcgg cgacggcccc    1500
gtgctgctgc ccgacaacca ctacctgagc taccagtccg ccctgagcaa agaccccaac    1560
```

```
gagaagcgcg atcacatggt cctgctggag ttcgtgaccg ccgccgggat cactctcggc    1620
atggacgagc tgtacaagta a                                              1641

<210> SEQ ID NO 4
<211> LENGTH: 1605
<212> TYPE: DNA
<213> ORGANISM: Artificial Sequence
<220> FEATURE:
<223> OTHER INFORMATION: humanized codon optimized sequence from
      Natronomonas pharaonis with the PDZ binding motif ETQZ added to
      the C-terminus

<400> SEQUENCE: 4
atgacagaga ccctgcctcc cgtgaccgag agtgccgtgg cccttcaagc cgaggttacc      60
caaagggagt tgttcgagtt cgtgctgaac gacccttttgc ttgcaagcag tctctatatc    120
```

C-terminus to promote interaction with actin-binding protein
filamin

<400> SEQUENCE: 5

| | |
|---|---|
| atgacagaga ccctgcctcc cgtgaccgag agtgccgtgg cccttcaagc cgaggttacc | 60 |
| caaagggagt tgttcgagtt cgtgctgaac gacccttttgc ttgcaagcag tctctatatc | 120 |
| aacatcgcac ttgcaggact gagtatactg ctgttcgttt ttatgacccg aggactcgat | 180 |
| gatccacggg caaaacttat tgctgtgtca accatccttg tgcctgtcgt cagcattgcc | 240 |
| tcctacactg gattggcgag cggcctgaca atttccgttc ttgaaatgcc agcgggccat | 300 |
| tttgcagaag gcagctcagt gatgctggga ggagaagagg tagatggtgt agtcaccatg | 360 |
| tggggacggt atctcacctg gcactttcc acgcccatga ttctcctcgc tctgggtctc | 420 |
| ctggccggaa gcaatgctac aaagctcttc acagctatca ctttcgatat cgctatgtgc | 480 |
| gtgactggcc ttgccgcggc cctgactacc tcctcccacc tcatgagatg gttctggtac | 540 |
| gctatcagtt gtgcatgctt tctggtggtc ttgtatatcc tgctggtgga gtgggcacag | 600 |
| gacgccaaag ccgcgggaac cgctgacatg ttcaataccc tgaagctgtt gacagtagtg | 660 |
| atgtggctgg ggtatccaat tgtgtgggct cttggagtcg agggtatcgc ggtgttgccc | 720 |
| gttggggtga cgagctgggg atattctttc ctggatatcg tggcaaagta cattttcgca | 780 |
| ttcttgctcc tgaactatct gacgtcaaac gaatctgtcg tgtccggcag cattttggat | 840 |
| gttccatctg cttctgggac cccggctgat gatgcggccg ccgtgagcaa gggcgaggag | 900 |
| ctgttcaccg gggtggtgcc catcctggtc gagctggacg gcgacgtaaa cggccacaag | 960 |
| ttcagcgtgt ccggcgaggg cgagggcgat gccacctacg gcaagctgac cctgaagttc | 1020 |
| atctgcacca ccggcaagct gcccgtgccc tggcccaccc tcgtgaccac cttcggctac | 1080 |
| ggcctgcagt gcttcgcccg ctaccccgac cacatgaagc agcacgactt cttcaagtcc | 1140 |
| gccatgcccg aaggctacgt ccaggagcgc accatcttct tcaaggacga cggcaactac | 1200 |
| aagacccgcg ccgaggtgaa gttcgagggc gacaccctgg tgaaccgcat cgagctgaag | 1260 |
| ggcatcgact tcaaggagga cggcaacatc ctggggcaca agctggagta caactacaac | 1320 |
| agccacaacg tctatatcat ggccgacaag cagaagaacg gcatcaaggt gaacttcaag | 1380 |
| atccgccaca acatcgagga cggcagcgtg cagctcgccg accactacca gcagaacacc | 1440 |
| cccatcggcg acggccccgt gctgctgccc gacaaccact acctgagcta ccagtccgcc | 1500 |
| ctgagcaaag cccccaacga gaagcgcgat cacatggtcc tgctggagtt cgtgaccgcc | 1560 |
| gccgggatca ctctcggcat ggacgagctg tacaagccga ccccgccgta a | 1611 |

<210> SEQ ID NO 6
<211> LENGTH: 1605
<212> TYPE: DNA
<213> ORGANISM: Artificial Sequence
<220> FEATURE:
<223> OTHER INFORMATION: humanized codon optimized sequence from
Natronomonas pharaonis with the ER export signal added to the
C-terminus

<400> SEQUENCE: 6

| | |
|---|---|
| atgacagaga ccctgcctcc cgtgaccgag agtgccgtgg cccttcaagc cgaggttacc | 60 |
| caaagggagt tgttcgagtt cgtgctgaac gacccttttgc ttgcaagcag tctctatatc | 120 |
| aacatcgcac ttgcaggact gagtatactg ctgttcgttt ttatgacccg aggactcgat | 180 |
| gatccacggg caaaacttat tgctgtgtca accatccttg tgcctgtcgt cagcattgcc | 240 |

```
tcctacactg gattggcgag cggcctgaca atttccgttc ttgaaatgcc agcgggccat      300
tttgcagaag cagctcagt gatgctggga ggagaagagg tagatggtgt agtcaccatg      360
tggggacggt atctcacctg gcactttcc acgcccatga ttctcctcgc tctgggtctc      420
ctggccggaa gcaatgctac aaagctcttc acagctatca ctttcgatat cgctatgtgc      480
gtgactggcc ttgccgcggc cctgactacc tcctcccacc tcatgagatg gttctggtac      540
gctatcagtt gtgcatgctt tctggtggtc ttgtatatcc tgctggtgga gtgggcacag      600
gacgccaaag ccgcgggaac cgctgacatg ttcaataccc tgaagctgtt gacagtagtg      660
atgtggctgg ggtatccaat tgtgtgggct cttggagtcg agggtatcgc ggtgttgccc      720
gttggggtga cgagctgggg atattctttc ctggatatcg tggcaaagta cattttcgca      780
ttcttgctcc tgaactatct gacgtcaaac gaatctgtcg tgtccggcag cattttggat      840
gttccatctg cttctgggac cccggctgat gatgtgagca agggcgagga gctgttcacc      900
ggggtggtgc ccatcctggt cgagctggac ggcgacgtaa acggccacaa gttcagcgtg      960
tccggcgagg gcgagggcga tgccacctac ggcaagctga ccctgaagtt catctgcacc     1020
accggcaagc tgcccgtgcc ctggcccacc ctcgtgacca ccttcggcta cggcctgcag     1080
tgcttcgccc gctaccccga ccacatgaag cagcacgact tcttcaagtc cgccatgccc     1140
gaaggctacg tccaggagcg caccatcttc ttcaaggacg acggcaacta caagacccgc     1200
gccgaggtga agttcgaggg cgacaccctg gtgaaccgca tcgagctgaa gggcatcgac     1260
ttcaaggagg acggcaacat cctggggcac aagctggagt acaactacaa cagccacaac     1320
gtctatatca tggccgacaa gcagaagaac ggcatcaagg tgaacttcaa gatccgccac     1380
aacatcgagg acggcagcgt gcagctcgcc gaccactacc agcagaacac ccccatcggc     1440
gacggccccg tgctgctgcc cgacaaccac tacctgagct accagtccgc cctgagcaaa     1500
gaccccaacg agaagcgcga tcacatggtc ctgctggagt tcgtgaccgc cgccgggatc     1560
actctcggca tggacgagct gtacaaggtg ctgggcagcc tgtaa                     1605
```

<210> SEQ ID NO 7
<211> LENGTH: 1644
<212> TYPE: DNA
<213> ORGANISM: Artificial Sequence
<220> FEATURE:
<223> OTHER INFORMATION: humanized codon optimized sequence from
      Natronomonas pharaonis with a signal peptide (first 15aa) from
      ChR2 (derived from Chlamydomonas reinhardtii) is added to the
      N-terminus

<400> SEQUENCE: 7

```
atggattatg gaggcgccct gagtgccgtt gggcgcgagc tgctatttac agagaccctg       60
cctcccgtga ccgagagtgc cgtggccctt caagccgagg ttacccaaag ggagttgttc      120
gagttcgtgc tgaacgaccc tttgcttgca agcagtctct atatcaacat cgcacttgca      180
ggactgagta tactgctgtt cgtttttatg acccgaggac tcgatgatcc acgggcaaaa      240
cttattgctg tgtcaaccat ccttgtgcct gtcgtcagca ttgcctccta cactggattg      300
gcgagcggcc tgacaatttc cgttcttgaa atgccagcgg ccatttttgc agaaggcagc      360
tcagtgatgc tgggaggaga agaggtagat ggtgtagtcc catgtgggg acggtatctc      420 acctgggcac tttccacgcc catgattctc ctcgctctgg tctcctggc cggaagcaat      480 gctacaaagc tcttcacagc tatcactttc gatatcgcta tgtgcgtgac tggccttgcc      540
gcggccctga ctacctcctc ccacctcatg agatggttct ggtacgctat cagttgtgca      600
```

```
tgctttctgg tggtcttgta tatcctgctg gtggagtggg cacaggacgc caaagccgcg      660
ggaaccgctg acatgttcaa taccctgaag ctgttgacag tagtgatgtg gctggggtat      720
ccaattgtgt gggctcttgg agtcgagggt atcgcggtgt tgcccgttgg ggtgacgagc      780
tggggatatt ctttcctgga tatcgtggca aagtacattt tcgcattctt gctcctgaac      840
tatctgacgt caaacgaatc tgtcgtgtcc ggcagcattt tggatgttcc atctgcttct      900
gggaccccgg ctgatgatgc ggccgccgtg agcaagggcg aggagctgtt caccggggtg      960
gtgcccatcc tggtcgagct ggacggcgac gtaaacggcc acaagttcag cgtgtccggc     1020
gagggcgagg gcgatgccac ctacggcaag ctgaccctga agttcatctg caccaccggc     1080
aagctgcccg tgccctggcc caccctcgtg accaccttcg gctacggcct gcagtgcttc     1140
gcccgctacc ccgaccacat gaagcagcac gacttcttca gtccgccat gcccgaaggc      1200
tacgtccagg agcgcaccat cttcttcaag gacgacggca actacaagac ccgcgccgag     1260
gtgaagttcg agggcgacac cctggtgaac cgcatcgagc tgaagggcat cgacttcaag     1320
gaggacggca acatcctggg gcacaagctg gagtacaact acaacagcca caacgtctat     1380
atcatggccg acaagcagaa gaacggcatc aaggtgaact tcaagatccg ccacaacatc     1440
gaggacggca gcgtgcagct cgccgaccac taccagcaga cacccccat cggcgacggc      1500
cccgtgctgc tgcccgacaa ccactacctg agctaccagt ccgccctgag caaagacccc     1560
aacgagaagc gcgatcacat ggtcctgctg gagttcgtga ccgccgccgg gatcactctc     1620
ggcatggacg agctgtacaa gtaa                                            1644
```

<210> SEQ ID NO 8
<211> LENGTH: 1665
<212> TYPE: DNA
<213> ORGANISM: Artificial Sequence
<220> FEATURE:
<223> OTHER INFORMATION: humanized codon optimized sequence from
      Natronomonas pharaonis with a signal peptide (23aa) from nicotinic
      acetylcholine receptor is added to the N-terminus

<400> SEQUENCE: 8

```
atgggtcttc gtgctcttat gctttggctt cttgctgctg ctggtcttgt tcgtgaatct      60
cttcaaggta cagagaccct gcctcccgtg accgagagtg ccgtggccct tcaagccgag     120
gttacccaaa gggagttgtt cgagttcgtg ctgaacgacc ttttgcttgc aagcagtctc     180
tatatcaaca tcgcacttgc aggactgagt atactgctgt tcgttttttat gacccgagga     240
ctcgatgatc cacgggcaaa acttattgct gtgtcaacca tccttgtgcc tgtcgtcagc     300
attgcctcct acactggatt ggcgagcggc ctgacaattt ccgttcttga atgccagcg      360
ggccattttg cagaaggcag ctcagtgatg ctgggaggag aagaggtaga tggtgtagtc     420
accatgtggg gacggtatct cacctgggca cttttccacg ccatgattct cctcgctctg     480
ggtctcctgg ccggaagcaa tgctacaaag ctcttcacag ctatcacttt cgatatcgct     540
atgtgcgtga ctggccttgc cgcggccctg actacctcct cccacctcat gagatggttc     600
tggtacgcta tcagttgtgc atgctttctg gtggtcttgt atatcctgct ggtggagtgg     660
gcacaggacg ccaaagccgc gggaaccgct gacatgttca ataccctgaa gctgttgaca     720
gtagtgatgt ggctggggta tccaattgtg tgggctcttg gagtcgaggg tatcgcggtg     780
ttgcccgttg gggtgacgag ctggggatat tctttcctgg atatcgtggc aaagtacatt     840
ttcgcattct tgctcctgaa ctatctgacg tcaaacgaat ctgtcgtgtc cggcagcatt     900
ttggatgttc catctgcttc tgggaccccg gctgatgatg cggccgccgt gagcaagggc      960
```

```
gaggagctgt tcaccggggt ggtgcccatc ctggtcgagc tggacggcga cgtaaacggc    1020
cacaagttca gcgtgtccgg cgagggcgag ggcgatgcca cctacggcaa gctgaccctg    1080
aagttcatct gcaccaccgg caagctgccc gtgccctggc ccaccctcgt gaccaccttc    1140
ggctacggcc tgcagtgctt cgcccgctac cccgaccaca tgaagcagca cgacttcttc    1200
aagtccgcca tgcccgaagg ctacgtccag gagcgcacca tcttcttcaa ggacgacggc    1260
aactacaaga cccgcgccga ggtgaagttc gagggcgaca ccctggtgaa ccgcatcgag    1320
ctgaagggca tcgacttcaa ggaggacggc aacatcctgg gcacaagct ggagtacaac     1380 tacaacagcc acaacgtcta tatcatggcc gacaagcaga agaacggcat caaggtgaac    1440
ttcaagatcc gccacaacat cgaggacggc agcgtgcagc tcgccgacca ctaccagcag    1500 aacacccca tcggcgacgg ccccgtgctg ctgcccgaca ccactacct gagctaccag      1560 tccgccctga gcaaagaccc caacgagaag cgcgatcaca tggtcctgct ggagttcgtg    1620
accgccgccg ggatcactct cggcatggac gagctgtaca agtaa                   1665
```

<210> SEQ ID NO 9
<211> LENGTH: 1605
<212> TYPE: DNA
<213> ORGANISM: Artificial Sequence
<220> FEATURE:
<223> OTHER INFORMATION: humanized codon optimized sequence from
      Natronomonas pharaonis with the PDZ binding motif VSNL added to
      the C-terminus

<400> SEQUENCE: 9

```
atgacagaga ccctgcctcc cgtgaccgag agtgccgtgg cccttcaagc cgaggttacc     60
caaagggagt tgttcgagtt cgtgctgaac gacccttttgc ttgcaagcag tctctatatc   120
aacatcgcac ttgcaggact gagtatactg ctgttcgttt ttatgacccg aggactcgat    180
gatccacggg caaaacttat tgctgtgtca accatccttg tgcctgtcgt cagcattgcc    240
tcctacactg gattggcgag cggcctgaca atttccgttc ttgaaatgcc agcgggccat    300
tttgcagaag gcagctcagt gatgctggga ggagaagagg tagatggtgt agtcaccatg    360
tggggacggt atctcacctg gcacttttcc acgcccatga ttctcctcgc tctgggtctc    420
ctggccggaa gcaatgctac aaagctcttc acagctatca ctttcgatat cgctatgtgc    480
gtgactggcc ttgccgcggc cctgactacc tcctcccacc tcatgagatg gttctggtac    540
gctatcagtt gtgcatgctt tctggtggtc ttgtatatcc tgctggtgga gtgggcacag    600
gacgccaaag ccgcgggaac cgctgacatg ttcaataccc tgaagctgtt gacagtagtg    660
atgtggctgg ggtatccaat tgtgtgggct cttggagtcg agggtatcgc ggtgttgccc    720
gttggggtga cgagctgggg atattctttc ctggatatcg tggcaaagta cattttcgca    780
ttcttgctcc tgaactatct gacgtcaaac gaatctgtcg tgtccggcag catttttggat   840 gttccatctg cttctgggac cccggctgat gatatggtga gcaagggcga ggagctgttc    900
accggggtgg tgcccatcct ggtcgagctg gacggcgacg taaacggcca agttcagc      960 gtgtccggcg agggcgaggg cgatgccacc tacggcaagc tgaccctgaa gttcatctgc    1020
accaccggca agctgccggt gccctggccc accctcgtga ccaccttcgg ctacggcctg    1080
cagtgcttcg cccgctaccc cgaccacatg aagcagcacg acttcttcaa gtccgccatg    1140
cccgaaggct acgtccagga gcgcaccatc ttcttcaagg acgacggcaa ctacaagacc    1200
cgcgccgagg tgaagttcga gggcgacacc ctggtgaacc gcatcgagct gaagggcatc    1260
```

```
gacttcaagg aggacggcaa catcctgggg cacaagctgg agtacaacta caacagccac    1320
aacgtctata tcatggccga caagcagaag aacggcatca aggtgaactt caagatccgc    1380
cacaacatcg aggacggcag cgtgcagctc gccgaccact accagcagaa cacccccatc    1440
ggcgacggcc ccgtgctgct gcccgacaac cactacctga ctaccagtc cgccctgagc     1500 aaagacccca acgagaagcg cgatcacatg gtcctgctgg agttcgtgac cgccgccggg    1560
atcactctcg gcatggacga gctgtacaag gtgagcaacc tgtaa                    1605
```

<210> SEQ ID NO 10
<211> LENGTH: 1599
<212> TYPE: DNA
<213> ORGANISM: Artificial Sequence
<220> FEATURE:
<223> OTHER INFORMATION: humanized codon optimized sequence from
      Natronomonas pharaonis with a hybrid construct of the ER export
      signal added to the C-terminus and the signal peptide (23aa) from
      nicotinic acetylcholine receptor added to the N-terminus

<400> SEQUENCE: 10

```
atgacagaga ccctgcctcc cgtgaccgag agtgccgtgg cccttcaagc cgaggttacc    60
caaagggagt gttcgagtt cgtgctgaac gaccctttgc ttgcaagcag tctctatatc    120
aacatcgcac ttgcaggact gagtatactg ctgttcgttt ttatgacccg aggactcgat    180
gatccacggg caaaacttat tgctgtgtca accatccttg tgcctgtcgt cagcattgcc    240
tcctacactg gattggcgag cggcctgaca atttccgttc ttgaaatgcc agcgggccat    300
tttgcagaag gcagctcagt gatgctggga ggagaagagg tagatggtgt agtcaccatg    360
tggggacggt atctcacctg gcactttcc acgcccatga ttctcctcgc tctgggtctc     420
ctggccggaa gcaatgctac aaagctcttc acagctatca ctttcgatat cgctatgtgc    480
gtgactggcc ttgccgcggc cctgactacc tcctcccacc tcatgagatg gttctggtac    540
gctatcagtt gtgcatgctt tctggtggtc ttgtatatcc tgctggtgga gtgggcacag    600
gacgccaaag ccgcgggaac cgctgacatg ttcaataccc tgaagctgtt gacagtagtg    660
atgtggctgg ggtatccaat tgtgtgggct cttggagtcg agggtatcgc ggtgttgccc    720
gttggggtga cgagctgggg atattctttc ctggatatcg tggcaaagta cattttcgca    780
ttcttgctcc tgaactatct gacgtcaaac gaatctgtcg tgtccggcag cattttggat    840
gttccatctg cttctgggac cccggctgat gatgcggccg ccgtgagcaa gggcgaggag    900
ctgttcaccg ggtggtgccc catcctggtc gagctggacg gcgacgtaaa cggccacaag    960
ttcagcgtgt ccggcgaggg cgagggcgat gccacctacg gcaagctgac cctgaagttc    1020
atctgcacca ccggcaagct gcccgtgccc tggcccaccc tcgtgaccac cttcggctac    1080
ggcctgcagt gcttcgcccg ctaccccgac cacatgaagc agcacgactt cttcaagtcc    1140
gccatgcccg aaggctacgt ccaggagcgc accatcttct tcaaggacga cggcaactac    1200
aagaccccgc ccgaggtgaa gttcgagggc gacaccctgg tgaaccgcat cgagctgaag    1260
ggcatcgact tcaaggagga cggcaacatc ctggggcaca gctggagta caactacaac    1320 agccacaacg tctatatcat ggccgacaag cagaagaacg gcatcaaggt gaacttcaag    1380
atccgccaca catcgagga cggcagcgtg cagctcgccg accactacca gcagaacacc    1440
cccatcggcg acggccccgt gctgctgccc gacaaccact acctgagcta ccagtccgcc    1500
ctgagcaaag accccaacga gaagcgcgat cacatggtcc tgctggagtt cgtgaccgcc    1560
gccgggatca ctctcggcat ggacgagctg tacaagtaa                           1599
```

```
<210> SEQ ID NO 11
<211> LENGTH: 14
<212> TYPE: PRT
<213> ORGANISM: Artificial Sequence
<220> FEATURE:
<223> OTHER INFORMATION: Signal peptide from ChR2

<400> SEQUENCE: 11

Asp Tyr Gly Gly Ala Leu Ser Ala Val Gly Arg Glu Leu Leu
1               5                   10

<210> SEQ ID NO 12
<211> LENGTH: 23
<212> TYPE: PRT
<213> ORGANISM: Artificial Sequence
<220> FEATURE:
<223> OTHER INFORMATION: signal peptide from nicotinic acetylcholine
      receptor

<400> SEQUENCE: 12

Met Gly Leu Arg Ala Leu Met Leu Trp Leu Leu Ala Ala Ala Gly Leu
1               5                   10                  15

Val Arg Glu Ser Leu Gln Gly
            20

<210> SEQ ID NO 13
<211> LENGTH: 18
<212> TYPE: PRT
<213> ORGANISM: Artificial Sequence
<220> FEATURE:
<223> OTHER INFORMATION: signal peptide from nicotinic acetylcholine
      receptor

<400> SEQUENCE: 13

Met Arg Gly Thr Pro Leu Leu Leu Val Val Ser Leu Phe Ser Leu Leu
1               5                   10                  15

Gln Asp

<210> SEQ ID NO 14
<211> LENGTH: 4
<212> TYPE: PRT
<213> ORGANISM: Artificial Sequence
<220> FEATURE:
<223> OTHER INFORMATION: PDZ binding motif ETQZ

<400> SEQUENCE: 14

Glu Thr Gln Glx
1

<210> SEQ ID NO 15
<211> LENGTH: 4
<212> TYPE: PRT
<213> ORGANISM: Artificial Sequence
<220> FEATURE:
<223> OTHER INFORMATION: PTPP sequence

<400> SEQUENCE: 15

Pro Thr Pro Pro
1

<210> SEQ ID NO 16
<211> LENGTH: 5
<212> TYPE: PRT
<213> ORGANISM: Artificial Sequence
<220> FEATURE:
<223> OTHER INFORMATION: ER export signal VLGSL
```

```
<400> SEQUENCE: 16

Val Leu Gly Ser Leu
1               5

<210> SEQ ID NO 17
<211> LENGTH: 5
<212> TYPE: PRT
<213> ORGANISM: Artificial Sequence
<220> FEATURE:
<223> OTHER INFORMATION: ER export signal VXXSL
<220> FEATURE:
<221> NAME/KEY: misc_feature
<222> LOCATION: (2)..(3)
<223> OTHER INFORMATION: Xaa can be any naturally occurring amino acid

<400> SEQUENCE: 17

Val Xaa Xaa Ser Leu
1               5

<210> SEQ ID NO 18
<211> LENGTH: 6
<212> TYPE: PRT
<213> ORGANISM: Artificial Sequence
<220> FEATURE:
<223> OTHER INFORMATION: ER export signal FXYENE
<220> FEATURE:
<221> NAME/KEY: misc_feature
<222> LOCATION: (2)..(2)
<223> OTHER INFORMATION: Xaa can be any naturally occurring amino acid

<400> SEQUENCE: 18

Phe Xaa Tyr Glu Asn Glu
1               5

<210> SEQ ID NO 19
<211> LENGTH: 4
<212> TYPE: PRT
<213> ORGANISM: Artificial Sequence
<220> FEATURE:
<223> OTHER INFORMATION: PDZ binding motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 19

Xaa Ser Xaa Val
1

<210> SEQ ID NO 20
<211> LENGTH: 4
<212> TYPE: PRT
<213> ORGANISM: Artificial Sequence
<220> FEATURE:
<223> OTHER INFORMATION: PDZ binding motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 20
```

```
Xaa Thr Xaa Val
1

<210> SEQ ID NO 21
<211> LENGTH: 4
<212> TYPE: PRT
<213> ORGANISM: Artificial Sequence
<220> FEATURE:
<223> OTHER INFORMATION: PDZ binding motif

<400> SEQUENCE: 21

Glu Thr Gln Val
1

<210> SEQ ID NO 22
<211> LENGTH: 4
<212> TYPE: PRT
<213> ORGANISM: Artificial Sequence
<220> FEATURE:
<223> OTHER INFORMATION: PDZ binding motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 22

Xaa Ser Xaa Leu
1

<210> SEQ ID NO 23
<211> LENGTH: 4
<212> TYPE: PRT
<213> ORGANISM: Artificial Sequence
<220> FEATURE:
<223> OTHER INFORMATION: PDZ binding motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 23

Xaa Thr Xaa Leu
1

<210> SEQ ID NO 24
<211> LENGTH: 4
<212> TYPE: PRT
<213> ORGANISM: Artificial Sequence
<220> FEATURE:
<223> OTHER INFORMATION: PDZ binding motif

<400> SEQUENCE: 24

Val Ser Asn Leu
1
```